US008338412B2

(12) United States Patent
Bemis et al.

(10) Patent No.: US 8,338,412 B2
(45) Date of Patent: Dec. 25, 2012

(54) INHIBITORS OF P38

(75) Inventors: Guy W. Bemis, Arlington, MA (US);
Francesco G. Salituro, Marlborough,
MA (US); John P. Duffy, Northborough,
MA (US); John E. Cochran, North
Andover, MA (US); **Edmund M.
Harrington**, South Boston, MA (US);
Mark A. Murcko, Holliston, MA (US);
Keith P. Wilson, Hopkinton, MA (US);
Michael Su, Newton, MA (US); **Vincent
P. Galullo**, Watertown, MA (US)

(73) Assignee: Vertex Pharmaceuticals Incorporated,
Cambridge, MA (US)

( * ) Notice: Subject to any disclaimer, the term of this patent is extended or adjusted under 35 U.S.C. 154(b) by 0 days.

(21) Appl. No.: 13/107,802

(22) Filed: May 13, 2011

(65) Prior Publication Data

US 2011/0281878 A1    Nov. 17, 2011

Related U.S. Application Data

(60) Division of application No. 12/062,495, filed on Apr. 3, 2008, now Pat. No. 7,951,809, which is a division of application No. 11/298,324, filed on Dec. 8, 2005, now Pat. No. 7,365,072, which is a continuation of application No. 10/622,320, filed on Jul. 17, 2003, now Pat. No. 7,205,305, which is a continuation of application No. 09/336,266, filed on Jun. 18, 1999, now Pat. No. 6,608,060, which is a continuation of application No. PCT/US97/23392, filed on Dec. 17, 1997, which is a continuation-in-part of application No. 08/862,925, filed on Jun. 10, 1997, now Pat. No. 6,147,080, which is a continuation-in-part of application No. 08/822,373, filed on Mar. 20, 1997, now Pat. No. 5,945,418.

(60) Provisional application No. 60/034,288, filed on Dec. 18, 1996.

(51) Int. Cl.
*C07D 487/04* (2006.01)
*A61K 31/5025* (2006.01)

(52) U.S. Cl. .................. 514/233.2; 514/248; 514/259.5; 544/117; 544/236; 544/282

(58) Field of Classification Search .................. 544/117, 544/236, 282; 514/233.2, 248, 259.5
See application file for complete search history.

(56) References Cited

U.S. PATENT DOCUMENTS

| 5,716,955 | A | 2/1998 | Adams et al. |
| 5,716,972 | A | 2/1998 | Adams et al. |
| 5,717,100 | A | 2/1998 | Selnick et al. |
| 5,753,664 | A | 5/1998 | Aono et al. |
| 5,945,418 | A | 8/1999 | Bemis et al. |
| 6,093,742 | A | 7/2000 | Salituro et al. |
| 6,147,080 | A | 11/2000 | Bemis et al. |
| 6,608,060 | B1 | 8/2003 | Bemis et al. |
| 6,632,945 | B2 | 10/2003 | Salituro et al. |
| 7,115,637 | B2 | 10/2006 | Salituro et al. |
| 7,205,305 | B2 | 4/2007 | Bemis et al. |
| 7,365,072 | B2 | 4/2008 | Bemis et al. |
| 7,423,049 | B2 | 9/2008 | Salituro et al. |
| 2009/0075981 | A1 | 3/2009 | Salituro et al. |

FOREIGN PATENT DOCUMENTS

| WO | 95/02591 A1 | 1/1995 |
| WO | 95/31451 A1 | 11/1995 |
| WO | 96/21654 A1 | 7/1996 |
| WO | 97/12876 A1 | 4/1997 |
| WO | 97/19065 A1 | 5/1997 |
| WO | 97/44467 A1 | 11/1997 |
| WO | 97/47618 A1 | 12/1997 |
| WO | 97/49689 A1 | 12/1997 |
| WO | 98/02430 A1 | 1/1998 |
| WO | 98/06715 A1 | 2/1998 |

OTHER PUBLICATIONS

Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Mass, R. D., Int. J. Radiation Oncology Bio. Phys.vol. 58(3): 932-940, 2004.
Fabbro et al. Pharmacology & therapeutics 93, 79-98, 2002.
Cohen et al., Current Opinion in Chemical Biology, 3,459-465, 1999.
Freshney et al.,Culture of Animal Cells, A Manual of Basic Technique, Alan R. Liss, Inc., 1983, New York, p. 4.
Dermer et al., Bio/Technology, 1994, 12:320.
Powell et al., British Journal of Dermatology, 141 802-810,1999.
Golub et al., Science, 286, 531-537,1999.
Turner et al., Current Pharmaceutical Design. 2, 209-224, 1996.
Sugar et al., Diagn. Microbial. Infect. Dis. 21: 129-133, 1995.
Snyder et al., J. Med. Liban 48(4): 208-214, 2000 (Abstract).
Brunet et al., Essays Biochem. 32: 1-16,1997 (Abstract).
Nagarkatti et al., J. Mol. Cell Cardiol. 30(8): 1651-1664, 1998 (Abstract).
Herlaar et al., Mol. Med. Today 5(10) 439-447, 1999 (Abstract).
Graninger et al., Curr. Opin. Rheumatol. 13(3):209-13, 2001 (Abstract).
Suzuki et al., FEBS Lett. 465:23-27, 2000.
Badger et al., Arthritis Rheum. 43: 175-183, 2000.
Hommes et al., Gastroenterology 122:7-14, 2002.

(Continued)

*Primary Examiner* — Deepak Rao
(74) *Attorney, Agent, or Firm* — VLP Law Group LLP; David A. Roise

(57) ABSTRACT

The present invention relates to inhibitors of p38, a mammalian protein kinase involved cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

19 Claims, No Drawings

OTHER PUBLICATIONS

Ballard-Croft, C. et al., Am. J. Physiol. Heart Circ. Physiol. 280:H1970-H1981, 2001.
Shimamoto et al., American Heart Association Annual Meeting, 1415 (2000).
Nick et al., J. Immunol. 164:2151-2159,2000.
Legos et al., Brain Research 892:70-77, 2001.
Barancik et al., J. Cardiovasc. Pharmacol. 35:474-483,2000.
Gallagher et al., "Regulation of Stress Induced Cytokine Production by Pyridinylimidazoles; Inhibition of CSBP Kinase," Bioorganic & Medicinal Chemistry, 5(1), pp. 49 64, (1997).
Badger et al., "Pharmacological Profile of SB 203580, a Selective Inhibitor of Cytokine Suppressive Binding Protein/p38 Kinase, in Animal Models of Arthritis, Bone Resorption, Endotoxin Shock and Immune Function," Journal of Pharmacology and Experimental Therapeutics, 279(3), pp. 1453-1461, (1996).
Gallagher et al., "2,4,5 Triaryl imidazole Inhibitors of IL 1 Biosynthesis," Bioorganic & Medicinal Chemistry Letters, 5 (11), pp. 1171-1176, (1995).
Layzer, "Degenerative Diseases of the Nervous System," Cecil Textbook of Medicine, 20th Edition, vol. 1 pp. 2050-2057 (1996).
Simone, "Oncology: Introduction," Cecil Textbook of Medicine, 20th Edition, vol. 1 pp. 1004-1010 (1996).
Damasio, "Alzheimer's Disease and Related Dementias," Cecil Textbook of Medicine, 20th Edition, vol. 1 pp. 1992-1996 (1996).
Douglas, "Introduction to Viral Diseases," Cecil Textbook of Medicine, 20th Edition, vol. 1 pp. 1739-1747 (1996).

\* cited by examiner

INHIBITORS OF P38

CROSS-REFERENCE TO RELATED APPLICATIONS

This application is a divisional of U.S. patent application Ser. No. 12/062,495, filed Apr. 3, 2008, now U.S. Pat. No. 7,951,809, which is a divisional of U.S. patent application Ser. No. 11/298,324, filed Dec. 8, 2005, now U.S. Pat. No. 7,365,072, which is a continuation of U.S. patent application Ser. No. 10/622,320, filed Jul. 17, 2003, now U.S. Pat. No. 7,205,305, which is a continuation of U.S. patent application Ser. No. 09/336,266, filed Jun. 18, 1999, now U.S. Pat. No. 6,608,060, which is a continuation of International Application No. PCT/US97/23392, filed Dec. 17, 1997, which is a continuation-in-part of U.S. patent application Ser. No. 08/862,925, filed Jun. 10, 1997, now U.S. Pat. No. 6,147,080, which is a continuation-in-part of U.S. patent application Ser. No. 08/822,373, filed Mar. 20, 1997, now U.S. Pat. No. 5,945,418, which claims the benefit of U.S. Provisional Application No. 60/034,288, filed Dec. 18, 1996, now abandoned, the disclosures of which are each incorporated herein by reference in their entireties.

TECHNICAL FIELD OF INVENTION

The present invention relates to inhibitors of p38, a mammalian protein kinase involved cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

BACKGROUND OF THE INVENTION

Protein kinases are involved in various cellular responses to extracellular signals. Recently, a family of mitogen-activated protein kinases (MAPK) have been discovered. Members of this family are Ser/Thr kinases that activate their substrates by phosphorylation [B. Stein et al., *Ann. Rep. Med. Chem.*, 31, pp. 289-98 (1996)]. MAPKs are themselves activated by a variety of signals including growth factors, cytokines, UV radiation, and stress-inducing agents.

One particularly interesting MAPK is p38. p38, also known as cytokine suppressive anti-inflammatory drug binding protein (CSBP) and RK, was isolated from murine pre-B cells that were transfected with the lipopolysaccharide (LPS) receptor CD14 and induced with LPS. p38 has since been isolated and sequenced, as has the cDNA encoding it in humans and mouse. Activation of p38 has been observed in cells stimulated by stresses, such as treatment of lipopolysaccharides (LPS), UV, anisomycin, or osmotic shock, and by cytokines, such as IL-1 and TNF.

Inhibition of p38 kinase leads to a blockade on the production of both IL-1 and TNF. IL-1 and TNF stimulate the production of other proinflammatory cytokines such as IL-6 and IL-8 and have been implicated in acute and chronic inflammatory diseases and in post-menopausal osteoporosis [R. B. Kimble et al., *Endocrinol.*, 136, pp. 3054-61 (1995)].

Based upon this finding it is believed that p38, along with other MAPKs, have a role in mediating cellular response to inflammatory stimuli, such as leukocyte accumulation, macrophage/monocyte activation, tissue resorption, fever, acute phase responses and neutrophilia. In addition, MAPKs, such as p38, have been implicated in cancer, thrombin-induced platelet aggregation, immunodeficiency disorders, autoimmune diseases, cell death, allergies, osteoporosis and neurodegenerative disorders. Inhibitors of p38 have also been implicated in the area of pain management through inhibition of prostaglandin endoperoxide synthase-2 induction. Other diseases associated with IL-1, IL-6, IL-8 or TNF overproduction are set forth in WO 96/21654.

Others have already begun trying to develop drugs that specifically inhibit MAPKs. For example, PCT publication WO 95/31451 describes pyrazole compounds that inhibit MAPKs, and in particular p38. However, the efficacy of these inhibitors in vivo is still being investigated.

Accordingly, there is still a great need to develop other potent, p38-specific inhibitors that are useful in treating various conditions associated with p38 activation.

SUMMARY OF THE INVENTION

The present invention solves this problem by providing compounds which demonstrate strong and specific inhibition of p38.

These compounds have the general formula:

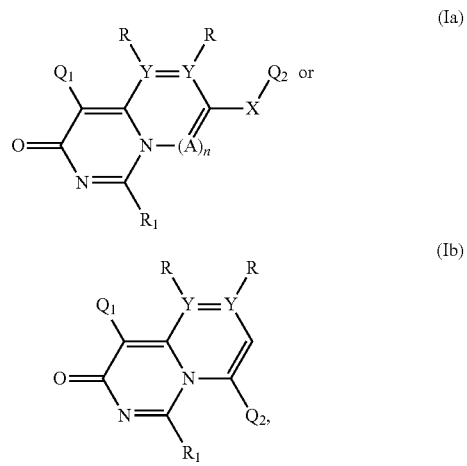

wherein each of $Q_1$ and $Q_2$ are independently selected from 5-6 membered aromatic carbocyclic or heterocyclic ring systems, or 8-10 membered bicyclic ring systems comprising aromatic carbocyclic rings, aromatic heterocyclic rings or a combination of an aromatic carbocyclic ring and an aromatic heterocyclic ring.

The rings that make up $Q_1$ are substituted with 1 to 4 substituents, each of which is independently selected from halo; $C_1$-$C_3$ alkyl optionally substituted with $NR'_2$, $OR'$, $CO_2R'$ or $CONR'_2$; O—($C_1$-$C_3$)-alkyl optionally substituted with $NR'_2$, $OR'$, $CO_2R'$ or $CONR'_2$; $NR'_2$; $OCF_3$; $CF_3$; $NO_2$; $CO_2R'$; $CONHR'$; $SR'$; $S(O_2)N(R')_2$; $SCF_3$; $CN$; $N(R')C(O)R^4$; $N(R')C(O)OR^4$; $N(R')C(O)C(O)R^4$; $N(R')S(O_2)R^4$; $N(R')R^4$; $N(R^4)_2$; $OR^4$; $OC(O)R^4$; $OP(O)_3H_2$; or $N=CH—N(R')_2$.

The rings that make up $Q_2$ are optionally substituted with up to 4 substituents, each of which is independently selected from halo; $C_1$-$C_3$ straight or branched alkyl optionally substituted with $NR'_2$, $OR'$, $CO_2R'$, $S(O_2)N(R')_2$, $N=CH—N(R')_2$, $R^3$, or $CONR'_2$; O—($C_1$-$C_3$)-alkyl; O—($C_1$-$C_3$)-alkyl optionally substituted with $NR'_2$, $OR'$, $CO_2R'$, $S(O_2)N(R')_2$, $N=CH—N(R')_2$, $R^3$, or $CONR'_2$; $NR'_2$; $OCF_3$; $CF_3$; $NO_2$; $CO_2R'$; $CONHR'$; $R^3$; $OR^3$; $NHR^3$; $SR^3$; $C(O)R^3$; $C(O)N(R')R^3$; $C(O)OR^3$; $SR'$; $S(O_2)N(R')_2$; $SCF_3$; $N=CH—N(R')_2$; or $CN$.

R' is selected from hydrogen, $(C_1-C_3)$-alkyl; $(C_2-C_3)$-alkenyl or alkynyl; phenyl or phenyl substituted with 1 to 3 substituents independently selected from halo, methoxy, cyano, nitro, amino, hydroxy, methyl or ethyl.

$R^3$ is selected from 5-6 membered aromatic carbocyclic or heterocyclic ring systems.

$R^4$ is $(C_1-C_4)$-alkyl optionally substituted with $N(R')_2$, OR', $CO_2R'$, $CON(R')_2$, or $SO_2N(R^2)_2$; or a 5-6 membered carbocyclic or heterocyclic ring system optionally substituted with $N(R')_2$, OR', $CO_2R'$, $CON(R')_2$, or $SO_2N(R^2)_2$.

X is selected from —S—, —O—, —S($O_2$)—, —S(O)—, —S($O_2$)—N($R^2$)—, —N($R^2$)—S($O_2$)—, —N($R^2$)—C(O)O—, —O—C(O)—N($R^2$), —C(O)—, —C(O)O—, —O—C(O)—, —C(O)—N($R^2$)—, —N($R^2$)—C(O)—, —N($R^2$)—, —C($R^2$)$_2$—, or —C(O$R^2$)$_2$—.

Each R is independently selected from hydrogen, $-R^2$, $-N(R^2)_2$, $-OR^2$, $SR^2$, $-C(O)-N(R^2)_2$, $-S(O_2)-N(R^2)_2$, or $-C(O)-OR^2$, wherein two adjacent R are optionally bound to one another and, together with each Y to which they are respectively bound, form a 4-8 membered carbocyclic or heterocyclic ring;

$R^2$ is selected from hydrogen, $(C_1-C_3)$-alkyl, or $(C_2-C_3)$-alkenyl; each optionally substituted with —N(R')$_2$, —OR', SR', —C(O)—N(R')$_2$, —S($O_2$)—N(R')$_2$, —C(O)—OR', or $R^3$.

Y is N or C;

A, if present, is N or CR';

n is 0 or 1;

$R_1$ is selected from hydrogen, $(C_1-C_3)$-alkyl, OH, or O—$(C_1-C_3)$-alkyl.

In another embodiment, the invention provides pharmaceutical compositions comprising the p38 inhibitors of this invention. These compositions may be utilized in methods for treating or preventing a variety of disorders, such as cancer, inflammatory diseases, autoimmune diseases, destructive bone disorders, proliferative disorders, infectious diseases, viral diseases and neurodegenerative diseases. These compositions are also useful in methods for preventing cell death and hyperplasia and therefore may be used to treat or prevent reperfusion/ischemia in stroke, heart attacks, organ hypoxia. The compositions are also useful in methods for preventing thrombin-induced platelet aggregation. Each of these above-described methods is also part of the present invention.

DETAILED DESCRIPTION OF THE INVENTION

The present invention provides inhibitors of p38 having the general formula:

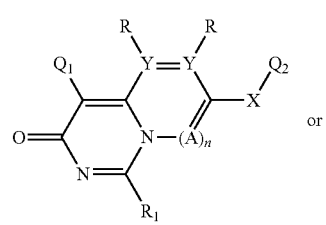

(Ia)

or

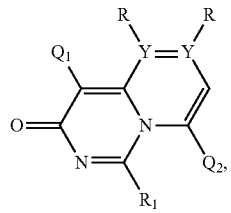

(Ib)

wherein each of $Q_1$ and $Q_2$ are independently selected from 5-6 membered aromatic carbocyclic or heterocyclic ring systems, or 8-10 membered bicyclic ring systems comprising aromatic carbocyclic rings, aromatic heterocyclic rings or a combination of an aromatic carbocyclic ring and an aromatic heterocyclic ring.

The rings that make up $Q_1$ are substituted with 1 to 4 substituents, each of which is independently selected from halo; $C_1-C_3$ alkyl optionally substituted with NR'$_2$, OR', $CO_2R'$ or CONR'$_2$; O—$(C_1-C_3)$-alkyl optionally substituted with NR'$_2$, OR', $CO_2R'$ or CONR'$_2$; NR'$_2$; OCF$_3$; CF$_3$; NO$_2$; $CO_2R'$; CONHR'; SR'; S($O_2$)N(R')$_2$; SCF$_3$; CN; N(R')C(O)$R^4$; N(R')C(O)O$R^4$; N(R')C(O)C(O)$R^4$; N(R')S($O_2$)$R^4$; N(R')$R^4$; N($R^4$)$_2$; O$R^4$; OC(O)$R^4$; OP(O)$_3$H$_2$; or N=CH—N(R')$_2$.

The rings that make up $Q_2$ are optionally substituted with up to 4 substituents, each of which is independently selected from halo; $C_1-C_3$ straight or branched alkyl optionally substituted with NR'$_2$, OR', $CO_2R'$, S($O_2$)N(R')$_2$, N=CH—N(R')$_2$, $R^3$, or CONR'$_2$; O—$(C_1-C_3)$-alkyl; O—$(C_1-C_3)$-alkyl optionally substituted with NR'$_2$, OR', $CO_2R'$, S($O_2$)N(R')$_2$, N=CH—N(R')$_2$, $R^3$, or CONR'$_2$; NR'$_2$; OCF$_3$; CF$_3$; NO$_2$; $CO_2R'$; CONHR'; $R^3$; O$R^3$; NH$R^3$; S$R^3$; C(O)$R^3$; C(O)N(R')$R^3$; C(O)O$R^3$; SR'; S($O_2$)N(R')$_2$; SCF$_3$; N=CH—N(R')$_2$; or CN.

R' is selected from hydrogen, $(C_1-C_3)$-alkyl; $(C_2-C_3)$-alkenyl or alkynyl; phenyl or phenyl substituted with 1 to 3 substituents independently selected from halo, methoxy, cyano, nitro, amino, hydroxy, methyl or ethyl.

$R^3$ is selected from 5-6 membered aromatic carbocyclic or heterocyclic ring systems.

$R^4$ is $(C_1-C_4)$-alkyl optionally substituted with $N(R')_2$, OR', $CO_2R'$, $CON(R')_2$, or $SO_2N(R^2)_2$; or a 5-6 membered carbocyclic or heterocyclic ring system optionally substituted with $N(R')_2$, OR', $CO_2R'$, $CON(R')_2$, or $SO_2N(R^2)_2$.

X is selected from —S—, —O—, —S($O_2$)—, —S(O)—, —S($O_2$)—N($R^2$)—, —N($R^2$)—S($O_2$)—, —N($R^2$)—C(O)O—, —O—C(O)—N($R^2$), —C(O)—, —C(O)O—, —O—C(O)—, —C(O)—N($R^2$)—, —N($R^2$)—C(O)—, —N($R^2$)—, —C($R^2$)$_2$—, or —C(O$R^2$)$_2$—.

Each R is independently selected from hydrogen, $-R^2$, $-N(R^2)_2$, $-OR^2$, $SR^2$, $-C(O)-N(R^2)_2$, $-S(O_2)-N(R^2)_2$, or $-C(O)-OR^2$, wherein two adjacent R are optionally bound to one another and, together with each Y to which they are respectively bound, form a 4-8 membered carbocyclic or heterocyclic ring;

When the two R components form a ring together with the Y components to which they are respectively bound, it will obvious to those skilled in the art that a terminal hydrogen from each unfused R component will be lost. For example, if a ring structure is formed by binding those two R components together, one being —NH—CH$_3$ and the other being —CH$_2$—CH$_3$, one terminal hydrogen on each R component (indicated in bold) will be lost. Therefore, the resulting portion of the ring structure will have the formula —NH—CH$_2$—CH$_2$—CH$_2$—.

$R^2$ is selected from hydrogen, $(C_1-C_3)$-alkyl, or $(C_2-C_3)$-alkenyl; each optionally substituted with —N(R')$_2$, —OR', SR', —C(O)—N(R')$_2$, —S(O$_2$)—N(R')$_2$, —C(O)—OR', or $R^3$.

Y is N or C;

A, if present, is N or CR';

n is 0 or 1;

$R_1$ is selected from hydrogen, $(C_1-C_3)$-alkyl, OH, or O—$(C_1-C_3)$-alkyl. It will be apparent to those of skill in the art that if $R_1$ is OH, the resulting inhibitor may tautomerize resulting in compounds of the formula:

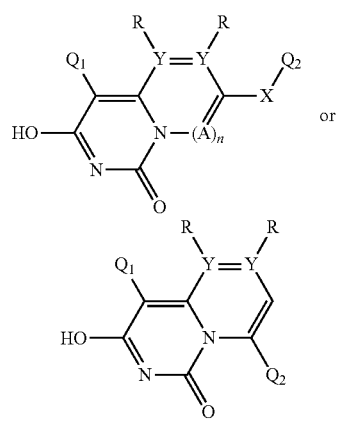

which are also p38 inhibitors of this invention.

According to another preferred embodiment, $Q_1$ is selected from phenyl or pyridyl containing 1 to 3 substituents, wherein at least one of said substituents is in the ortho position and said substituents are independently selected from chloro, fluoro, bromo, —CH$_3$, —OCH$_3$, —OH, —CF$_3$, —OCF$_3$, —O(CH$_2$)$_2$CH$_3$, NH$_2$, 3,4-methylenedioxy, —N(CH$_3$)$_2$, —NH—S(O)$_2$-phenyl, —NH—C(O)O—CH$_2$-4-pyridine, —NH—C(O)CH$_2$-morpholine, —NH—C(O)CH$_2$—N(CH$_3$)$_2$, —NH—C(O)CH$_2$-piperazine, —NH—C(O)CH$_2$-pyrrolidine, —NH—C(O)C(O)-morpholine, —NH—C(O)C(O)-piperazine, —NH—C(O)C(O)-pyrrolidine, —O—C(O)CH$_2$—N(CH$_3$)$_2$, or —O—(CH$_2$)$_2$—N(CH$_3$)$_2$.

Even more preferred are phenyl or pyridyl containing at least 2 of the above-indicated substituents both being in the ortho position.

Some specific examples of preferred $Q_1$ are:

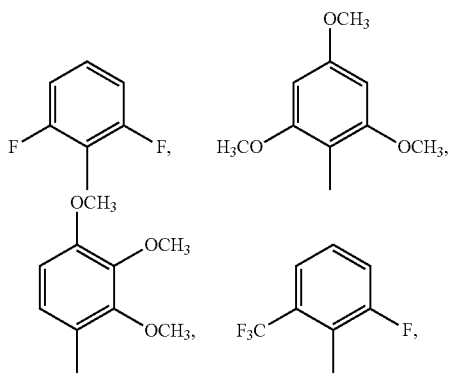

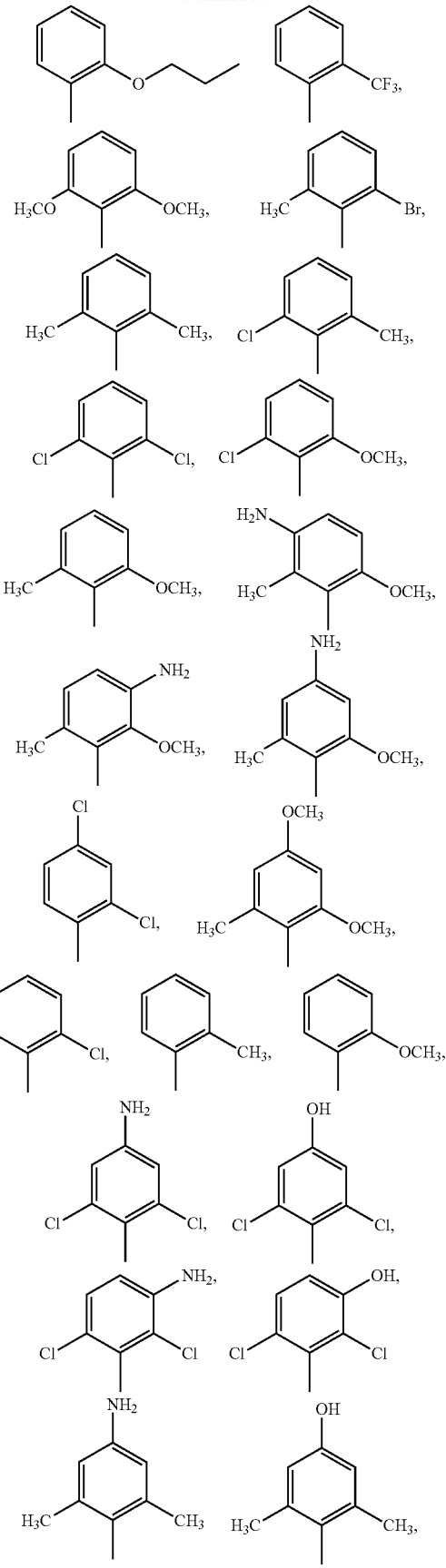

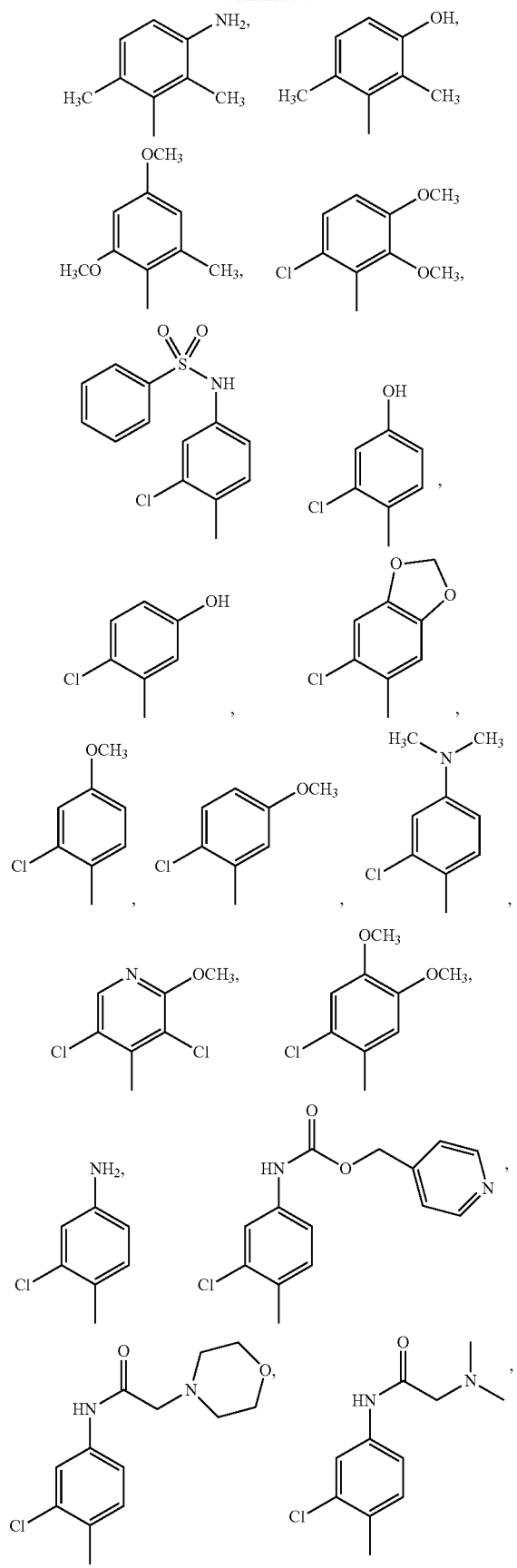
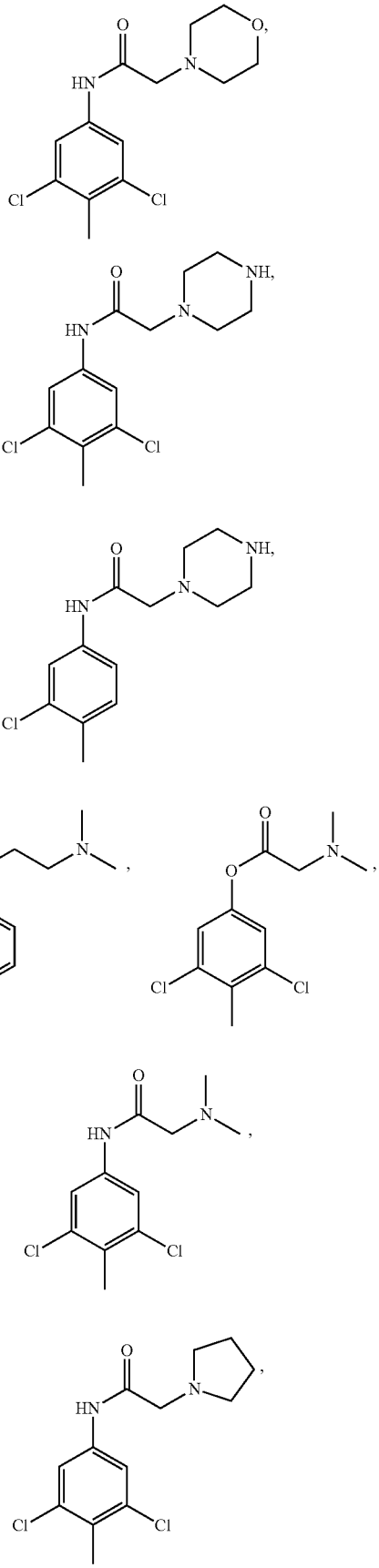

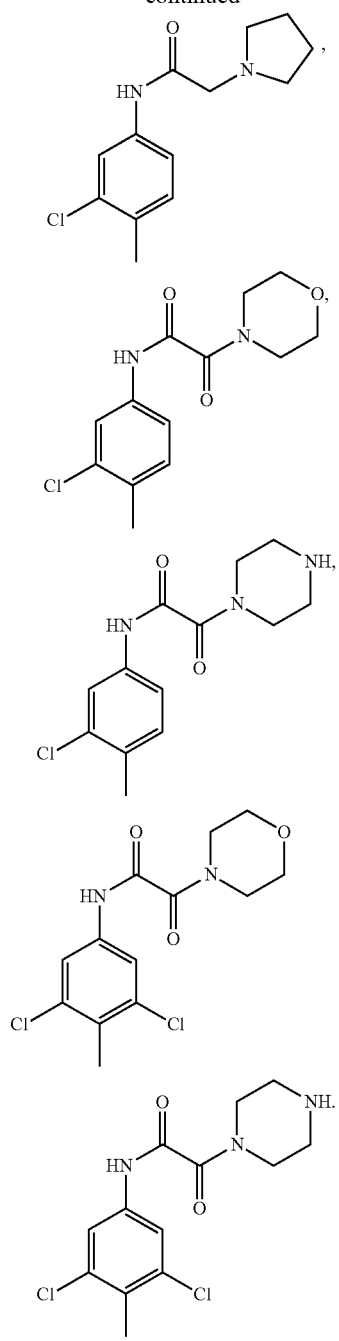

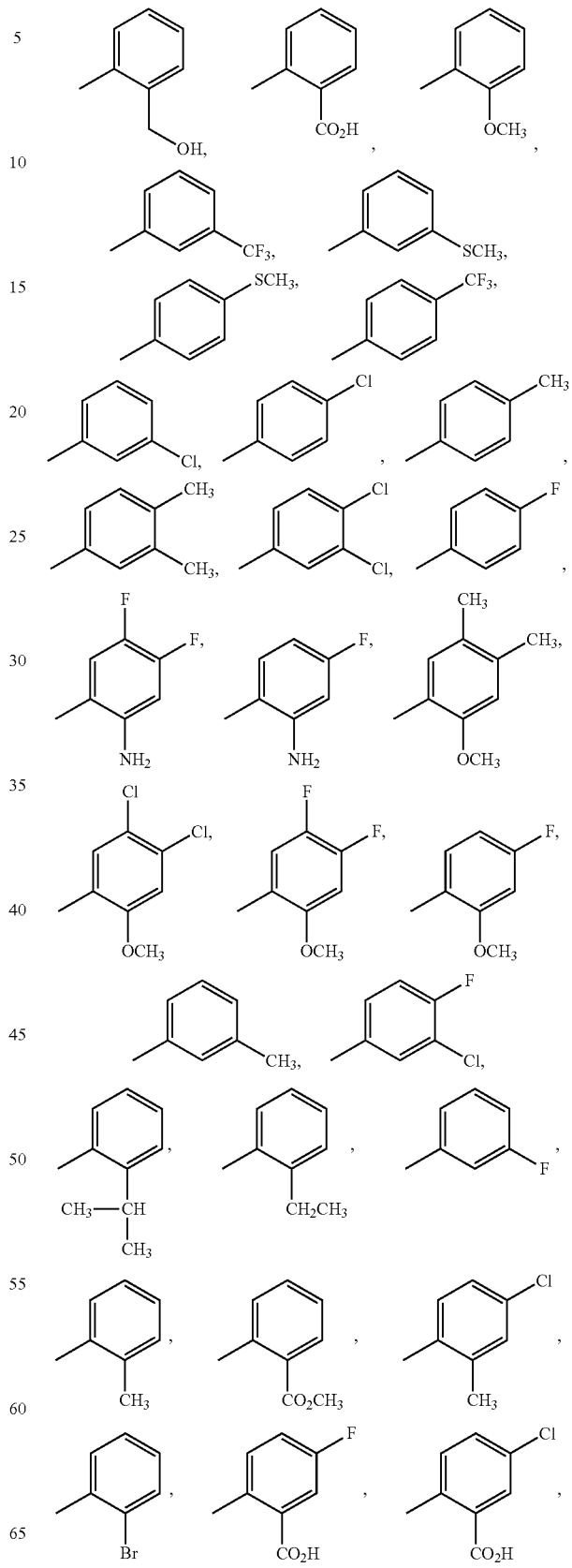

Some specific examples of preferred $Q_2$ are:

Most preferably, $Q_1$ is selected from 2-fluoro-6-trifluoromethylphenyl, 2,6-difluorophenyl, 2,6-dichlorophenyl, 2-chloro-4-hydroxyphenyl, 2-chloro-4-aminophenyl, 2,6-dichloro-4-aminophenyl, 2,6-dichloro-3-aminophenyl, 2,6-dimethyl-4-hydroxyphenyl, 2-methoxy-3,5-dichloro-4-pyridyl, 2-chloro-4,5 methylenedioxy phenyl, or 2-chloro-4-(N-2-morpholino-acetamido)phenyl.

According to a preferred embodiment, $Q_2$ is phenyl or pyridyl containing 0 to 3 substituents, wherein each substituent is independently selected from chloro, fluoro, bromo, methyl, ethyl, isopropyl, —$OCH_3$, —OH, —$NH_2$, —$CF_3$, —$OCF_3$, —$SCH_3$, —C(O)OH, —C(O)$OCH_3$, —$CH_2NH_2$, —N($CH_2$)$_2$, —$CH_2$-pyrrolidine and —$CH_2OH$.

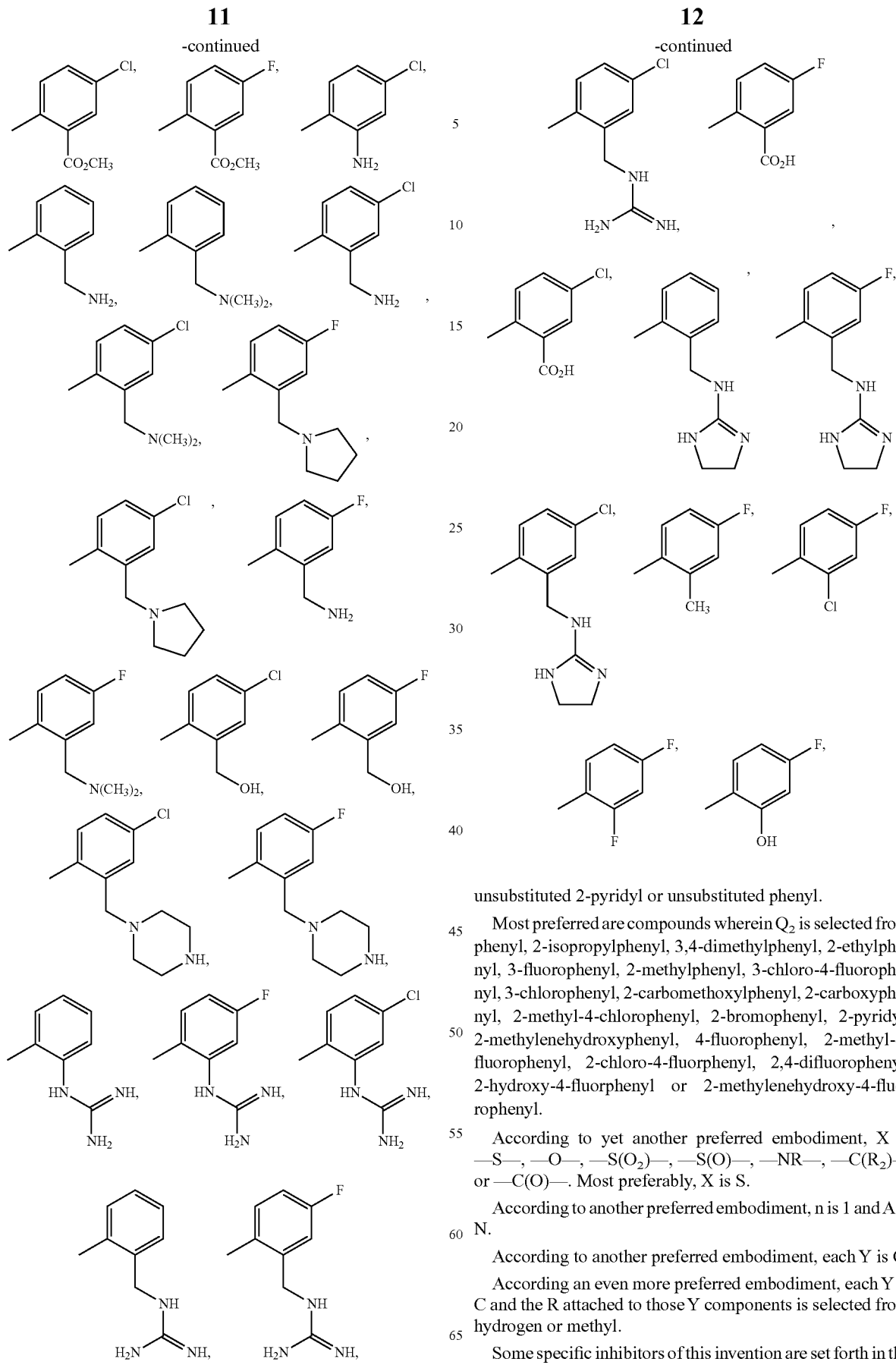

unsubstituted 2-pyridyl or unsubstituted phenyl.

Most preferred are compounds wherein $Q_2$ is selected from phenyl, 2-isopropylphenyl, 3,4-dimethylphenyl, 2-ethylphenyl, 3-fluorophenyl, 2-methylphenyl, 3-chloro-4-fluorophenyl, 3-chlorophenyl, 2-carbomethoxylphenyl, 2-carboxyphenyl, 2-methyl-4-chlorophenyl, 2-bromophenyl, 2-pyridyl, 2-methylenehydroxyphenyl, 4-fluorophenyl, 2-methyl-4-fluorophenyl, 2-chloro-4-fluorphenyl, 2,4-difluorophenyl, 2-hydroxy-4-fluorphenyl or 2-methylenehydroxy-4-fluorophenyl.

According to yet another preferred embodiment, X is —S—, —O—, —S(O$_2$)—, —S(O)—, —NR—, —C(R$_2$)— or —C(O)—. Most preferably, X is S.

According to another preferred embodiment, n is 1 and A is N.

According to another preferred embodiment, each Y is C.

According an even more preferred embodiment, each Y is C and the R attached to those Y components is selected from hydrogen or methyl.

Some specific inhibitors of this invention are set forth in the table below.

TABLE 1

Formula Ia and Ib Compounds.

| cpd # | structure |
|---|---|
| 2 | (4-fluorophenyl) substituted structure |
| 3 | (2,4-dichlorophenyl) substituted structure |
| 5 | (2,4-dichlorophenyl with p-tolylthio) substituted structure |
| 6 | (2,6-dichlorophenyl) substituted structure |
| 7 | (2-chlorophenyl) substituted structure |

TABLE 1-continued

Formula Ia and Ib Compounds.

| cpd # | structure |
|---|---|
| 9 | (3,4-dichlorophenyl) substituted structure |
| 10 | (4-methoxyphenyl) substituted structure |
| 11 | (2-methoxyphenyl) substituted structure |
| 12 | (2,6-dichlorophenyl with 4-fluorophenylthio) substituted structure |
| 13 | (2,6-dichlorophenyl with dimethyl) substituted structure |

TABLE 1-continued
Formula Ia and Ib Compounds.
| cpd # | structure |
|---|---|
| 8 | 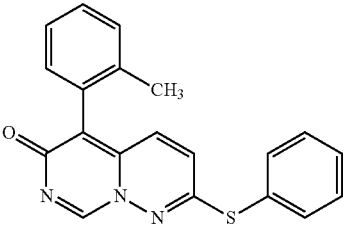 |
| 15 | 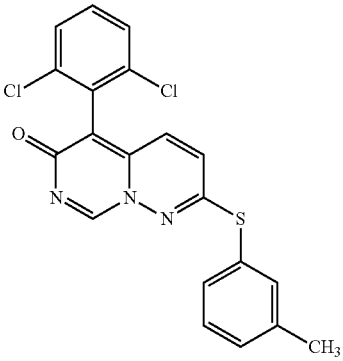 |
| 16 | 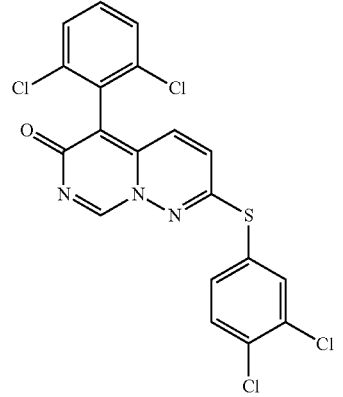 |
| 17 | 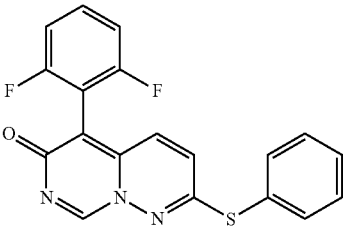 |
TABLE 1-continued
Formula Ia and Ib Compounds.
| cpd # | structure |
|---|---|
| 14 | 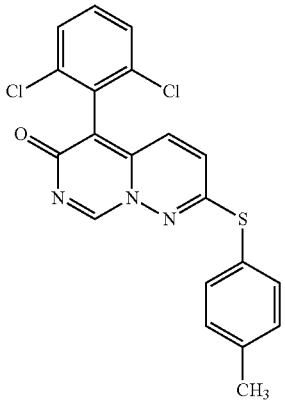 |
| 21 | 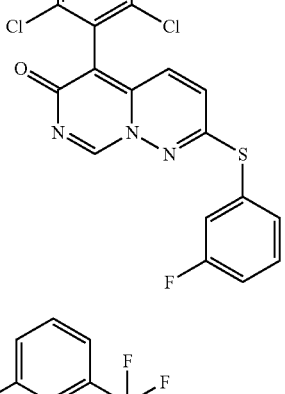 |
| 22 | 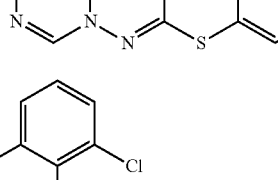 |
| 23 | 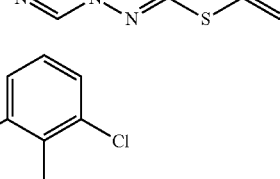 |
| 18 | 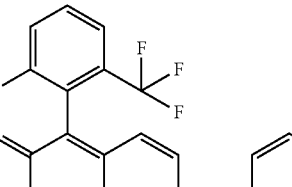 |

TABLE 1-continued

Formula Ia and Ib Compounds.

| cpd # | structure |
|---|---|
| 19 | (structure) |
| 20 | (structure) |
| 27 | (structure) |
| 24 | (structure) |
| 25 | (structure) |
| 26 | (structure) |
| 33 | (structure) |
| 28 | (structure) |
| 29 | (structure) |

TABLE 1-continued

Formula Ia and Ib Compounds.

| cpd # | structure |
|---|---|
| 30 | (2,6-dichlorophenyl)-pyrido[2-ylthio] substituted pyrimido-pyridazinone |
| 31 | (2,6-dichlorophenyl)-[2-(N,N-dimethylcarbamoyl)phenylthio] substituted pyrimido-pyridazinone |
| 32 | (2,6-dichlorophenyl)-(2,4-dimethylphenylthio) substituted pyrimido-pyridazinone |
| 34 | (2,6-dichlorophenyl)-(4-fluoro-2-nitrophenylthio) substituted pyrimido-pyridazinone |
| 35 | (2,6-dichlorophenyl)-(2-amino-4-fluorophenylthio) substituted pyrimido-pyridazinone |
| 36 | (2-chloro-3,4-dimethoxyphenyl)-(4-fluorophenylthio) substituted pyrimido-pyridazinone |
| 37 | (3-amino-2,6-dichlorophenyl)-(4-fluorophenylthio) substituted pyrimido-pyridazinone |
| 38 | (2,6-dichlorophenyl)-(2-chloro-4-fluorophenylthio) substituted pyrimido-pyridazinone |
| 39 | (6-chloro-benzo[1,3]dioxol-5-yl)-(4-fluorophenylthio) substituted pyrimido-pyridazinone |

TABLE 1-continued
Formula Ia and Ib Compounds.
| cpd # | structure |
|---|---|
| 40 | 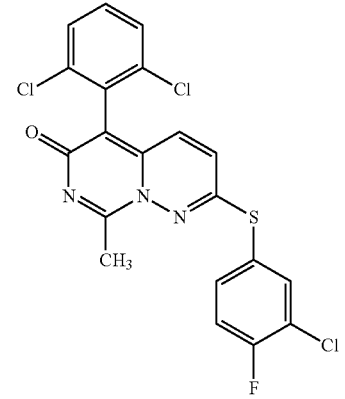 |
| 41 | 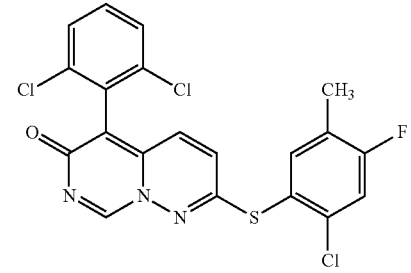 |
| 42 | 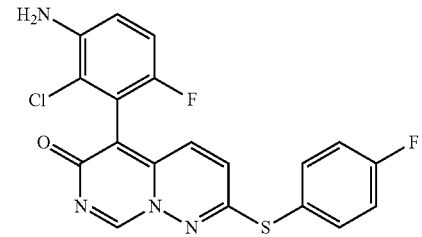 |
| 45 | 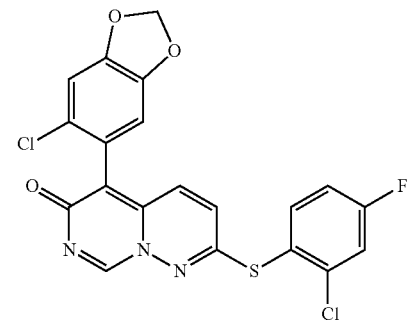 |
| 46 | 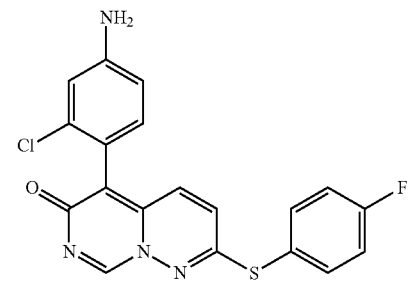 |
| 47 | 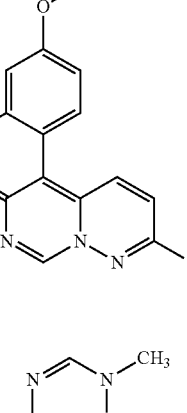 |
| 48 | 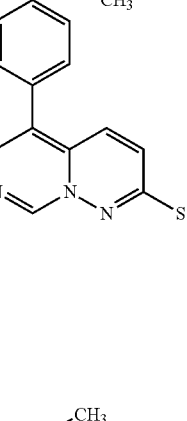 |
| 43 | 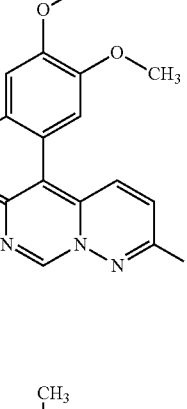 |
| 44 | 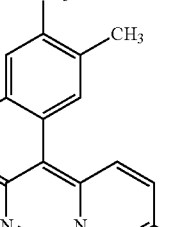 |

TABLE 1-continued

Formula Ia and Ib Compounds.

| cpd # | structure |
|---|---|
| 51 | 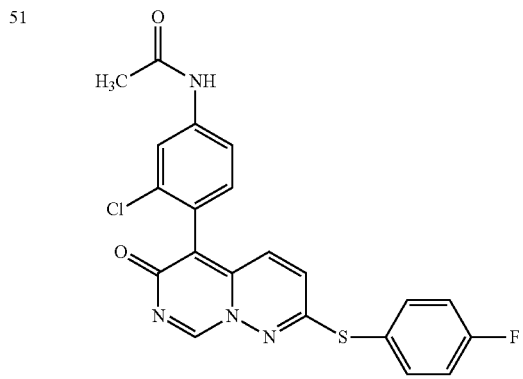 |
| 52 | 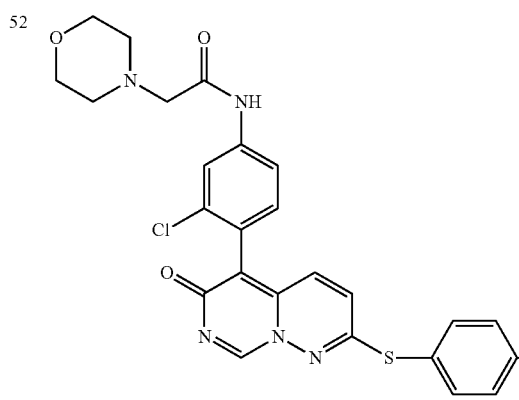 |
| 49 | 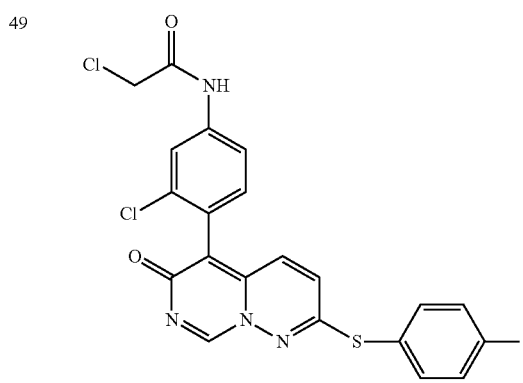 |
| 50 | 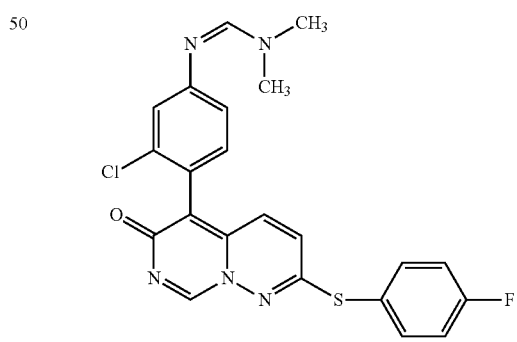 |

TABLE 1-continued

Formula Ia and Ib Compounds.

| cpd # | structure |
|---|---|
| 53 | 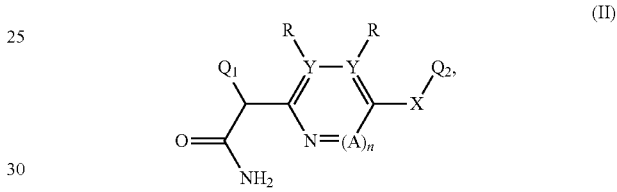 |

According to another embodiment, the present invention provides methods of producing inhibitors of p38 of the formula (Ia) depicted above. These methods involve reacting a compound of formula II:

(II)

wherein each of the variables in the above formula are the same as defined above for the inhibitors of this invention, with a leaving group reagent of formula IIa:

(IIa)

$$L_1 \overset{R'}{\underset{L_2}{-}} L_3,$$

wherein R' is as defined above, or a leaving group reagent of formula IIb:

(IIb)

wherein each of $L_1$, $L_2$, and $L_3$ independently represents a leaving group.

The leaving group reagent used in this reaction is added in excess, either neat or with a co-solvent, such as toluene. The reaction is carried out at a temperature of between 25° C. and 150° C.

Leaving group reagents of formula IIa that are useful in producing the p38 inhibitors of this invention include dimethylformamide dimethylacetal, dimethylacetamide dimethylacetal, trimethyl orthoformate, dimethylformamide diethylacetal and other related reagents. Preferably the leaving group reagent of formula IIa used to produce the inhibitors of this invention is dimethylformamide dimethylacetal.

Leaving group reagents of formula IIb that are useful in producing the p38 inhibitors of this invention include phosgene, carbonyldiimidazole, diethyl carbonate and triphosgene.

More preferred methods of producing the compounds of this invention utilize compounds of formula II wherein each of the variables are defined in terms of the more preferred and most preferred choices as set forth above for the compounds of this invention.

Because the source of $R_1$ is the leaving group reagent (C—R' or C=O), its identity is, of course, dependent on the structure of that reagent. Therefore, in compounds where $R_1$ is OH, the reagent used must be IIb. Similarly, when $R_1$ is H or $(C_1-C_3)$-alkyl, the reagent used must be IIa. In order to generate inhibitors wherein $R_1$ is O—$(C_1-C_3)$-alkyl, a compound wherein $R_1$ is OH is first generated, followed by alkylation of that hydroxy by standard techniques, such as treatment with Na hydride in DMF, methyl iodide and ethyl iodide.

The immediate precursors to the inhibitors of this invention of formula Ia (i.e., compounds of Formula II) may themselves be synthesized by either of the synthesis schemes depicted below:

In Scheme 1, the order of steps 1) and 2) can be reversed. Also, the starting nitrile may be replaced by a corresponding acid or by an ester. Alternatively, other well-known latent carboxyl or carboxamide moieties may be used in place of the nitrile (see scheme 2). Variations such as carboxylic acids, carboxylic esters, oxazolines or oxizolidinones may be incorporated into this scheme by utilizing subsequent deprotection and functionalization methods which are well known in the art The base used in the first step of Scheme 1 (and in Scheme 2, below) is selected from sodium hydride, sodium amide, LDA, lithium hexamethyldisilazide, sodium hexamethyldisilazide or any number of other non-nucleophilic bases that will deprotonate the position alpha to the nitrile.

SCHEME 1

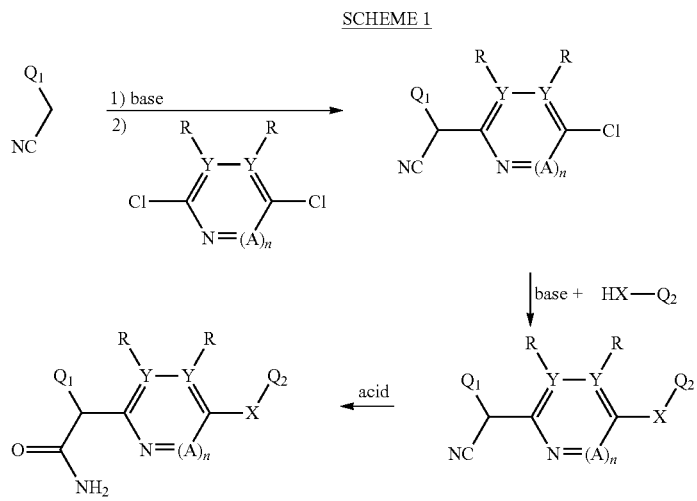

Also, the addition of HX-$Q_2$ in the single step depicted above may be substituted by two steps—the addition of a protected or unprotected X derivative followed by the addition of a $Q_2$ derivative in a subsequent step.

SCHEME 2

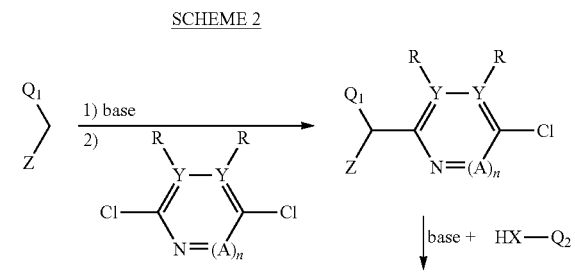

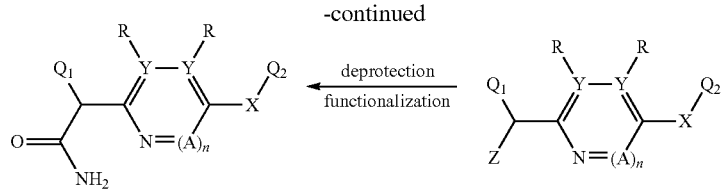

In Scheme 2, Z is selected from COOH, COOR', CON(R')$_2$, oxazoline, oxazolidinone or CN. R' is as defined above.

According to another embodiment, the present invention provides methods of producing inhibitors of p38 of the formula (Ib) depicted above. These methods involve reacting a compound of formula III:

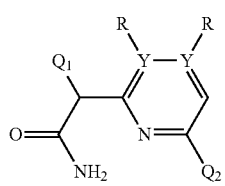

(III)

wherein each of the variables in the above formula are the same as defined above for the inhibitors of this invention, with a leaving group reagent of formula:

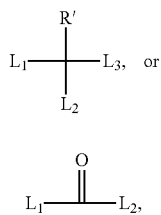

(IIa)

(IIb)

as described above.

Two full synthesis schemes for the p38 inhibitors of formula (Ib) of this invention are depicted below.

SCHEME 3

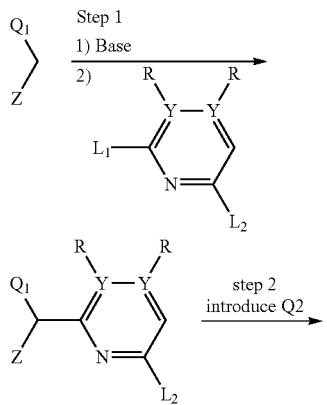

In scheme 3, a $Q_1$ substituted derivative may be treated with a base such as sodium hydride, sodium amide, LDA, lithium hexamethyldisilazide, sodium hexamethyldisilazide or any number of other non-nucleophilic bases to deprotonate the position alpha to the Z group, which represents a masked amide moiety. Alternatively, Z is a carboxylic acid, carboxylic ester, oxazoline or oxazolidinone. The anion resulting from deprotonation is then contacted with a nitrogen bearing heterocyclic compound which contains two leaving groups, or latent leaving groups, in the presence of a Palladium catalyst. One example of such compound may be 2,6-dichloropyridine.

In step two, the $Q_2$ ring moiety is introduced. This may be performed utilizing many reactions well known in the art which result in the production of biaryl compounds. One example may be the reaction of an aryl lithium compound with the pyridine intermediate produced in step 1. Alternatively, an arylmetallic compound such as an aryl stannane or an aryl boronic acid may be reacted with the aryl halide portion of the pyridine intermediate in the presence of a Pd° catalyst.

In step 3 the Z group is deprotected and/or functionalized to form the amide compound. When Z is a carboxylic acid, carboxylic ester, oxazoline or oxazolidinone, variations in deprotection and functionalization methods which are well known in the art are employed to produce the amide. Finally in step 4, the amide compound is cyclized to the final product utilizing reagents such as DMF acetal or similar reagents either neat or in an organic solvent.

SCHEME 4

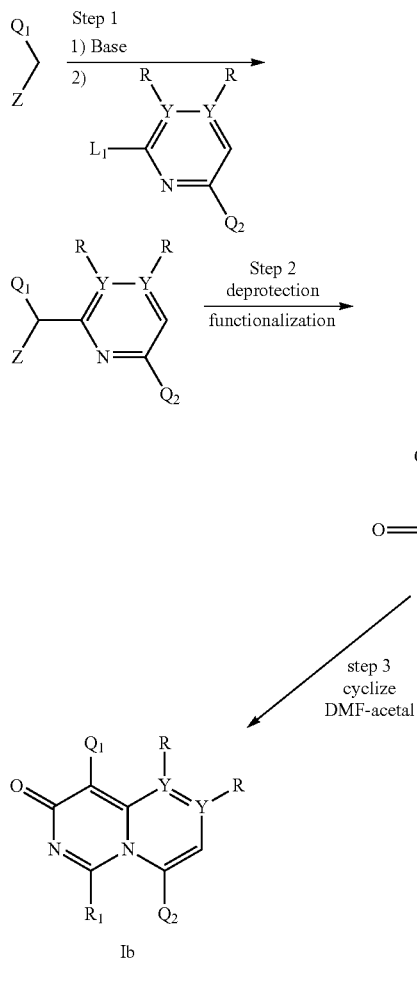

Scheme 4 is similar except that the a biaryl intermediate is first generated prior to reaction with the Q1 starting material.

According to another embodiment, the invention provides inhibitors of p38 similar to those of formulae Ia and Ib above, but wherein the C=N in the ring bearing the $Q_1$ substituent is reduced. These inhibitors have the formula:

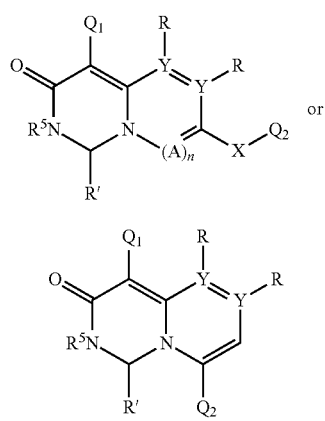

wherein A, $Q_1$, $Q_2$, R, R', X, Y and n are defined in the same manner as set forth for compounds of formulae Ia and Ib. These definitions hold for all embodiments of each of these variables (i.e., basic, preferred, more preferred and most preferred). $R^5$ is selected from hydrogen, $-CR'_2OH$, $-C(O)R^4$, $-C(O)OR^4$, $-CR'_2OPO_3H_2$, $-PO_3H_2$, and salts of $-PO_3H_2$.

When $R^5$ is not hydrogen, the resulting compounds are expected to be prodrug forms which should be cleaved in vivo to produce a compound wherein $R^5$ is hydrogen.

According to other preferred embodiments, in compounds of formula Ic, A is preferably nitrogen, n is preferably 1, and X is preferably sulfur. In compounds of formula Ic or Id, $Q_1$ and $Q_2$ are preferably the same moieties indicated above for those variables in compounds of formulae Ia and Ib.

Compounds of formulae Ic and Id may be prepared directly from compounds of formulae Ia or Ib which contain a hydrogen, $C_1$-$C_3$ alkyl or $C_2$-$C_3$ alkenyl or alkynyl at the $R_1$ position (e.g., where $R_1$=R'). The synthesis schemes for these compounds is depicted in Schemes 5 and 6, below.

SCHEME 5

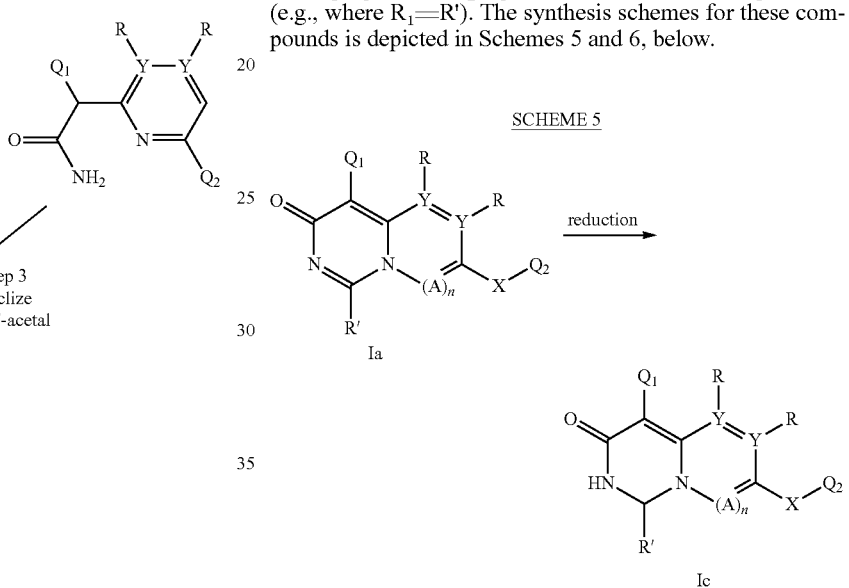

SCHEME 6

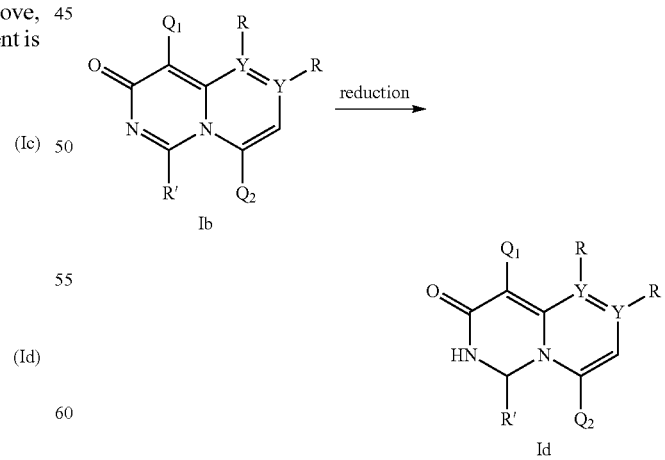

In these schemes, compounds of formula Ia or Ib are reduced by reaction with an excess of diisobutylaluminum hydride, or equivalent reagent to yield the ring reduced compounds of formula Ic or Id, respectively.

The addition of an R⁵ component other than hydrogen onto the ring nitrogen is achieved by reacting the formula Ic or Id compounds indicated above with the appropriate reagent(s). Examples of such modifications are provided in the Example section below.

Some specific inhibitors of this invention of formula Ic are set forth in the table below.

TABLE 2

Formula Ic Compounds.

| cpd # | structure |
|---|---|
| 101 | 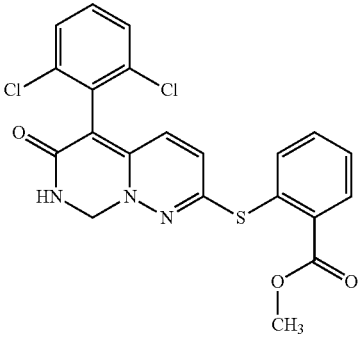 |
| 102 | 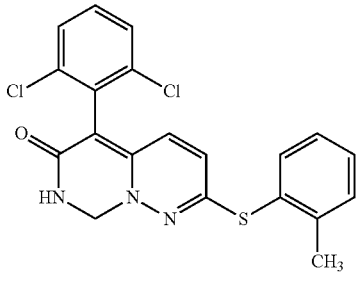 |
| 103 | 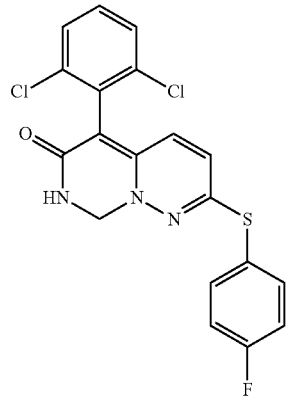 |
| 104 | 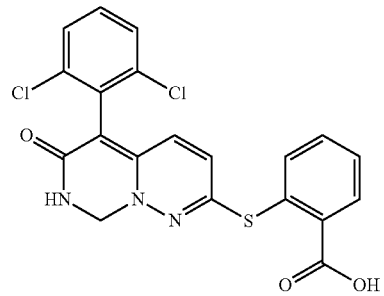 |

TABLE 2-continued

Formula Ic Compounds.

| cpd # | structure |
|---|---|
| 110 | 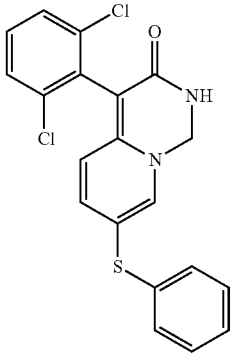 |
| 111 | 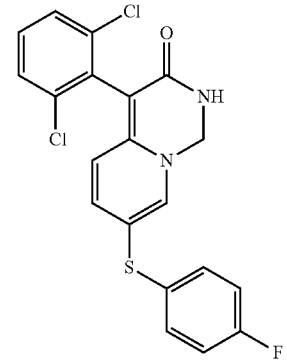 |
| 112 | 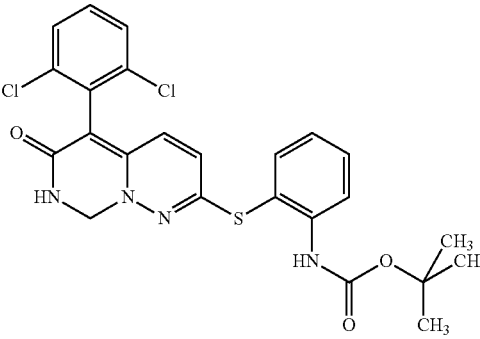 |
| 113 | 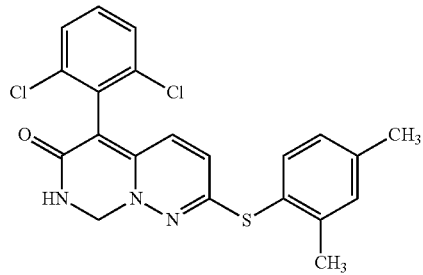 |

TABLE 2-continued

Formula Ic Compounds.

| cpd # | structure |
|---|---|
| 105 | (structure) |
| 106 | (structure) |
| 107 | (structure) |
| 108 | (structure) |
| 109 | (structure) |
| 114 | (structure) |
| 115 | (structure) |
| 116 | (structure) |
| 117 | (structure) |
| 118 | (structure) |

TABLE 2-continued

Formula Ic Compounds.

| cpd # | structure |
|---|---|
| 119 | |
| 120 | |
| 121 | |
| 122 | |
| 123 | 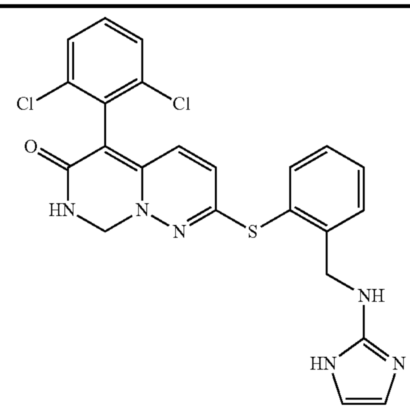 |
| 128 | 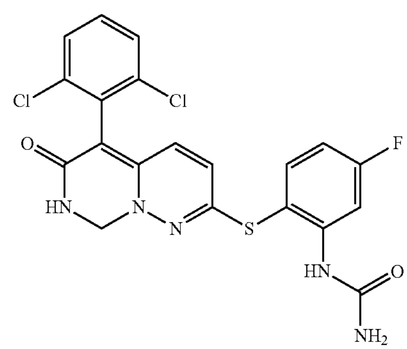 |
| 129 | 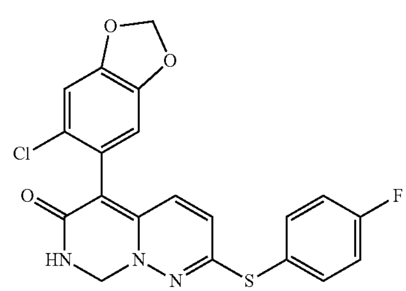 |
| 130 | 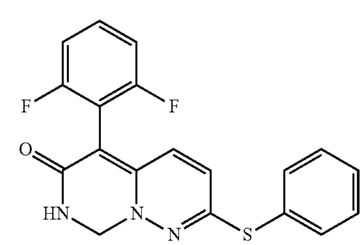 |
| 131 | 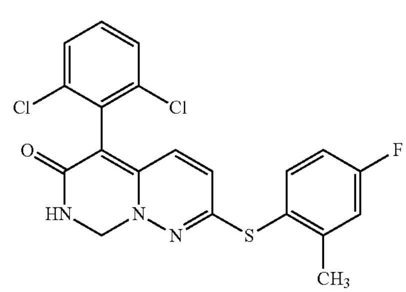 |

TABLE 2-continued
Formula Ic Compounds.
| cpd # | structure |
|---|---|
| 132 | 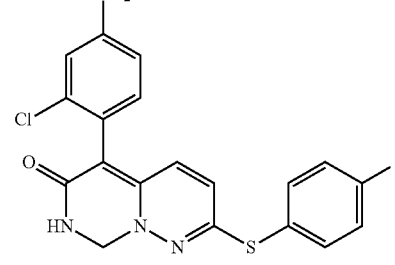 |
| 124 | 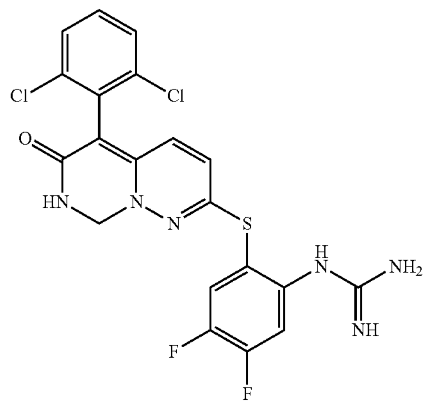 |
| 125 | 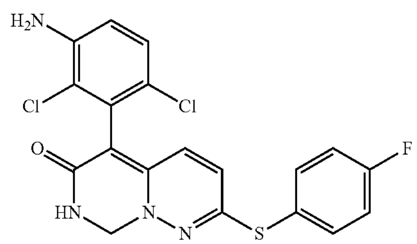 |
| 126 | 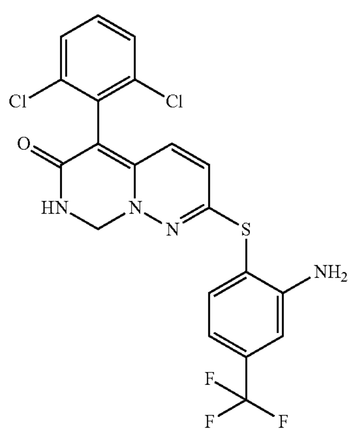 |
| 127 | 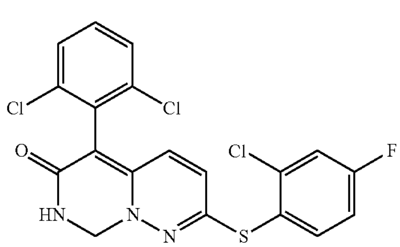 |
TABLE 2-continued
Formula Ic Compounds.
| cpd # | structure |
|---|---|
| 137 | 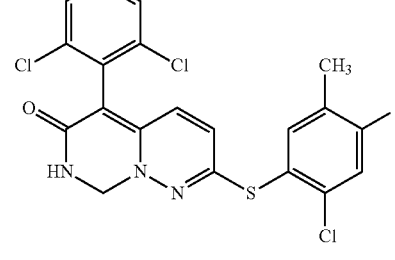 |
| 133 | 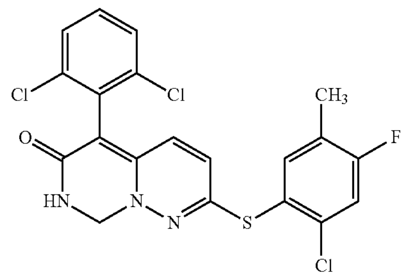 |
| 134 | 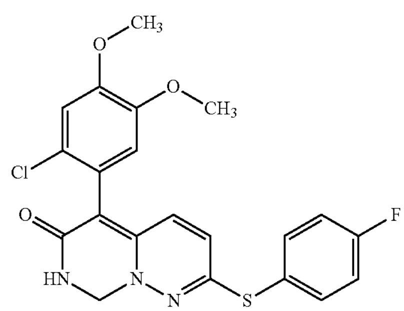 |
| 135 | 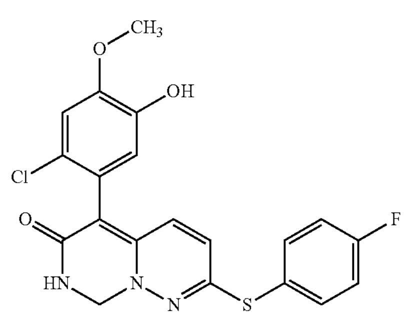 |
| 136 | 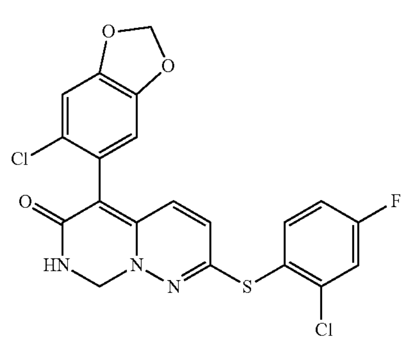 |

TABLE 2-continued

Formula Ic Compounds.

| cpd # | structure |
|---|---|
| 142 | 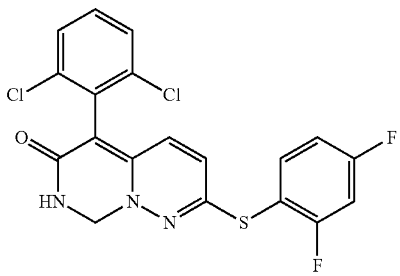 |
| 138 | 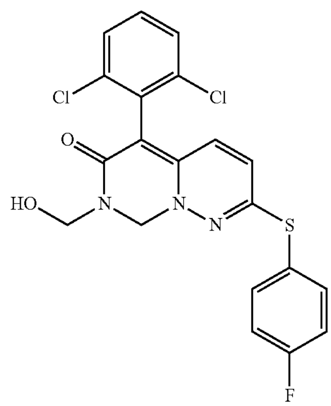 |
| 139 | 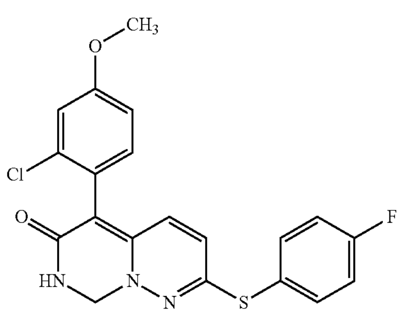 |
| 140 | 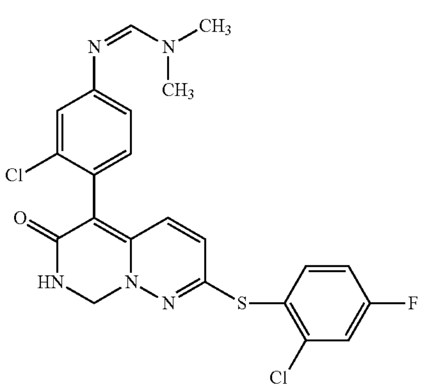 |

TABLE 2-continued

Formula Ic Compounds.

| cpd # | structure |
|---|---|
| 141 | |
| 143 | |
| 144 | |
| 145 | |

According to yet another embodiment, the invention provides p38 inhibitors of the formulae:

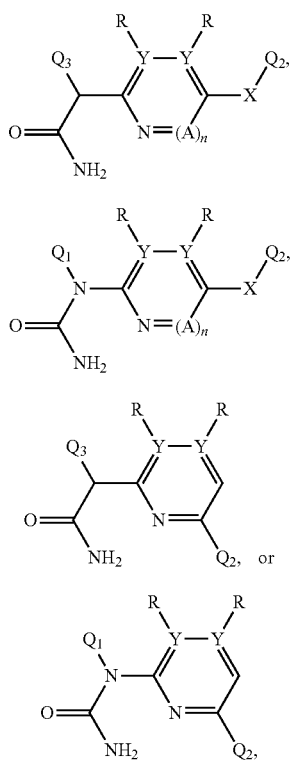

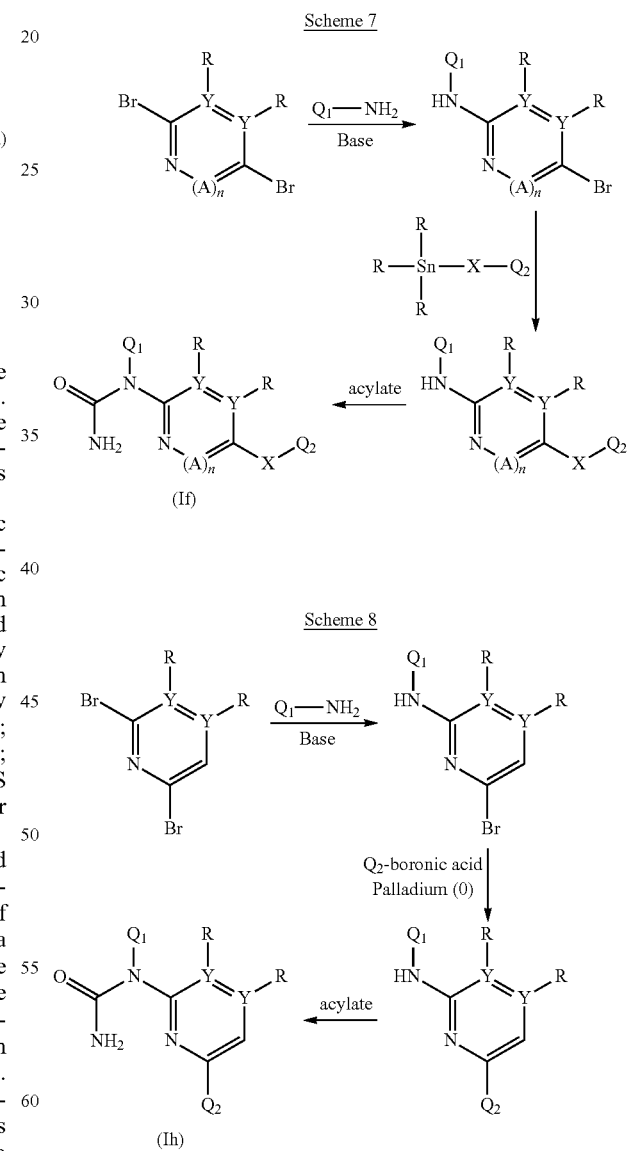

wherein A, $Q_1$, $Q_2$, R, X, Y and n are defined in the same manner as set forth for compounds of formulae Ia and Ib. These definitions hold for all embodiments of each of these variables (i.e., basic, preferred, more preferred and most preferred). More preferably, in compounds of formula Ie, $Q_2$ is unsubstituted phenyl.

$Q_3$ is a 5-6 membered aromatic carbocyclic or heterocyclic ring system, or an 8-10 membered bicyclic ring system comprising aromatic carbocyclic rings, aromatic heterocyclic rings or a combination of an aromatic carbocyclic ring and an aromatic heterocyclic ring. The rings of $Q_3$ are substituted with 1 to 4 substituents, each of which is independently selected from halo; $C_1$-$C_3$ alkyl optionally substituted with $NR'_2$, $OR'$, $CO_2R'$ or $CONR'_2$; $O$—$(C_1$-$C_3)$-alkyl optionally substituted with $NR'_2$, $OR'$, $CO_2R'$ or $CONR'_2$; $NR'_2$; $OCF_3$; $CF_3$; $NO_2$; $CO_2R'$; $CONHR'$; $SR'$; $S(O_2)N(R')_2$; $SCF_3$; $CN$; $N(R')C(O)R^4$; $N(R')C(O)OR^4$; $N(R')C(O)C(O)R^4$; $N(R')S(O_2)R^4$; $N(R')R^4$; $N(R^4)_2$; $OR^4$; $OC(O)R^4$; $OP(O)_2H_2$; or $N$=$CH$—$N(R')_2$.

According to one preferred embodiment, $Q_3$ is substituted with 2 to 4 substituents, wherein at least one of said substituents is present in the ortho position relative to the point of attachment of $Q_3$ to the rest of the inhibitor. When $Q_3$ is a bicyclic ring, the 2 substituents in the ortho position are present on the ring that is closest (i.e., directly attached) to the rest of the inhibitor molecule. The other two optional substituents may be present on either ring. More preferably, both such ortho positions are occupied by one of said substituents.

According to another preferred embodiment, $Q_3$ is a monocyclic carbocyclic ring, wherein each ortho substituent is independently selected from halo or methyl. According to another preferred embodiment, $Q_3$ contains 1 or 2 additional substituents independently selected from $NR'_2$, $OR'$, $CO_2R'$ $CN$, $N(R')C(O)R^4$; $N(R')$ $C(O)OR^4$; $N(R')$ $C(O)C(O)R^4$; $N(R')$ $S(O_2)R^4$; $N(R')$ $R^4$; $N(R^4)_2$; $OR^4$; $OC(O)R^4$; $OP(O)_3H_2$; or $N$=$CH$—$N(R')_2$.

Preferably, $Q_3$ is selected from any of the $Q_3$ moieties present in the Ie compounds set forth in Table 3, below, or from any of the $Q_3$ moieties present in the Ig compounds set forth in Table 4, below.

Those of skill will recognize compounds of formula Ie as being the direct precursors to certain of the formula Ia and formula Ic p38 inhibitors of this invention (i.e., those wherein $Q_1$=$Q_3$). Those of skill will also recognize that compounds of formula Ig are precursors to certain of the formula Ib and Id p38 inhibitors of this invention (i.e., those wherein $Q_1$=Q3). Accordingly, the synthesis of formula Ie inhibitors is depicted above in Schemes 1 and 2, wherein $Q_1$ is replaced by $Q_3$. Similarly, the synthesis of formula Ig inhibitors is depicted above in Schemes 3 and 4, wherein $Q_1$ is replaced by $Q_3$.

The synthesis of formula If and formula Ih inhibitors is depicted below in Schemes 7 and 8.

Scheme 8 depicts the synthesis of compounds of type Ih. For example, treating an initial dibromo derivative, such as 2,6 dibromopyridine, with an amine in the presence of a base such as sodium hydride yields the 2-amino-6-bromo derivative. Treatment of this intermediate with a phenylboronic acid analog (a Q2-boronic acid) such as phenyl boronic acid in the presence of a palladium catalyst gives the disubstituted derivative which can then be acylated to the final product. The order of the first two steps of this synthesis may be reversed.

Without being bound by theory, applicants believe that the diortho substitution in the Q₃ ring of formula Ie and Ig inhibitors and the presence of a nitrogen directly attached to the Q₁ ring in formula If and Ih inhibitors causes a "flattening" of the compound that allows it to effectively inhibit p38.

A preferred formula Ie inhibitor of this invention is one wherein A is carbon, n is 1, X is sulfur, each Y is carbon, each R is hydrogen, Q₃ is 2,6-dichlorophenyl and Q₂ is phenyl, said compound being referred to as compound 201. A preferred formula Ig inhibitor of this invention is one wherein Q₃ is 2,6-dichlorophenyl, Q₂ is phenyl, each Y is carbon and each R is hydrogen. This compound is referred to herein as compound 202. Other preferred formula Ig compounds of this invention are those listed in Table 4, below.

Preferred Ih compounds of this invention are those depicted in Table 5, below. Other preferred Ih compounds are those wherein Q₁ is phenyl independently substituted at the 2 and 6 positions by chloro or fluoro; each Y is carbon; each R is hydrogen; and Q₂ is 2-methylphenyl, 4-fluorophenyl, 2,4-difluorophenyl, 2 methylenehydroxy-4-fluorophenyl, or 2-methyl-4-fluorophenyl.

Some specific inhibitors of formulae Ie, Ig and Ih are depicted in the tables below.

TABLE 3

Formula Ie Inhibitors.

| cmpd # | structure |
|---|---|
| 201 | 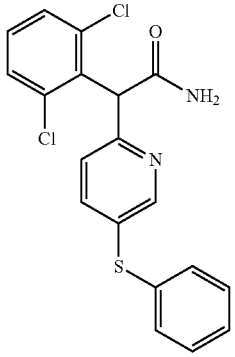 |
| 203 | 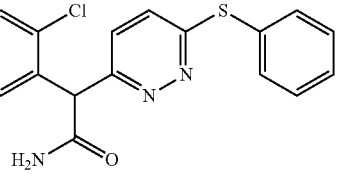 |
| 204 | 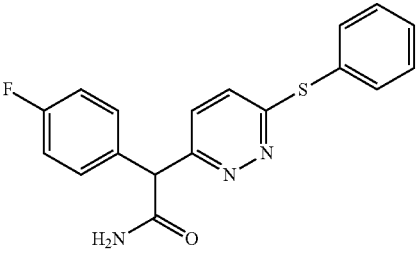 |

TABLE 3-continued

Formula Ie Inhibitors.

| cmpd # | structure |
|---|---|
| 205 | 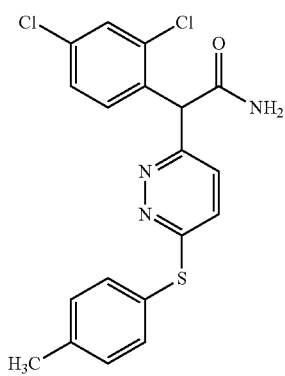 |
| 206 | 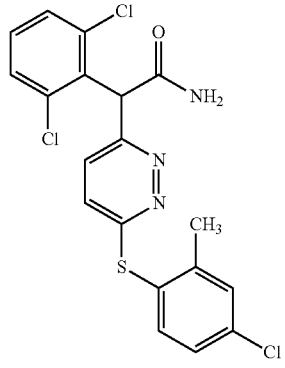 |
| 207 | 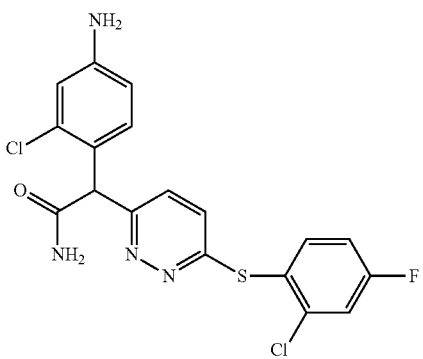 |
| 208 | 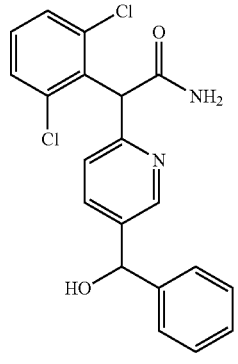 |

TABLE 3-continued

Formula Ie Inhibitors.

| cmpd # | structure |
|---|---|
| 209 | (structure) |

TABLE 4

Formula Ig Inhibitors.

| cpd # | structure |
|---|---|
| 202/301 | (structure) |
| 302 | (structure) |
| 303 | (structure) |

TABLE 4-continued

Formula Ig Inhibitors.

| cpd # | structure |
|---|---|
| 304 | (structure) |
| 305 | (structure) |
| 310 | (structure) |
| 311 | (structure) |
| 312 | (structure) |
| 313 | (structure) |

TABLE 4-continued

Formula Ig Inhibitors.

| cpd # | structure |
|---|---|
| 314 | |
| 306 | |
| 307 | |
| 308 | |
| 309 | |
| 319 | |
| 320 | 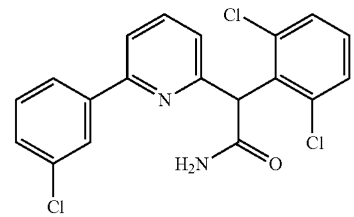 |
| 315 | 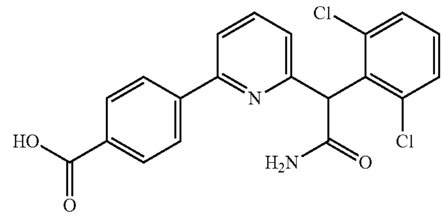 |
| 316 | 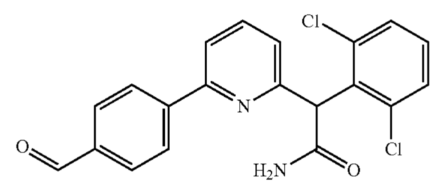 |
| 317 | 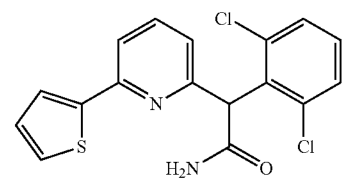 |
| 318 | 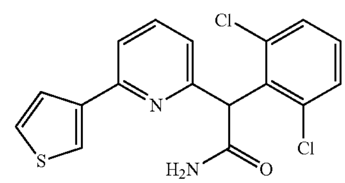 |
| 328 | 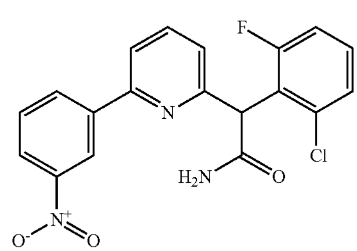 |
| 329 | 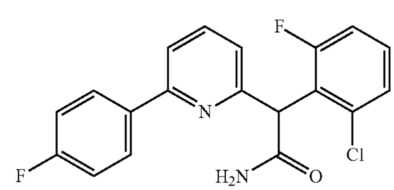 |

TABLE 4-continued

Formula Ig Inhibitors.

| cpd # | structure |
|-------|-----------|
| 321 | 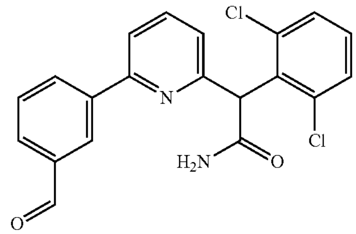 |
| 322 | 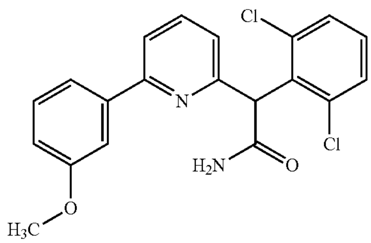 |
| 323 | 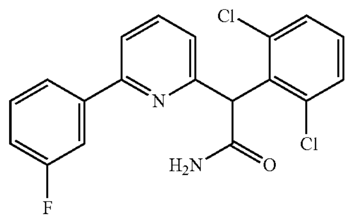 |
| 324 | 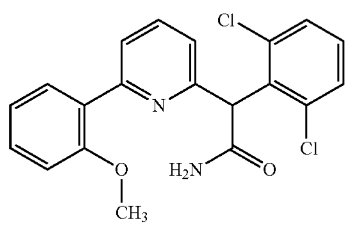 |
| 325 | 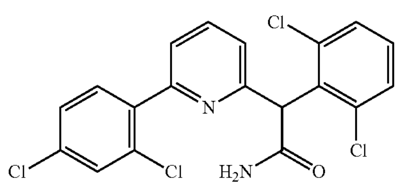 |
| 326 | 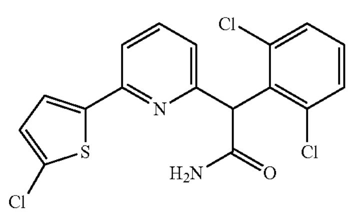 |
| 327 | 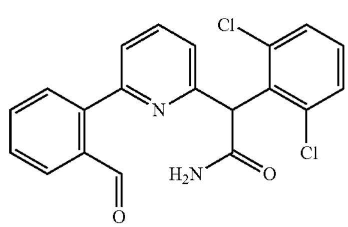 |
| 330 | |
| 331 | |
| 332 | |
| 333 | |
| 334 | |
| 335 | |
| 336 | |

TABLE 4-continued
Formula Ig Inhibitors.
| cpd # | structure |
|---|---|
| 337 | 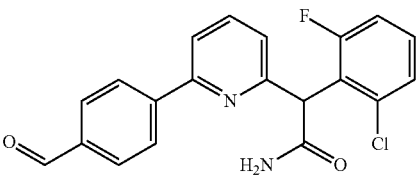 |
| 338 | 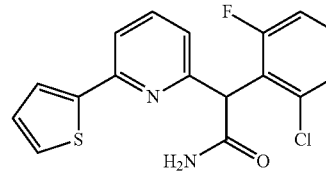 |
| 339 | 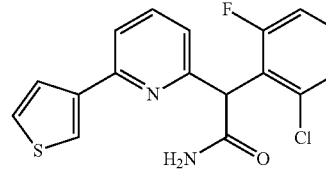 |
| 340 | 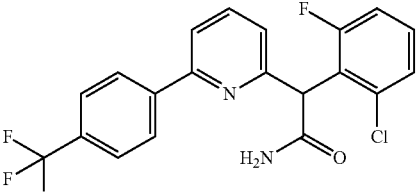 |
| 341 | 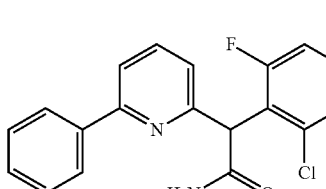 |
| 342 | 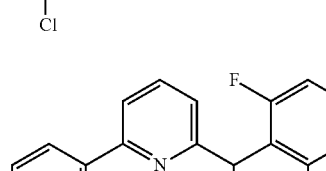 |
| 346 | 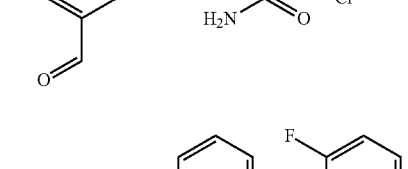 |
| 347 | 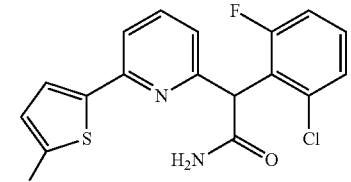 |
| 348 | 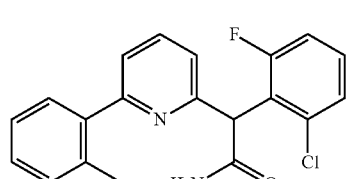 |
| 349 | 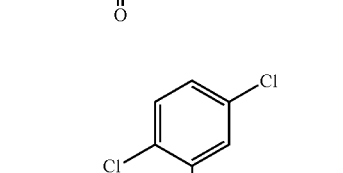 |
| 350 | 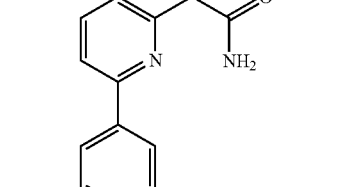 |
| 351 | 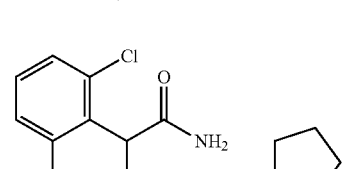 |

TABLE 4-continued

Formula Ig Inhibitors.

| cpd # | structure |
|---|---|
| 343 | 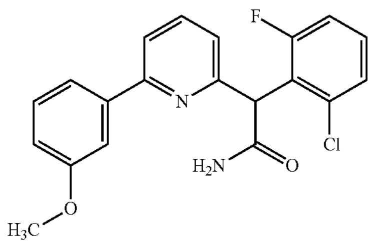 |
| 344 | 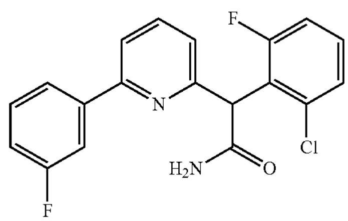 |
| 345 | 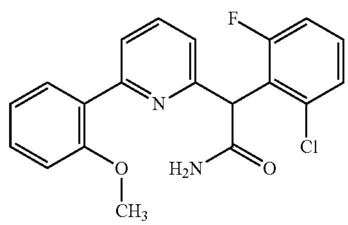 |
| 355 | 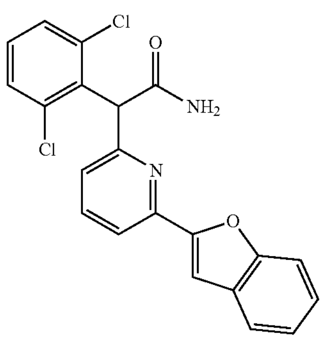 |
| 352 | 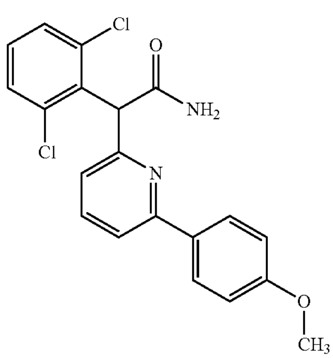 |
| 353 | |
| 354 | |
| 364 | |
| 356 | |

TABLE 4-continued
Formula Ig Inhibitors.
| cpd # | structure |
|---|---|
| 357 | 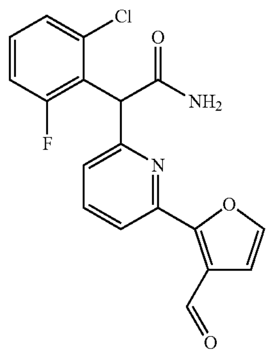 |
| 358 | 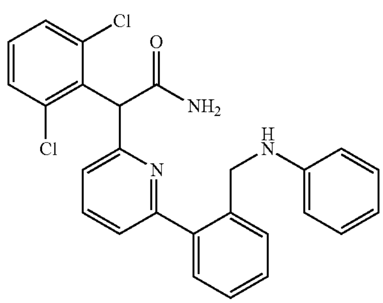 |
| 359 | 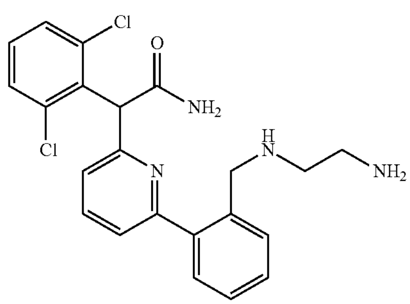 |
| 360 | 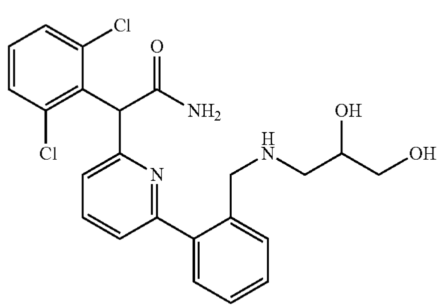 |
| 365 | 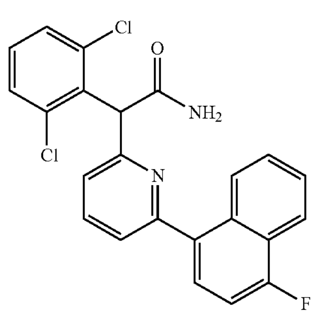 |
TABLE 4-continued
Formula Ig Inhibitors.
| cpd # | structure |
|---|---|
| 366 | 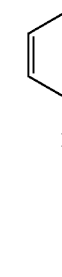 |
| 367 | 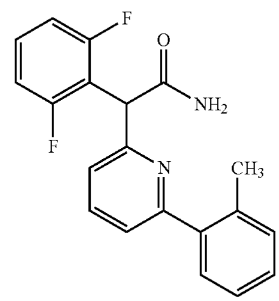 |
| 368 | 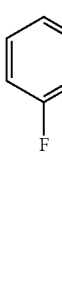 |
| 369 | 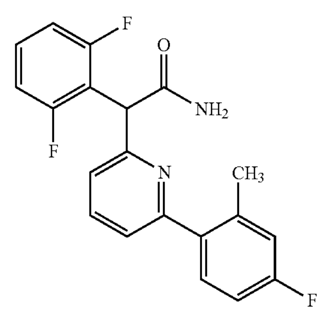 |
| 361 | 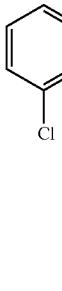 |

TABLE 4-continued
Formula Ig Inhibitors.
| cpd # | structure |
|---|---|
| 362 | 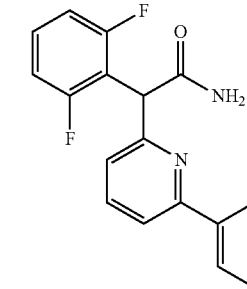 |
| 363 | 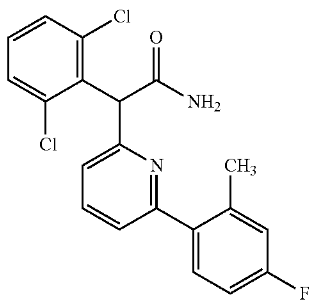 |
| 373 | 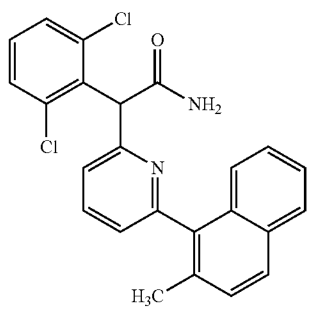 |
| 374 | 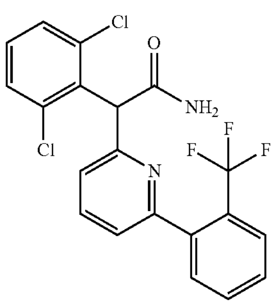 |
| 370 | |371 | 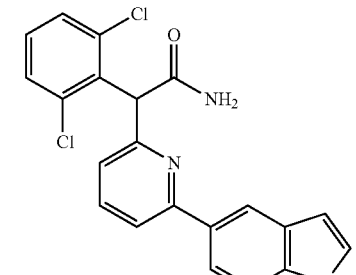 |
| 372 | |
| 382 | |
| 383 | |
| 375 | |

TABLE 4-continued

Formula Ig Inhibitors.

| cpd # | structure |
|---|---|
| 376 | (2,6-dichlorophenyl)-[6-(2,3-dimethylphenyl)pyridin-2-yl]acetamide |
| 377 | (2,6-dichlorophenyl)-[6-(2-ethylphenyl)pyridin-2-yl]acetamide |
| 378 | (2,6-dichlorophenyl)-[6-(2-hydroxyethylphenyl)pyridin-2-yl]acetamide |
| 379 | (2,6-dichlorophenyl)-[6-(3-trifluoromethylphenyl)pyridin-2-yl]acetamide |
| 384 | (2,6-dichlorophenyl)-(5-phenylpyrazin-2-yl)acetamide |
| 385 | (2,6-dichlorophenyl)-[6-(2-methoxymethoxyphenyl)pyridin-2-yl]acetamide |
| 386 | (2,6-dichlorophenyl)-[6-(2-hydroxyphenyl)pyridin-2-yl]acetamide |
| 387 | (2,6-dichlorophenyl)-[6-(3,5-bis-trifluoromethylphenyl)pyridin-2-yl]acetamide |
| 388 | (2,6-dichlorophenyl)-[6-(3,4,5-trifluorophenyl)pyridin-2-yl]acetamide |

TABLE 4-continued

Formula Ig Inhibitors.

| cpd # | structure |
|---|---|
| 380 | 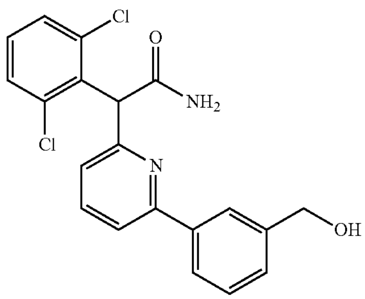 |
| 381 | 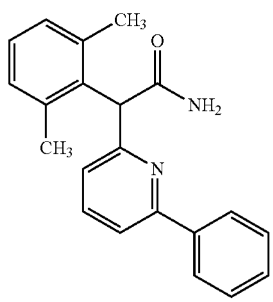 |
| 391 | 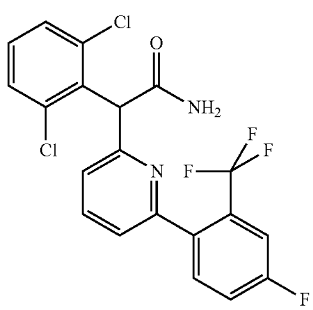 |
| 392 | 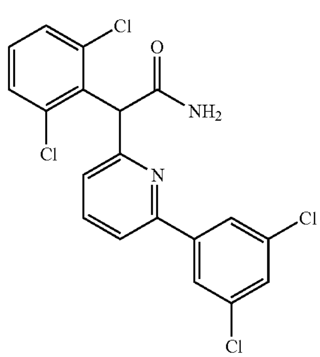 |
| 393 | 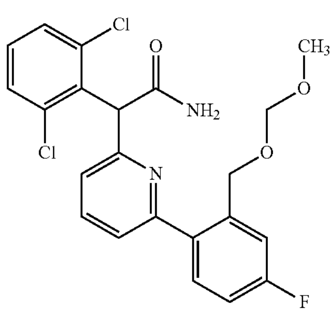 |
| 389 | |
| 390 | |
| 396 | |
| 397 | |

TABLE 4-continued

Formula Ig Inhibitors.

| cpd # | structure |
|---|---|
| 398 | 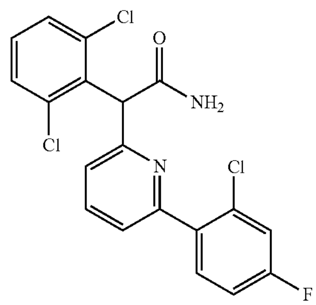 |
| 394 | 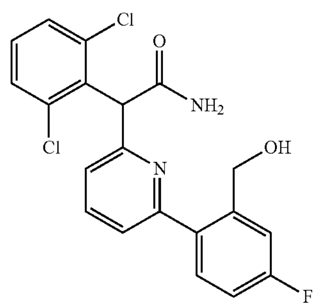 |
| 395 | 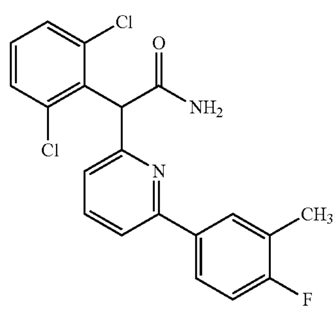 |
| 399 | 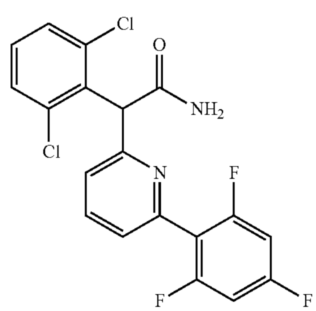 |
| 1301 | 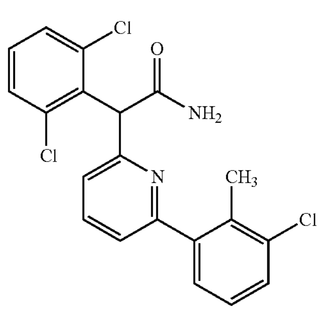 |

TABLE 5

Compound Ih Inhibitors.

| cpd # | structure |
|---|---|
| 401 | 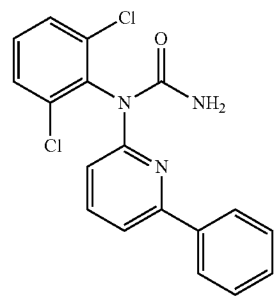 |
| 402 | 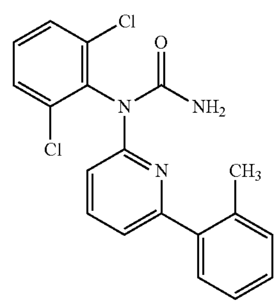 |
| 407 | 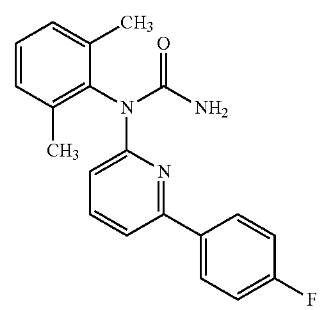 |
| 408 | 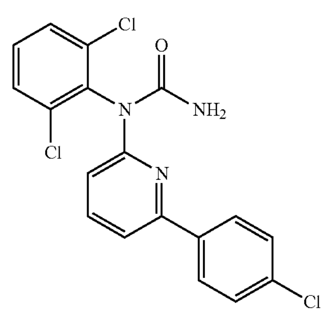 |
| 403 | 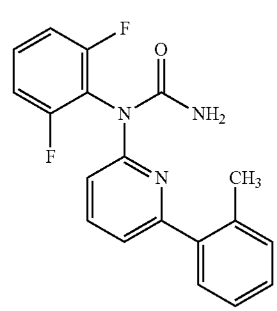 |

TABLE 5-continued

Compound Ih Inhibitors.

| cpd # | structure |
|---|---|
| 404 | 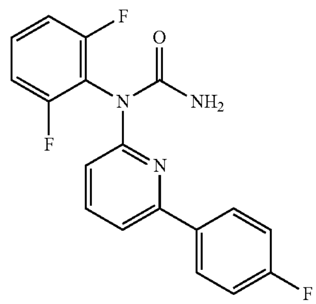 |
| 405 | 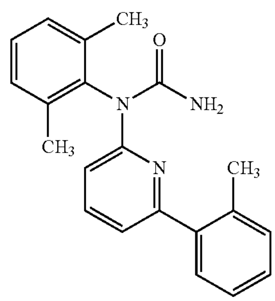 |
| 406 | 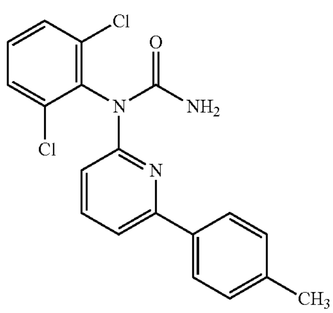 |
| 409 | 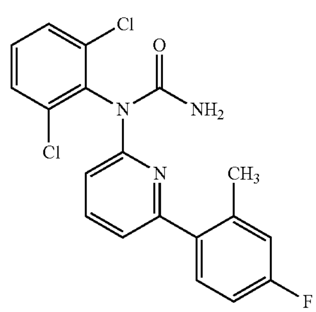 |
| 410 | 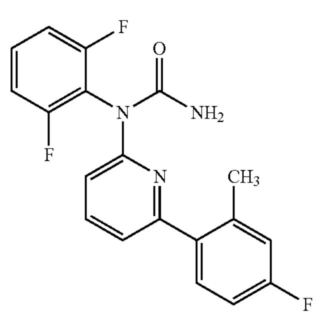 |
| 411 | 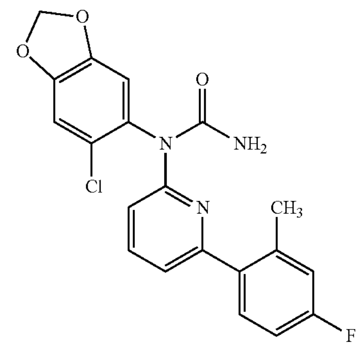 |
| 412 | 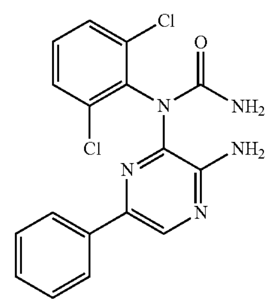 |

The activity of the p38 inhibitors of this invention may be assayed by in vitro, in vivo or in a cell line. In vitro assays include assays that determine inhibition of either the kinase activity or ATPase activity of activated p38. Alternate in vitro assays quantitate the ability of the inhibitor to bind to p38 and may be measured either by radiolabelling the inhibitor prior to binding, isolating the inhibitor/p38 complex and determining the amount of radiolabel bound, or by running a competition experiment where new inhibitors are incubated with p38 bound to known radioligands.

Cell culture assays of the inhibitory effect of the compounds of this invention may determine the amounts of TNF, IL-1, IL-6 or IL-8 produced in whole blood or cell fractions thereof in cells treated with inhibitor as compared to cells treated with negative controls. Level of these cytokines may be determined through the use of commercially available ELISAs.

An in vivo assay useful for determining the inhibitory activity of the p38 inhibitors of this invention is the suppression of hind paw edema in rats with *Mycobacterium butyricum*-induced adjuvant arthritis. This is described in J. C. Boehm et al., *J. Med. Chem.*, 39, pp. 3929-37 (1996), the disclosure of which is herein incorporated by reference. The p38 inhibitors of this invention may also be assayed in animal models of arthritis, bone resorption, endotoxin shock and immune function, as described in A. M. Badger et al., *J. Pharmacol. Experimental Therapeutics*, 279, pp. 1453-61 (1996), the disclosure of which is herein incorporated by reference.

The p38 inhibitors or pharmaceutical salts thereof may be formulated into pharmaceutical compositions for administration to animals or humans. These pharmaceutical compositions, which comprise and amount of p38 inhibitor effective to treat or prevent a p38-mediated condition and a pharmaceutically acceptable carrier, are another embodiment of the present invention.

The term "p38-mediated condition", as used herein means any disease or other deleterious condition in which p38 is known to play a role. This includes, conditions which are known to be caused by IL-1, TNF, IL-6 or IL-8 overproduction. Such conditions include, without limitation, inflammatory diseases, autoimmune diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxide synthase-2.

Inflammatory diseases which may be treated or prevented include, but are not limited to acute pancreatitis, chronic pancreatitis, asthma, allergies, and adult respiratory distress syndrome.

Autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented include, but are not limited to, osteoporosis, osteoarthritis and multiple myeloma-related bone disorder.

Proliferative diseases which may be treated or prevented include, but are not limited to, acute myelogenous leukemia, chronic myelogenous leukemia, metastatic melanoma, Kaposi's sarcoma, and multiple myeloma.

Angiogenic disorders which may be treated or prevented include solid tumors, ocular neovasculization, infantile haemangiomas.

Infectious diseases which may be treated or prevented include, but are not limited to, sepsis, septic shock, and Shigellosis.

Viral diseases which may be treated or prevented include, but are not limited to, acute hepatitis infection (including hepatitis A, hepatitis B and hepatitis C), HIV infection and CMV retinitis.

Neurodegenerative diseases which may be treated or prevented by the compounds of this invention include, but are not limited to, Alzheimer's disease, Parkinson's disease, cerebral ischemias or neurodegenerative disease caused by traumatic injury.

"p38-mediated conditions" also include ischemia/reperfusion in stroke, heart attacks, myocardial ischemia, organ hypoxia, vascular hyperplasia, cardiac hypertrophy, and thrombin-induced platelet aggregation.

In addition, p38 inhibitors in this invention are also capable of inhibiting the expression of inducible pro-inflammatory proteins such as prostaglandin endoperoxide synthase-2 (PGHS-2), also referred to as cyclooxygenase-2 (COX-2). Therefore, other "p38-mediated conditions" are edema, analgesia, fever and pain, such as neuromuscular pain, headache, cancer pain, dental pain and arthritis pain.

The diseases that may be treated or prevented by the p38 inhibitors of this invention may also be conveniently grouped by the cytokine (IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, rubella arthritis, acute synovitis, diabetes, pancreatic β-cell disease and Alzheimer's disease.

TNF-mediated disease or condition includes, rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and veterinary viral infections, such as lentivirus infections, including, but not limited to equine infectious anemia virus, caprine arthritis virus, visna virus or maedi virus; or retrovirus infections, including feline immunodeficiency virus, bovine immunodeficiency virus, or canine immunodeficiency virus.

IL-8 mediated disease or condition includes diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds of this invention may be used topically to treat or prevent conditions caused or exacerbated by IL-1 or TNF. Such conditions include inflamed joints, eczema, psoriasis, inflammatory skin conditions such as sunburn, inflammatory eye conditions such as conjunctivitis, pyresis, pain and other conditions associated with inflammation.

In addition to the compounds of this invention, pharmaceutically acceptable salts of the compounds of this invention may also be employed in compositions to treat or prevent the above-identified disorders.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium and potassium), alkaline earth metal (e.g., magnesium), ammonium and N—($C_{1-4}$ alkyl)$^{4+}$ salts. This invention also envisions the quaternization of any basic nitrogen-containing groups of the compounds disclosed herein. Water or oil-soluble or dispersible products may be obtained by such quaternization.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of p38 inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a p38-mediated condition comprising the step of administering to a patient one of the above-described pharmaceutical compositions. The term "patient", as used herein, means an animal, preferably a human.

Preferably, that method is used to treat or prevent a condition selected from inflammatory diseases, autoimmune diseases, destructive bone disorders, proliferative disorders, infectious diseases, degenerative diseases, allergies, reperfusion/ischemia in stroke, heart attacks, angiogenic disorders, organ hypoxia, vascular hyperplasia, cardiac hypertrophy, and thrombin-induced platelet aggregation.

According to another embodiment, the inhibitors of this invention are used to treat or prevent an IL-1, IL-6, IL-8 or TNF-mediated disease or condition. Such conditions are described above.

Depending upon the particular p38-mediated condition to be treated or prevented, additional drugs, which are normally administered to treat or prevent that condition may be administered together with the inhibitors of this invention. For example, chemotherapeutic agents or other anti-proliferative agents may be combined with the p38 inhibitors of this invention to treat proliferative diseases.

Those additional agents may be administered separately, as part of a multiple dosage regimen, from the p38 inhibitor-containing composition. Alternatively, those agents may be part of a single dosage form, mixed together with the p38 inhibitor in a single composition.

In order that the invention described herein may be more fully understood, the following examples are set forth. It should be understood that these examples are for illustrative purposes only and are not to be construed as limiting this invention in any manner.

Example 1

Synthesis of p38 Inhibitor Compound 1

Examples of the synthesis of several compounds of formula Ia are set forth in the following 4 examples.

A.

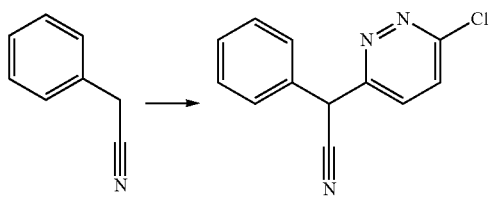

To a slurry of sodium amide, 90% (1.17 g., 30 mmol) in dry tetrahydrofuran (20 ml) we added a solution of benzyl cyanide (2.92 g., 25.0 mmol) in dry tetrahydrofuran (10 ml) at room temperature. The mixture was stirred at room temperature for 30 minutes. To the reaction mixture we added a solution of 3,6-dichloropyridazine (3.70 g., 25.0 mmol) in dry tetrahydrofuran (10 ml). After stirring for 30 minutes, the reaction mixture was diluted with an aqueous saturated sodium bicarbonate solution. The reaction mixture was then extracted with ethyl acetate. The layers were separated and the organic was washed with water, brine, dried over magnesium sulfate, filtered and concentrated in vacuo.

The residue was purified by chromatography on silica gel (eluant: 30% ethyl acetate in n-hexane) to give 3.71 g. (16.20 mmol ~54%) of product as a white solid.

B.

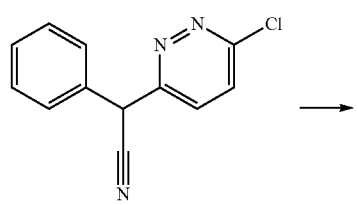

-continued

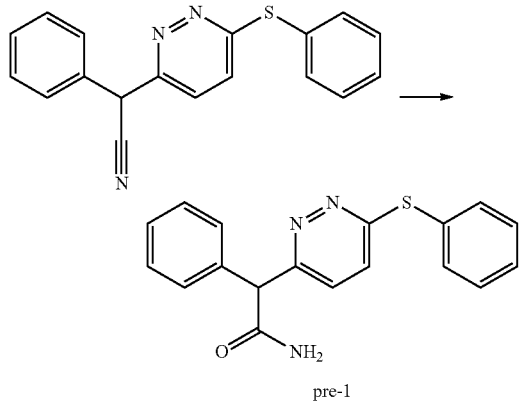

To a slurry of sodium hydride, 95% (0.14 g., 6.0 mmol) in dry tetrahydrofuran (10 ml) we added thiophenol (0.66 g, 6.0 ml.) at room temperature. The reaction mixture was then stirred for 10 minutes. To the reaction mixture we added a solution of the product from step A., above (1.31 g., 5.72 mmol) in absolute ethanol (20 ml.). The reaction mixture was then brought to reflux and stirred there for one hour. The cool reaction mixture was concentrated in vacuo. The residue was diluted with a 1N sodium hydroxide solution (10 ml), then extracted with methylene chloride. The organic phase was washed with water, brine, dried over magnesium sulfate and concentrated in vacuo.

The residue was purified by chromatography on silica gel (eluant: 20% ethyl acetate in n-hexane) to give 0.66 g. (2.19 mmol ~40%) of product as a white solid

C.

A mixture of the product from step B. (0.17 g., 0.69 mmol) and concentrated sulfuric acid (5 ml) was heated to 100° C. for one hour. The solution was cooled and adjusted to pH 8 with a saturated sodium bicarbonate solution. The reaction mixture was extracted with methylene chloride. The organic layer was washed with water, brine, dried over magnesium sulfate and concentrated in vacuo to give 0.22 g. (0.69 mmol ~100%) of compound pre-1 as an orange oil. $^1$H NMR (500 MHz, CD3OD) d7.7 (d), 7.5 (d), 7.4 (m), 7.3-7.2 (m).

D.

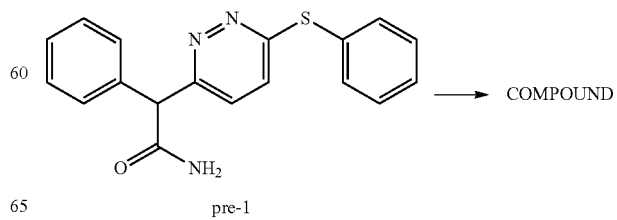

A solution of pre-1 from step C. (0.22 g., 0.69 mmol) and N,N-dimethylformamide dimethylacetal (0.18 g., 1.5 mmol) in toluene (5 ml) was heated at 100° C. for one hour. Upon cooling, the resulting solid was filtered and dissolved in warm ethyl acetate. The product was precipitated with the dropwise addition of diethyl ether. The product was then filtered and washed with diethyl ether to give 0.038 g. of compound 1 as a yellow solid. $^1$H NMR (500 MHz, CDCl$_3$) d8.63 (s), 7.63-7.21 (m), 6.44 (d).

Example 2

Synthesis of p38 Inhibitor Compound 2

A.

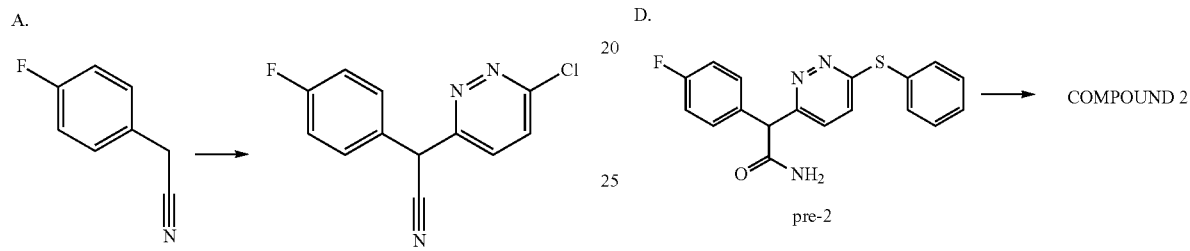

The first intermediate depicted above was prepared in a similar manner as in Example 1A, using 4-fluorophenylacetonitrile, to afford 1.4 g (5.7 mmol, ~15%) of product.

B.

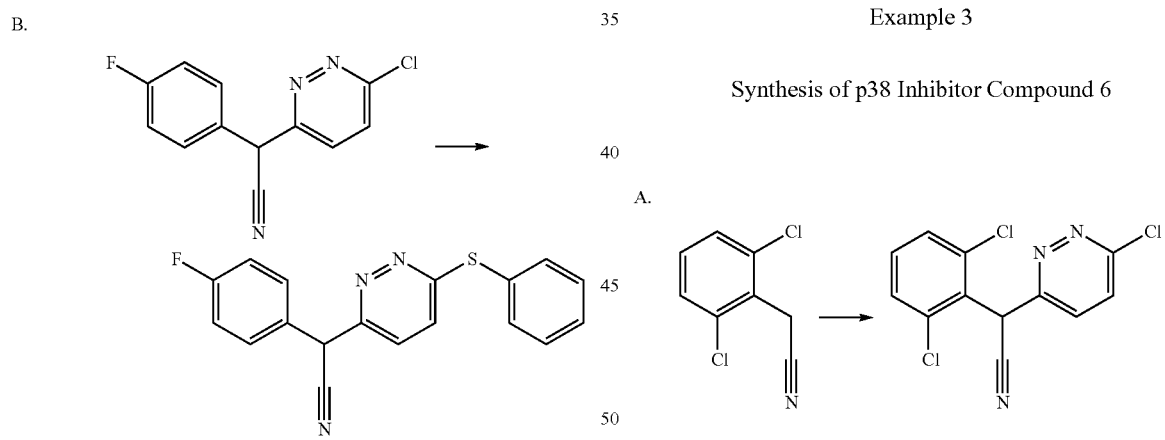

The above intermediate was prepared in a similar manner as in Example 1B. This afforded 0.49 g (1.5 mmol, 56%) of product.

C.

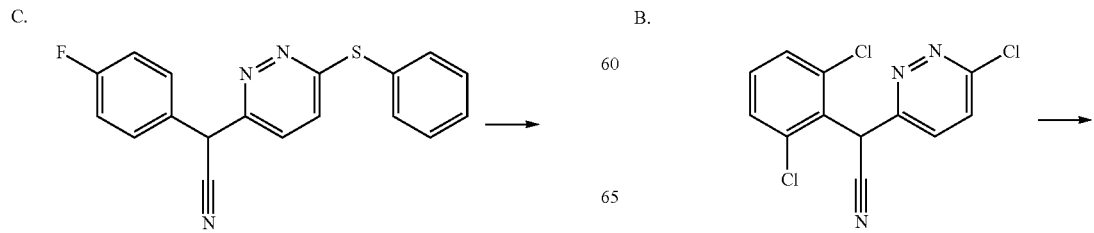

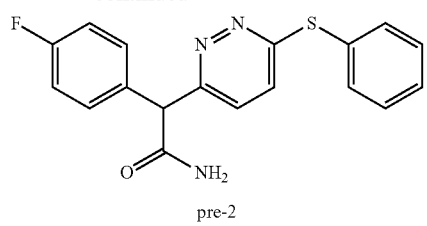

pre-2

The above intermediate was prepared in a similar manner as Example 1C. This afforded 0.10 g (0.29 mmol, 45%) of compound pre-2. $^1$H NMR (500 MHz, CDCl$_3$) d 7.65-7.48 (m), 7.47-7.30 (m), 7.29-7.11 (m), 7.06-6.91 (m), 5.85 (s, br).

D.

Compound 2 (which is depicted in Table 1) was prepared from pre-2 in a similar manner as in Example 1D. This afforded 0.066 g of product. $^1$H NMR (500 MHz, CDCl$_3$) d 8.60 (s), 7.62-7.03 (m), 6.44 (d)).

Example 3

Synthesis of p38 Inhibitor Compound 6

A.

The first intermediate in the preparation of compound 6 was prepared in a manner similar to that described in Example 1A, using 2,6-dichlorophenyl-acetonitrile, to afford 2.49 g (8.38, 28%) of product.

B.

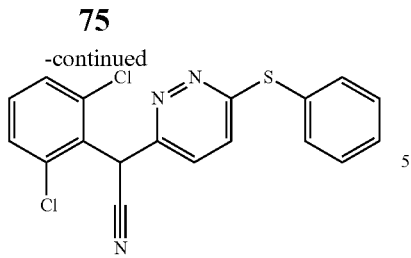

The next step in the synthesis of compound 6 was carried out in a similar manner as described in Example 1B. This afforded 2.82 g (7.6 mmol, 91%) of product.

C. 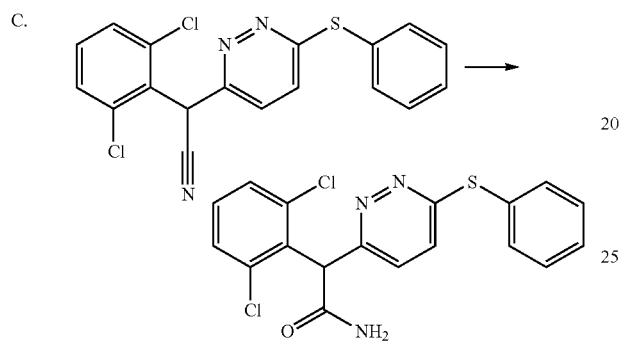

The final intermediate, pre-6, was prepared in a similar manner as described in Example 1C. This afforded 0.89 g (2.3 mmol, 85%) of product. $^1$H NMR (500 MHz, CD3OD) d 7.5-7.4 (dd), 7.4 (m), 7.3 (d), 7.2 (m), 7.05 (d).

D. 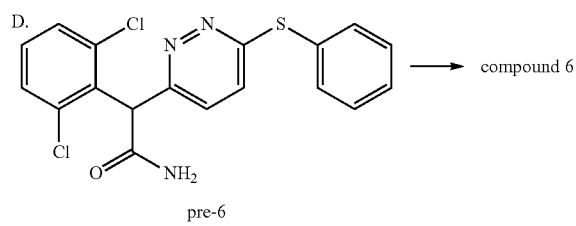 → compound 6 pre-6

The final step in the synthesis of compound 6 (which is depicted in Table 1) was carried out as described in Example 1D. This afforded 0.06 g of product. $^1$H NMR (500 MHz, CDCl3) d 8.69 (s), 7.65-7.59 (d), 7.58-7.36 (m), 7.32-7.22 (m), 6.79 (d), 6.53 (d).

Example 4

Preparation of p38 Inhibitor Compound 5

A.

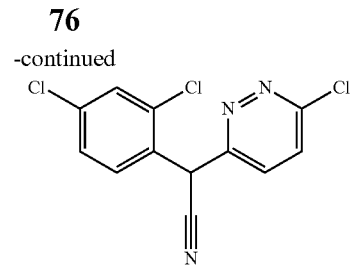

The first intermediate in the synthesis of compound 5 was prepared in a similar manner as described in Example 1A, using 2,4-dichlorophenylacetonitrile, to afford 3.67 g (12.36 mmol, 49%) of product.

B. 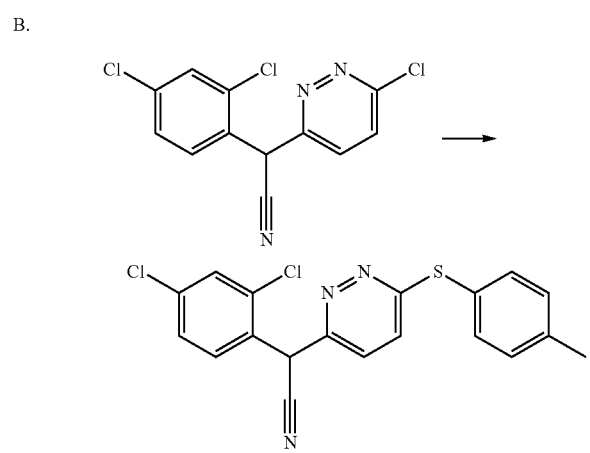

The second intermediate was prepared in a similar manner as described in Example 1B. This afforded 3.82 g (9.92 mmol, 92%) of product.

C.

pre-5

The final intermediate, pre-5, was prepared in a similar manner as described in Example 1C. This afforded 0.10 g (0.24 mmol, 92%) of product. $^1$H NMR (500 MHz, CD3OD) d 7.9 (d), 7.7 (d), 7.6-7.5 (dd), 7.4-7.3 (m), 2.4 (s).

D.

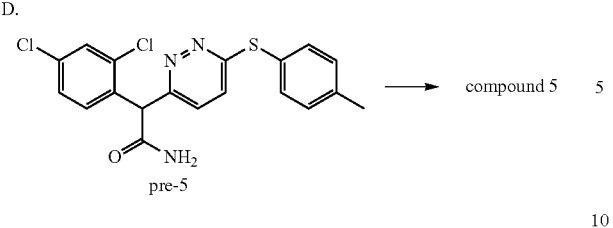

The final step in the preparation of compound 5 (which is depicted in Table 1) was carried out in a similar manner as described in Example 1D. This afforded 0.06 g of product. $^1$H NMR (500 MHz, CDCl3) d 8.64 (s), 7.51-7.42 (m), 7.32-7.21 (m), 6.85 (d), 6.51 (d), 2.42 (s).

Other compounds of formula Ia of this invention may be synthesized in a similar manner using the appropriate starting materials.

Example 5

Preparation of A p38 Inhibitor Compound of Formula Ib

An example of the synthesis of a p38 inhibitor of this invention of the formula Ib is presented below.

A.

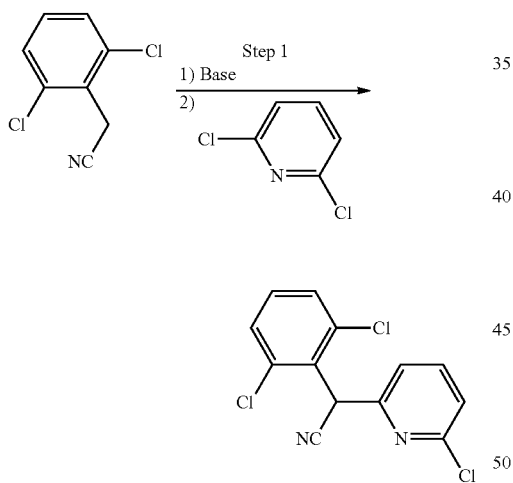

To a slurry of sodium amide, 90% (1.1 eq) in dry tetrahydrofuran was added a solution of 2,6-dichlorobenzyl cyanide (1.0 eq) in dry tetrahydrofuran at room temperature. The mixture was stirred at room temperature for 30 minutes. To the reaction mixture was added a solution of 2,6-dichloropyridine (1 eq) in dry tetrahydrofuran. The reaction was monitored by TLC and, when completed the reaction mixture was diluted with an aqueous saturated sodium bicarbonate solution. The reaction mixture was then extracted with ethyl acetate. The layers were separated and the organic layer was washed with water, brine, dried over magnesium sulfate, filtered and concentrated in vacuo. The residue was purified by chromatography on silica gel to yield pure product.

B.

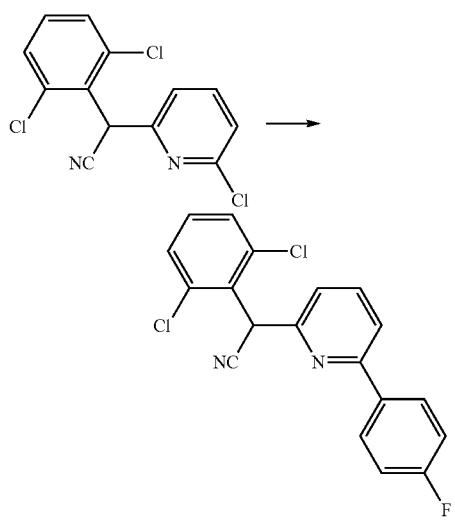

To a solution of 4-fluoro-bromobenzene (1 eq) in dry tetrahydrofuran at −78° C. was added t-butyllithium (2 eq, solution in hexanes). The reaction mixture was then stirred for 30 minutes. To the reaction mixture was added a solution of the product from Step A (1 eq) in dry THF. The reaction mixture was then monitored and slowly brought to room temperature. The reaction mixture was quenched with water then extracted with methylene chloride. The organic phase was washed with water, brine, dried over magnesium sulfate and concentrated in vacuo. The residue was purified by chromatography on silica gel to yield the product.

C.

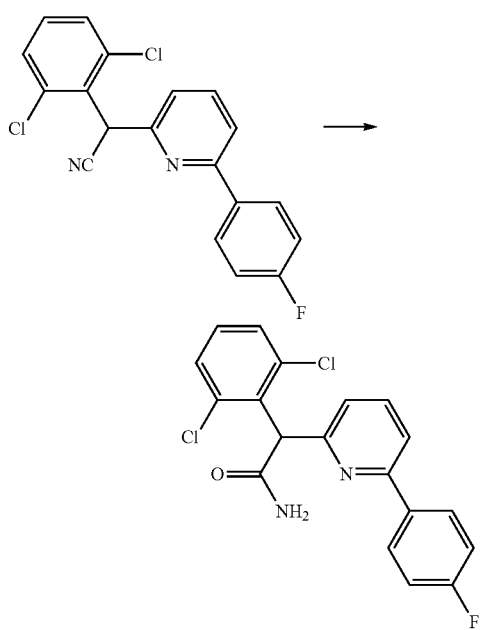

A mixture of the product step B and concentrated sulfuric acid was heated to 100° C. for one hour. The solution was cooled and adjusted to pH 8 with a saturated sodium bicarbonate solution. The reaction mixture was extracted with methylene chloride. The organic layer was washed with water, brine, dried over magnesium sulfate and concentrated in vacuo to give product. The final product was purified by silica gel flash chromatography

D.

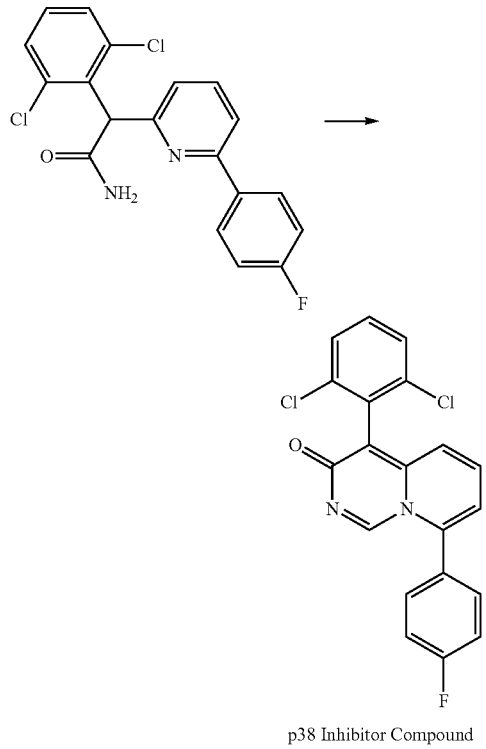

p38 Inhibitor Compound

A solution of the product Step C (1 eq) and N,N-Dimethylformamide dimethylacetal (2 eq) in toluene is heated at 100° C. for one hour. Upon cooling, the resulting mixture is filtered and dissolved in warm ethyl acetate. The product is precipitated with the dropwise addition of diethyl ether. The product is then filtered and washed with diethyl ether to give a p38 inhibitor of formula Ib. The final product is further purified by silica gel chromatography.

Other compounds of formula Ib of this invention may be synthesized in a similar manner using the appropriate starting materials.

Example 6

Synthesis of p38 Inhibitor Compound 103

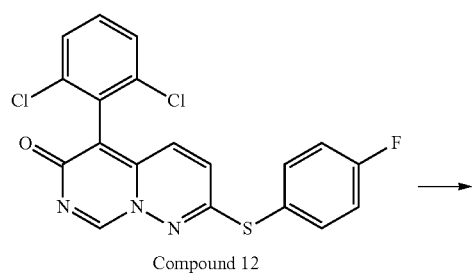

Compound 12

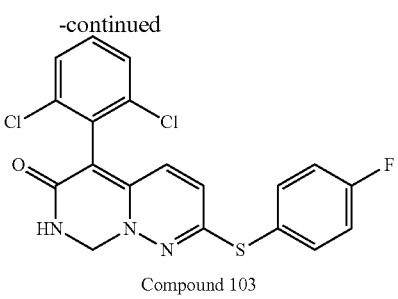

Compound 103

This example sets forth a typical synthesis of a compound of formula Ic.

A.

The p38 inhibitor compound 12 is prepared essentially as set forth for in Example 4, except that 4-fluorothiophenyl is utilized in step B.

B.

Compound 12 was dissolved in dry THF (5 ml) at room temperature. To this solution we added diisobutylaluminum hydride (1M solution in toluene, 5 ml, 5 mmol) and the reaction was stirred at room temperature for 1 hour. The reaction mix was then diluted with ethyl acetate and quenched by the addition of Rochelle salt. The layers were separated and the organic layer was isolated, washed with water, washed with brine, dried over magnesium sulfate and filtered to yield crude compound 103. The crude product was chromatographed on silica gel eluting with 2% methanol in methylene chloride. Pure compound 103 was thus obtained (210 mg, 50% yield): $^1$H NMR (500 Mhz, CDCl3) 7.51 (m, 1H), 7.38 (d, 2H), 7.20 (t, 2H), 7.08 (t, 2H), 6.70 (broad s, 1H), 6.30 (dd, 2H), 5.20 (s, 2H).

Example 7

Synthesis of p38 Inhibitor Compound 201

A.

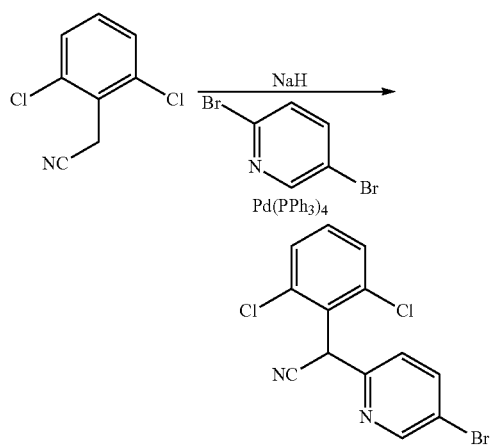

The starting nitrile shown above (5.9 g, 31.8 mmol) was dissolved in DMF (20 ml) at room temperature. Sodium hydride (763 mg, 31.8 mmol) was then added, resulting in a bright yellow-colored solution. After 15 minutes a solution of 2,5 dibromopyridine (5.0 gr., 21.1 mmol) in DMF (10 ml) was added followed by Palladium tetrakis (triphenylphosphine) (3 mmol). The solution was then refluxed for 3 hrs. The reaction was cooled to room temperature and diluted with ethyl acetate. The organic layer was then isolated, washed with water and then with brine, dried over magnesium sulfate, filtered and evaporated in vacuo to a crude oil. Flash column chromatography eluting with 10% ethyl acetate in hexane afforded product (5.8 g, 84%) as an off white solid.

B.

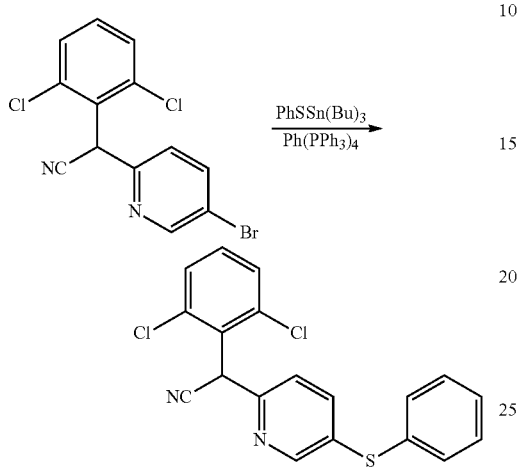

The bromide produced in step A (194.8 mg, 0.57 mmol) was dissolved in xylene (15 ml). To this solution we added thiophenylstannane (200 μl, 587 mmol) and palladium tetrakis (triphenylphosphine) (25 mg). The solution was refluxed overnight, cooled, filtered and evaporated in vacuo. The crude product was chromatographed on silica gel, eluting with methylene chloride, to yield pure product (152 mg, 72%) as a yellow oil.

C.

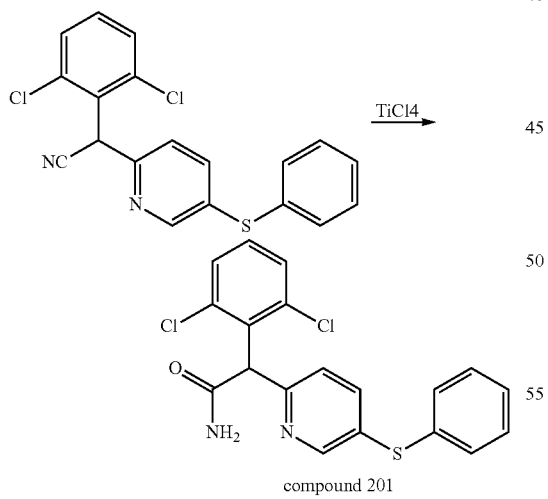

compound 201

The nitrile produced in step B (1.2 g, 3.37 mmol) was dissolved in glacial acetic acid (30 ml). To this solution we added water (120 μl, 6.67 mmol) followed by titanium tetrachloride (760 μl, 6.91 mmol), which resulted in an exotherm. The solution was then refluxed for two hours, cooled and poured into 1N HCl. The aqueous layer was extracted with methylene chloride. The organic layer was backwashed with 1N NaOH, dried over magnesium sulfate and filtered over a plug of silica gel. The plug was first eluted with methylene chloride to remove unreacted starting materials, and then with ethyl acetate to yield compound 201. The ethyl acetate was evaporated to yield pure compound 201 (1.0 g, 77%).

Example 8

Synthesis of p38 Inhibitor Compound 110

A.

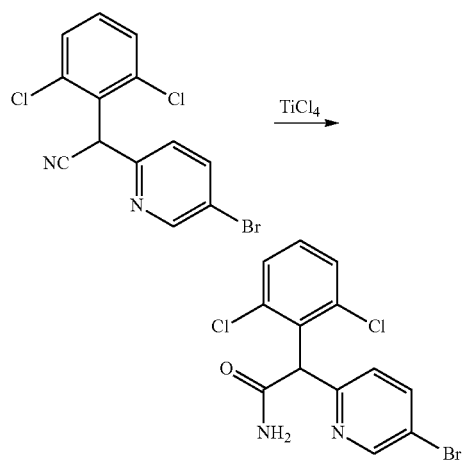

The starting nitrile (3.76 g, 11.1 mmol) was first dissolved in glacial acetic acid (20 ml). To this solution we added titanium tetrachloride (22.2 mmol) and water (22.2 mmol) and heated the solution to reflux for 1 hour. The reaction mixture was then cooled and diluted in water/ethyl acetate. The organic layer was then isolated, washed with brine and dried over magnesium sulfate. The organic layer was then filtered and evaporated in vacuo. The resulting crude product was chromatographed on silica gel eluting with 5% methanol in methylene chloride to afford pure product as a yellow foam (2.77 g, 70%)

B.

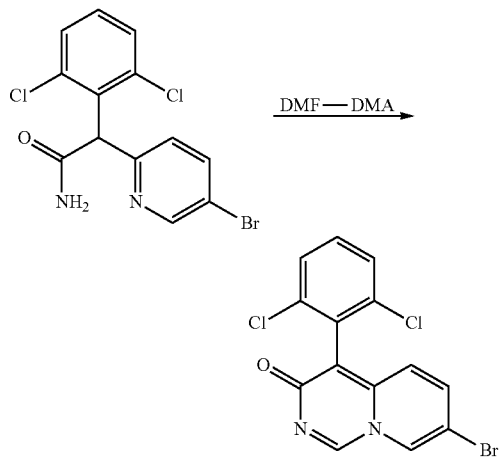

The amide produced in step A (1.54 g, 4.3 mmol) was dissolved in toluene (20 ml). We then added N,N-dimethylformamide dimethylacetal (1.53 g, 12.9 mmol), heated the resulting solution for 10 minutes then allowed it to cool to room temperature. The reaction was then evaporated in vacuo and the residue was chromatographed on silica gel eluting with 2-5% methanol in methylene chloride. The recovered material was then dissolved in hot ethyl acetate. The solution was allowed to cool resulting in the crystallization of pure product as a yellow solid (600 mg, 40%). Additional material (~800 mg) was available from the mother liquor.

C.

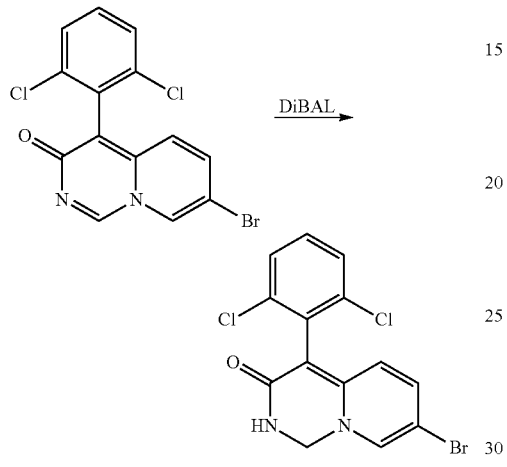

The bromide from step B (369 mg, 1 mmol) was dissolved in THF (10 ml). We then added Diisobutylaluminum hydride (1.0M solution, 4 mmol), stirred the reaction at room temperature for 10 minutes, and then quenched the reaction with methanol (1 ml). A saturated solution of Rochelle salts was then added and the mixture was extracted with ethyl acetate. The organic layer was isolated, dried over magnesium sulfate, evaporated and the residue was chromatographed on silica gel eluting with 1-3% methanol in methylene chloride to afford a bright orange solid (85 mg, 23% yield).

D.

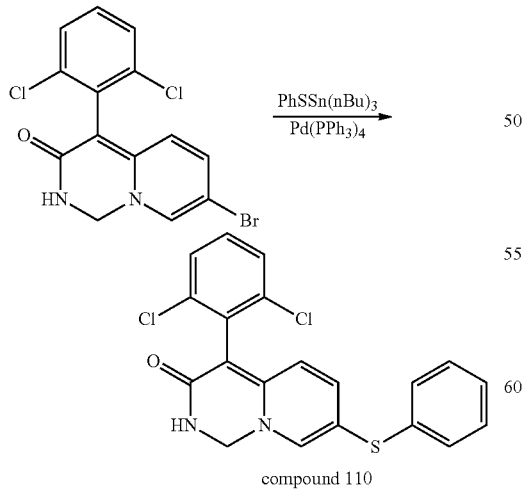

compound 110

The bromide produced in step C (35.2 mg, 0.1 mmol) was dissolved in xylene (12 ml). To this solution we added thiophenol (0.19 mmol) followed by tributyltin methoxide (0.19 mmol). The resulting solution was heated to reflux for 10 minutes, followed by the addition of palladium tetrakis (triphenylphosphine) (0.020 mmol). The reaction was heated and monitored for the disappearance of the bromide starting material. The reaction was then cooled to room temperature and passed through a plug of silica gel. The plug was eluted initially with methylene chloride to remove excess tin reagent and then with 5% methanol in ethyl acetate to elute the p38 inhibitor. The filtrate was concentrated and then re-chromatographed on silica gel using 5% methanol in ethyl acetate as eluant affording pure compound 110 (20 mg, 52%).

Example 9

Synthesis of p38 Inhibitor Compound 202

A.

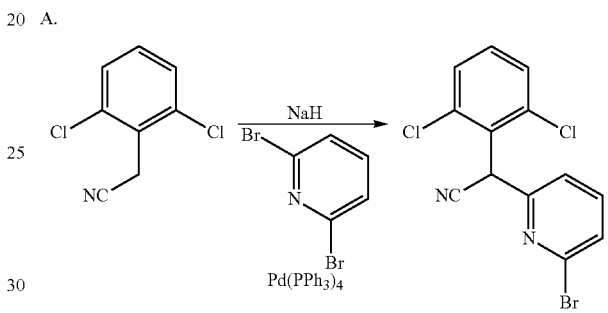

The starting nitrile (2.32 g, 12 mmol) was dissolved in DMF (10 ml) at room temperature. Sodium hydride (12 mmol) was then added resulting in a bright yellow colored solution. After 15 minutes, a solution of 2,6 dibromopyridine (2.36 gr., 10 mmol) in DMF (5 ml) was added, followed by Palladium tetrakis (triphenylphosphine) (1.0 mmol). The solution was then refluxed for 3 hours. The reaction was next cooled to room temperature and diluted with ethyl acetate. The organic layer was isolated, washed with water and brine, dried over magnesium sulfate, filtered and evaporated in vacuo to a crude oil. Flash column chromatography eluting with 10% ethyl acetate in hexane afforded product (1.45 g, 42%) as a white solid.

B.

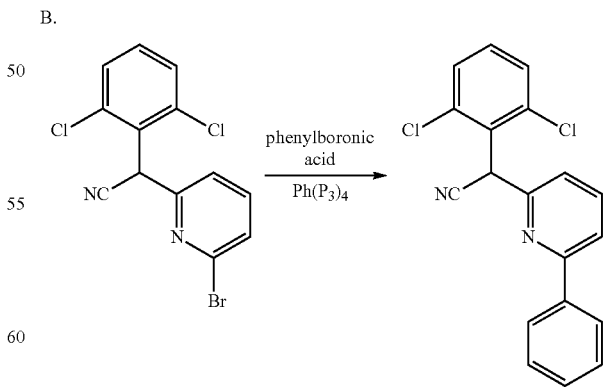

The bromo compound produced in step A (1.77 g, 5.2 mmol) was dissolved in toluene (20 ml) and the resulting solution was degassed. Under a nitrogen atmosphere, a solution of phenylboronic acid (950 mg, 7.8 mmol) in ethanol (4 ml) and a solution of sodium carbonate (1.73 g, 14 mmol) in water (4 ml) were added. The reaction mixture was heated to reflux for one hour and then was cooled to room temperature. The reaction was diluted with ethyl acetate and washed with water and brine. The organic layer was then dried with magnesium sulfate, filtered and concentrated in vacuo. The residue was purified on silica gel eluting with 30% ethyl acetate in hexane to afford product as a white solid (1.56 g, 88%).

C.

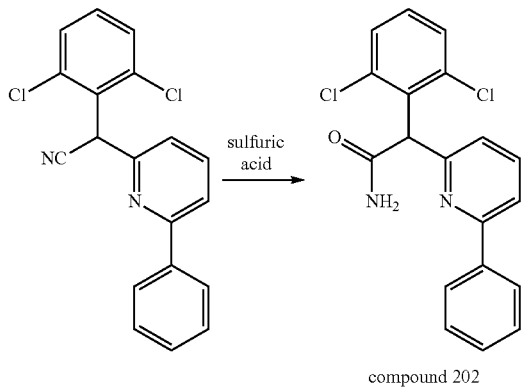

compound 202

The nitrile from step B (700 mg, 2.07 mmol) was dissolved in concentrated sulfuric acid (10 ml) and heated to 80° C. for 1 hour. The reaction was then cooled to room temperature and the pH was adjusted to 8 using 6N sodium hydroxide. The mixture was next extracted with ethyl acetate. The organic layer was isolated, dried with magnesium sulfate and evaporated in vacuo to yield compound 202 as a yellow foam (618 mg, 84%).

Example 10

Synthesis of Compound 410

A.

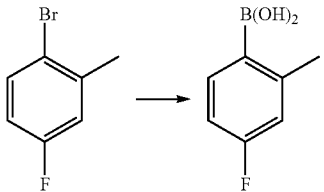

In a flame-dried 100 ml round-bottomed flask, 2.28 g (93.8 mmol) of magnesium chips were added to 50 ml of anhydrous tetrahydrofuran. One crystal of iodine was added forming a light brown color. To the solution was added 1.5 ml of a 10.0 ml (79.1 mmol) sample of 2-bromo-5-fluorotoluene. The solution was heated to reflux. The brown color faded and reflux was maintained when the external heat source was removed indicating Grignard formation. As the reflux subsided, another 1.0-1.5 ml portion of the bromide was added resulting in a vigorous reflux. The process was repeated until all of the bromide had been added. The olive-green solution was externally heated to reflux for one hour to ensure complete reaction. The solution was cooled in an ice-bath and added via syringe to a solution of 9.3 ml (81.9 mmol) of trimethyl borate in 100 ml of tetrahydrofuran at −78° C. After the Grignard reagent had been added, the flask was removed from the cooling bath and the solution was stirred at room temperature overnight. The grayish-white slurry was poured into 300 ml of $H_2O$ and the volatiles were evaporated in vacuo. HCl (400 ml of 2N solution) was added and the milky-white mixture was stirred for one hour at room temperature. A white solid precipitated. The mixture was extracted with diethyl ether and the organic extract was dried ($MgSO_4$) and evaporated in vacuo to afford 11.44 g (94%) of the boronic acid as a white solid.

B.

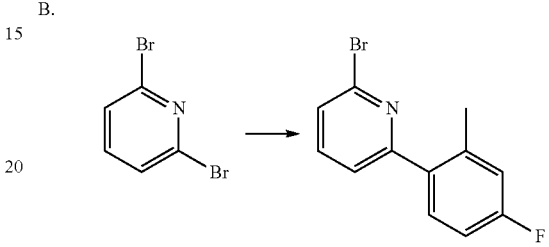

In a 100 ml round-bottomed flask, 7.92 g (33.4 mmol) of 2,6-dibromopyridine was dissolved in 50 ml of anhydrous toluene forming a clear, colorless solution. 4-fluoro-2-methylbenzene boronic acid (5.09 g, 33.1 mmol) produced in step A was added forming a white suspension. Thallium carbonate (17.45 g, 37.2 mmol) was added followed by a catalytic amount (150 mg) of $Pd(PPh_3)_4$. The mixture was heated to reflux overnight, cooled, and filtered over a pad of silica gel. The silica was washed with $CH_2Cl_2$ and the filtrate was evaporated to afford a white solid. The solid was dissolved in a minimal amount of 50% $CH_2Cl_2$/hexane and chromatographed on a short column of silica gel using 30% $CH_2Cl_2$/hexane to afford 6.55 g (74%) of the 2-bromo-6-(4-fluoro-2-methylphenyl)pyridine as a white solid.

C.

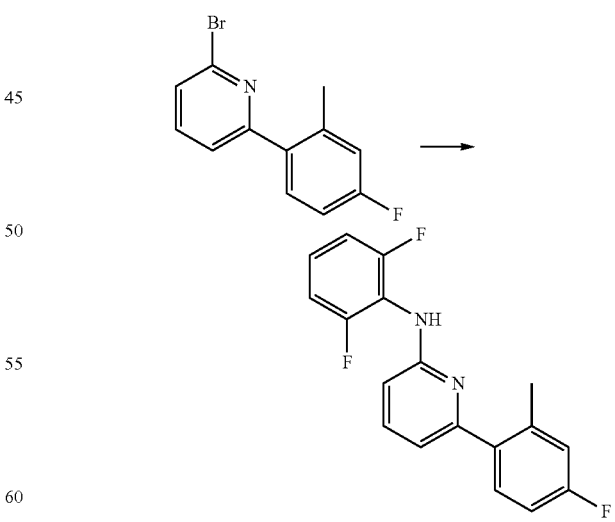

In a 50 ml round-bottomed flask, 550 mg (2.07 mmol) of 2-bromo-6-(4-fluoro-2-methylphenyl)pyridine produced in step B was dissolved in 30 ml of anhydrous tetrahydrofuran forming a clear, colorless solution. 2,6-difluoroaniline (2.14 ml, 2.14 mmol) was added followed by 112 mg (2.79 mmol)

of a 60% NaH suspension in mineral oil. Gas evolution was observed along with a mild exotherm. The solution was heated to reflux overnight and then cooled. The reaction mixture was poured in 10% NH₄Cl and extracted with CH₂Cl₂. The organic extract was dried (MgSO₄) and evaporated in vacuo to afford a brown oil that was a mixture of the product and starting material. The material was chromatographed on a short column of silica gel using 50% CH₂Cl₂/hexane to afford 262 mg (40%) of 2-(2,6-difluorophenyl)-6-(4-fluoro-2-methylphenyl)pyridine as a colorless oil.

D.

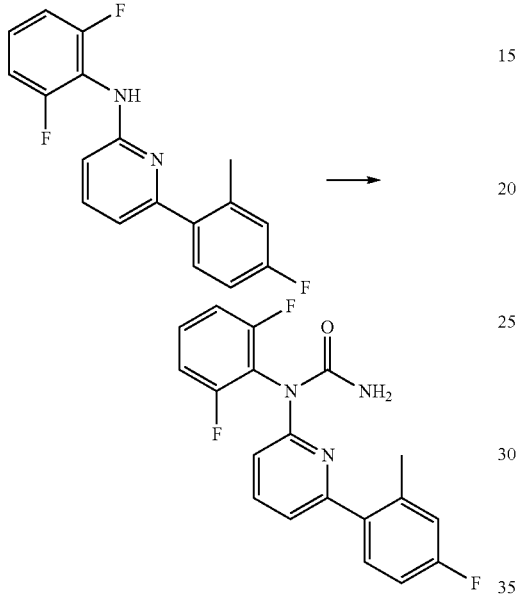

In a 100 ml round-bottomed flask, 262 mg (834 mmol) of 2-(2,6-difluorophenyl)-6-(4-fluoro-2-methylphenyl)pyridine produced in step C was dissolved in 30 ml of anhydrous CHCl₃ forming a clear, colorless solution. Chlorosulfonyl isocyanate (1.0 ml, 11.5 mmol) was added and the light yellow solution was stirred at room temperature overnight. Water (~30 ml) was added causing a mild exotherm and vigorous gas evolution. After stirring overnight, the organic layer was separated, dried (MgSO₄) and evaporated in vacuo to afford a brown oil that was a mixture of the product and starting material. The material was chromatographed on a short column of silica gel using 10% EtOAc/CH₂Cl₂. The recovered starting material was re-subjected to the reaction conditions and purified in the same manner to afford a total of 205 mg (69%) of the urea as a white solid.

Example 11

Synthesis of Compound 138

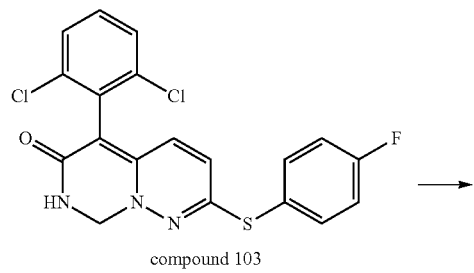

compound 103

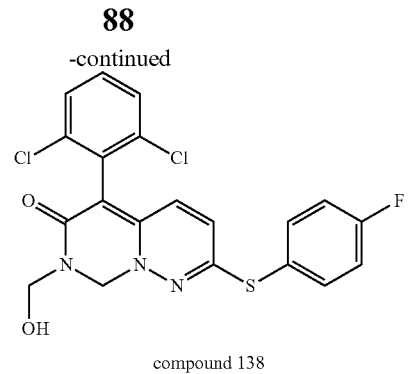

compound 138

Compound 103 (106 mg, 0.25 mmol) was dissolved in THF (0.5 ml) and to this solution was added triethylamine (35 µl, 0.25 mmol) followed by and excess of formaldehyde (37% aqueous solution, 45 mg). The reaction was allowed to stir at room temperature overnight. The reaction mixture was then rotovapped under reduced pressure and the residue was dissolved in methylene chloride and applied to a flash silica gel column. The column was eluted with 2% methanol in methylene chloride to yield pure product (78 mg, 70% yield).

Example 12

Synthesis of Prodrugs of Compound 103

A.

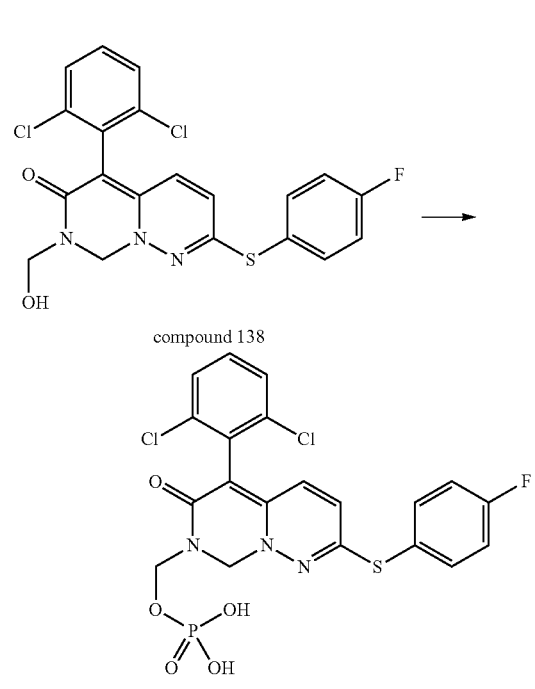

Compound 138 (1 equivalent) is dissolved in methylene chloride and to this solution is added triethylamine (1 equivalent) followed by dibenzylphosphonyl chloride (1 equivalent). The solution is stirred at room temperature and monitored by TLC for consumption of starting material. The methylene chloride layer is then diluted with ethyl acetate and washed with 1N HCl, saturated sodium bicarbonate and saturated NaCl. The organic layer is then dried, rotovapped and the crude product is purified on silica gel. The pure product is then dissolved in methanol and the dibenzyl esters are deprotected with 10% palladium on charcoal under a hydrogen atmosphere. When the reaction is monitored as complete, the catalyst is filtered over celite and the filtrate is rotovapped to yield the phosphate product.

B.

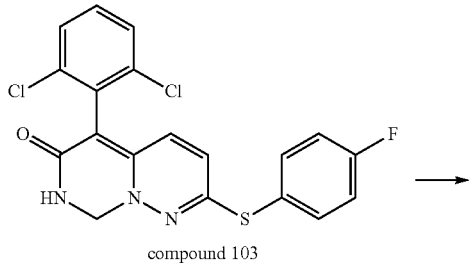

compound 103

Compound 103 (210 mg, 1.05 mmol) was dissolved in THF (2 ml) and cooled to −50° C. under a nitrogen atmosphere. To this solution was added lithium hexamethyldisilazane (1.1 mmol) followed by chloroacetyl chloride (1.13 mmol). The reaction was removed from the cooling bath and allowed to warm to room temperature, after which time the reaction was diluted with ethyl acetate and quenched with water. The organic layer was washed with brine, dried and rotovapped to dryness. The crude product was flash chromatographed on silica gel using 25% ethyl acetate in hexane as eluant to yield 172 mg (70%) of pure desired product, which was used as is in the next reactions.

C.

-continued dimethylaminoacetyl prodrug of compound 103

The chloroacetyl compound is dissolved in methylene chloride and treated with an excess of dimethyl amine. The reaction is monitored by TLC and when complete all volatiles are removed to yield desired product.

Example 13

Synthesis of Compounds 34 and 117

A.

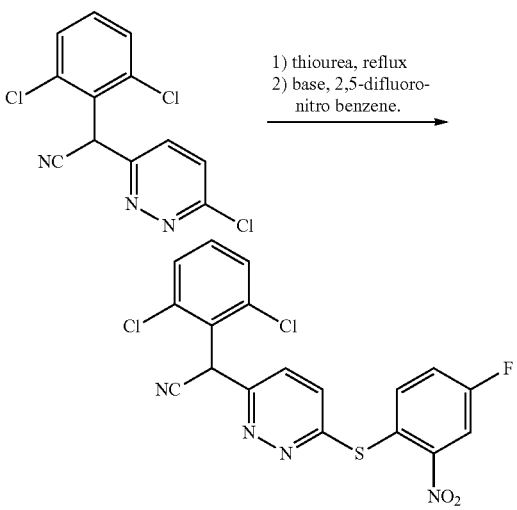

1) thiourea, reflux
2) base, 2,5-difluoronitro benzene.

The nitrile from Example 5, step A (300 mg, 1.0 mmol) was dissolved in ethanol (10 ml) and to this solution was added thiourea (80.3 mg, 1.05 mmol). The reaction was brought to reflux for 4 hours at which point TLC indicated that all starting material was consumed. The reaction was cooled and all volatiles were removed under reduced pressure, and the residue was dissolved in acetone (10 ml).

To this solution was then added 2,5-difluoronitrobenzene (110 µl, 1.01 mmol) followed by potassium carbonate (200 mg, 1.45 mmol) and water (400 µl). The reaction was allowed to stir at room temperature overnight. The reaction was then diluted with methylene chloride (25 ml) and filtered through a cotton plug. All volatiles were removed under reduced pressure and the residue was flashed chromatographed on silica gel eluting with a gradient from 10%-25% ethyl acetate in hexane to yield the desired product (142 mg, 33%).

B.

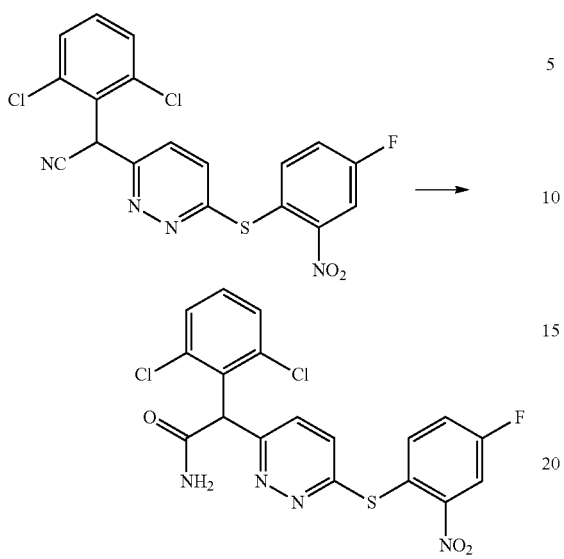

The nitrile product from Step A (142 mg, 0.33 mmol) was mixed with concentrated sulfuric acid (2 ml), heated to reflux for 1 hour and then allowed to cool to room temperature. The mixture was then diluted with ethyl acetate and carefully neutralized with saturated potassium carbonate solution (aqueous). The layers were separated and the organic layer was washed with water, brine and dried over magnesium sulfate. The mixture was filtered and evaporated to dryness. The residue was used in the next step without further purification (127 mg, 85% yield).

C.

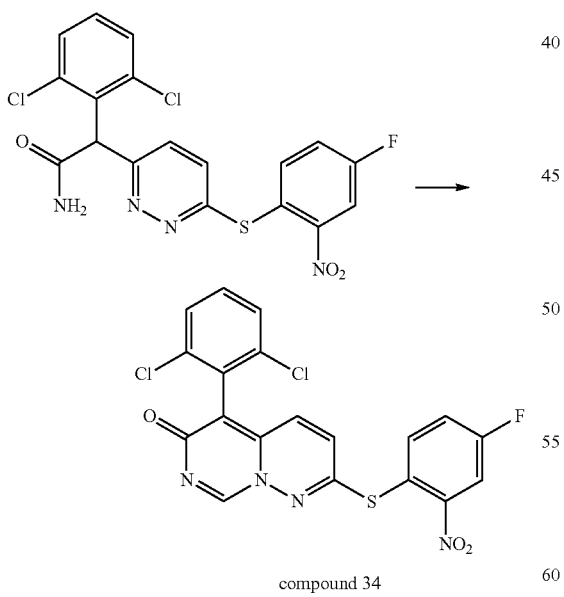

compound 34

The amide from the step B (127 mg, 0.28 mmol) was dissolved in THF (3 ml) and to this solution was added dimethylformamide dimethylacetal (110 μl, 0.83 mmol). The reaction was heated to reflux for 5 minutes then cooled to room temperature. All volatiles were removed in vacuo and the residue was flash chromatographed on silica gel eluting with 2.5% methanol in methylene chloride to yield pure desired compound 34 (118 mg, 92%).

D.

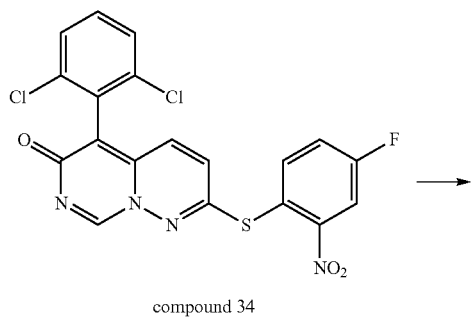

compound 34

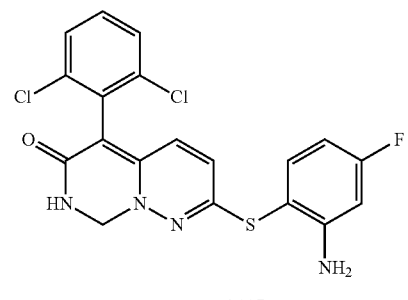

compound 117

A solution of nickel dichloride hexahydrate (103 mg, 0.44 mol) in a mixture of benzene/methanol (0.84 mL/0.84 ml) was added to a solution of compound 34 (100.8 mg, 0.22 mmol) in benzene (3.4 ml) and this solution was cooled to 0° C. To this solution was then added sodium borohydride (49 mg, 1.3 mmol). The reaction was stirred while allowing to warm to room temperature. The reaction was evaporated in vacuo and the residue was flash chromatographed eluting with 2% methanol in methylene chloride to yield pure desired product, compound 117 (21 mg, 25% yield).

Example 14

Synthesis of Compounds 53 and 142

A.

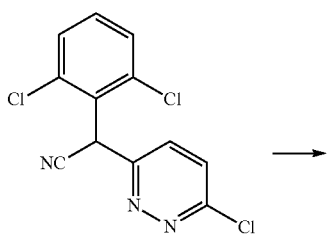

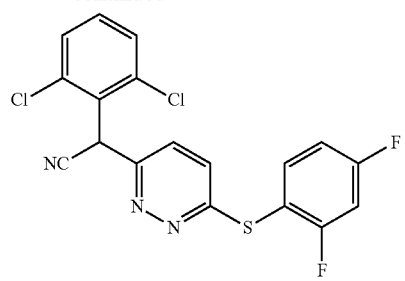

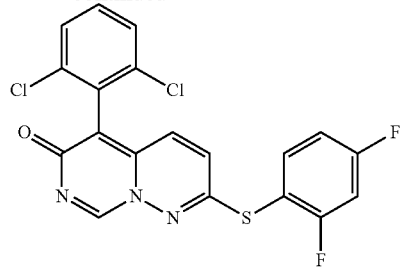

compound 53

The product indicated in the above reaction was synthesized using the procedure in example 1 step B using chloropyridazine (359 mg, 1.21 mmol) and 2,4 difluorothiophenol (176 mg, 1.21 mmol). The product was obtained after flash silica gel chromatography (451 mg, 92%).

The reaction above was carried out as described in Example 1, step D, using starting amide (410 mg, 0.96 mmol) and dimethylformamide dimethylacetal (3 mmol). The reaction was heated at 50° C. for 30 minutes and worked up as described previously. Compound 53 was obtained (313 mg, 75%).

B.

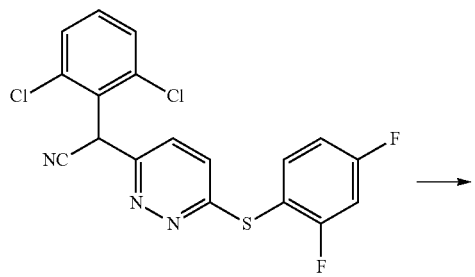

D.

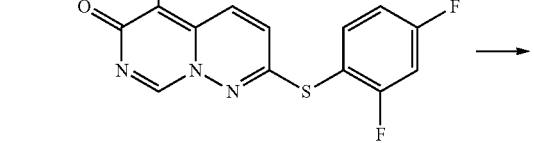

compound 53

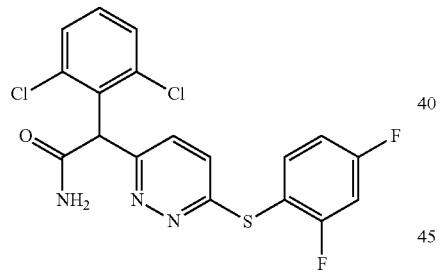

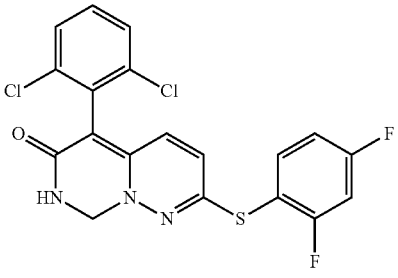

compound 142

The above reaction was carried out as described in Example 1, step C, using 451 mg of starting material and 5 ml of concentrated sulfuric acid to yield the indicated product (425 mg, 90%).

Compound 34 (213, 0.49 mmol) was dissolved in THF (10 ml), cooled to 0° C. and to this solution was added Borane in THF (1M, 0.6 mmol). The reaction was stirred for 30 minutes quenched with water and diluted with ethyl acetate. The organic layer was washed with water and brine, dried and rotovapped. The residue was purified on silica gel eluting with a gradient of 1% to 5% methanol in methylene chloride to afford compound 142 (125 mg, 57%).

Example 15

Cloning of p38 Kinase in Insect Cells

C.

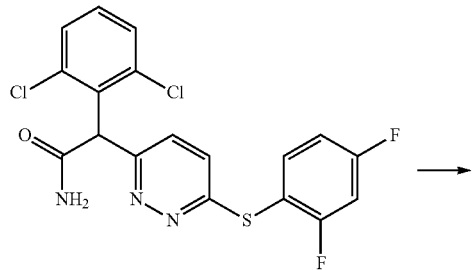

Two splice variants of human p38 kinase, CSBP1 and CSBP2, have been identified. Specific oligonucleotide primers were used to amplify the coding region of CSBP2 cDNA using a HeLa cell library (Stratagene) as a template. The polymerase chain reaction product was cloned into the pET- 15b vector (Novagen). The baculovirus transfer vector, pVL-(His)6-p38 was constructed by subcloning a XbaI-BamHI fragment of pET15b-(His)6-p38 into the complementary sites in plasmid pVL1392 (Pharmingen).

The plasmid pVL-(His)6-p38 directed the synthesis of a recombinant protein consisting of a 23-residue peptide (MGSSHHHHHHSSGLVPRGSHMLE, where LVPRGS represents a thrombin cleavage site) fused in frame to the N-terminus of p38, as confirmed by DNA sequencing and by N-terminal sequencing of the expressed protein. Monolayer culture of Spodoptera frugiperda (Sf9) insect cells (ATCC) was maintained in TNM-FH medium (Gibco BRL) supplemented with 10% fetal bovine serum in a T-flask at 27° C. Sf9 cells in log phase were co-transfected with linear viral DNA of Autographa califonica nuclear polyhedrosis virus (Pharmingen) and transfer vector pVL-(His)6-p38 using Lipofectin (Invitrogen). The individual recombinant baculovirus clones were purified by plaque assay using 1% low melting agarose.

Example 16

Expression and Purification of Recombinant p38 Kinase

Trichoplusia ni (Tn-368) High-Five™ cells (Invitrogen) were grown in suspension in Excel-405 protein free medium (JRH Bioscience) in a shaker flask at 27° C. Cells at a density of $1.5 \times 10^6$ cells/ml were infected with the recombinant baculovirus described above at a multiplicity of infection of 5. The expression level of recombinant p38 was monitored by immunoblotting using a rabbit anti-p38 antibody (Santa Cruz Biotechnology). The cell mass was harvested 72 hours after infection when the expression level of p38 reached its maximum.

Frozen cell paste from cells expressing the $(His)_6$-tagged p38 was thawed in 5 volumes of Buffer A (50 mM NaH2PO4 pH 8.0, 200 mM NaCl, 2 mM β-Mercaptoethanol, 10% Glycerol and 0.2 mM PMSF). After mechanical disruption of the cells in a microfluidizer, the lysate was centrifuged at 30,000×g for 30 minutes. The supernatant was incubated batchwise for 3-5 hours at 4° C. with Talon™ (Clontech) metal affinity resin at a ratio of 1 ml of resin per 2-4 mgs of expected p38. The resin was settled by centrifugation at 500×g for 5 minutes and gently washed batchwise with Buffer A. The resin was slurried and poured into a column (approx. 2.6×5.0 cm) and washed with Buffer A+5 mM imidazole.

The $(His)_6$-p38 was eluted with Buffer A+100 mM imidazole and subsequently dialyzed overnight at 4° C. against 2 liters of Buffer B, (50 mM HEPES, pH 7.5, 25 mM β-glycerophosphate, 5% glycerol, 2 mM DTT). The $His_6$ tag was removed by addition of at 1.5 units thrombin (Calbiochem) per mg of p38 and incubation at 20° C. for 2-3 hours. The thrombin was quenched by addition of 0.2 mM PMSF and then the entire sample was loaded onto a 2 ml benzamidine agarose (American International Chemical) column.

The flow through fraction was directly loaded onto a 2.6× 5.0 cm Q-Sepharose (Pharmacia) column previously equilibrated in Buffer B+0.2 mM PMSF. The p38 was eluted with a 20 column volume linear gradient to 0.6M NaCl in Buffer B. The eluted protein peak was pooled and dialyzed overnight at 4° C. vs. Buffer C (50 mM HEPES pH 7.5, 5% glycerol, 50 mM NaCl, 2 mM DTT, 0.2 mM PMSF).

The dialyzed protein was concentrated in a Centriprep (Amicon) to 3-4 ml and applied to a 2.6×100 cm Sephacryl S-100HR (Pharmacia) column. The protein was eluted at a flow rate of 35 ml/hr. The main peak was pooled, adjusted to 20 mM DTT, concentrated to 10-80 mgs/ml and frozen in aliquots at −70° C. or used immediately.

Example 17

Activation of p38

P38 was activated by combining 0.5 mg/ml p38 with 0.005 mg/ml DD-double mutant MKK6 in Buffer B+10 mM MgCl2, 2 mM ATP, 0.2 mM Na2VO4 for 30 minutes at 20° C. The activation mixture was then loaded onto a 1.0×10 cm MonoQ column (Pharmacia) and eluted with a linear 20 column volume gradient to 1.0 M NaCl in Buffer B. The activated p38 eluted after the ADP and ATP. The activated p38 peak was pooled and dialyzed against buffer B+0.2 mM Na2VO4 to remove the NaCl. The dialyzed protein was adjusted to 1.1M potassium phosphate by addition of a 4.0M stock solution and loaded onto a 1.0×10 cm HIC (Rainin Hydropore) column previously equilibrated in Buffer D (10% glycerol, 20 mM β-glycerophosphate, 2.0 mM DTT)+ 1.1MK2HPO4. The protein was eluted with a 20 column volume linear gradient to Buffer D+50 mM K2HPO4. The double phosphorylated p38 eluted as the main peak and was pooled for dialysis against Buffer B+0.2 mM Na2VO4. The activated p38 was stored at −70° C.

Example 18

P38 Inhibition Assays

A. Inhibition of Phosphorylation of EGF Receptor Peptide

This assay was carried out in the presence of 10 mM MgCl2, 25 mM β-glycerophosphate, 10% glycerol and 100 mM HEPES buffer at pH 7.6. For a typical IC50 determination, a stock solution was prepared containing all of the above components and activated p38 (5 nM). The stock solution was aliquotted into vials. A fixed volume of DMSO or inhibitor in DMSO (final concentration of DMSO in reaction was 5%) was introduced to each vial, mixed and incubated for 15 minutes at room temperature. EGF receptor peptide, KRELVEPLTPSGEAPNQALLR, a phosphoryl acceptor in p38-catalyzed kinase reaction (1), was added to each vial to a final concentration of 200 µM. The kinase reaction was initiated with ATP (100 µM) and the vials were incubated at 30° C. After 30 minutes, the reactions were quenched with equal volume of 10% trifluoroacetic acid (TFA).

The phosphorylated peptide was quantified by HPLC analysis. Separation of phosphorylated peptide from the unphosphorylated peptide was achieved on a reverse phase column (Deltapak, 5 µm, C18 100D, part no. 011795) with a binary gradient of water and actenitrile, each containing 0.1% TFA. IC50 (concentration of inhibitor yielding 50% inhibition) was determined by plotting the % activity remaining against inhibitor concentration.

B. Inhibition of ATPase Activity

This assay was carried out in the presence of 10 mM MgCl2, 25 mM β-glycerophosphate, 10% glycerol and 100 mM HEPES buffer at pH 7.6. For a typical Ki determination, the Km for ATP in the ATPase activity of activated p38 reaction was determined in the absence of inhibitor and in the presence of two concentrations of inhibitor. A stock solution was prepared containing all of the above components and activated p38 (60 nM). The stock solution was aliquotted into vials. A fixed volume of DMSO or inhibitor in DMSO (final concentration of DMSO in reaction was 2.5%) was introduced to each vial, mixed and incubated for 15 minutes at room temperature. The reaction was initiated by adding various concentrations of ATP and then incubated at 30° C. After 30 minutes, the reactions were quenched with 50 µl of EDTA (0.1 M, final concentration), pH 8.0. The product of p38 ATPase activity, ADP, was quantified by HPLC analysis.

Separation of ADP from ATP was achieved on a reversed phase column (Supelcosil, LC-18, 3 µm, part no. 5-8985) using a binary solvent gradient of following composition: Solvent A—0.1 M phosphate buffer containing 8 mM tetrabutylammonium hydrogen sulfate (Sigma Chemical Co., catalogue no. T-7158), Solvent B—Solvent A with 30% methanol.

Ki was determined from the rate data as a function of inhibitor and ATP concentrations. The results for several of the inhibitors of this invention are depicted in Table 6 below:

TABLE 6

| Compound | $K_i$ (µM) |
| --- | --- |
| 1 | >20 |
| 2 | 15 |
| 3 | 5.0 |
| 5 | 2.9 |
| 6 | 0.4 |

Other p38 inhibitors of this invention will also inhibit the ATPase activity of p38.

C. Inhibition of IL-1, TNF, IL-6 and IL-8
Production in LPS-Stimulated PBMCs

Inhibitors were serially diluted in DMSO from a 20 mM stock. At least 6 serial dilutions were prepared. Then 4× inhibitor stocks were prepared by adding 4 µl of an inhibitor dilution to 1 ml of RPMI1640 medium/10% fetal bovine serum. The 4× inhibitor stocks contained inhibitor at concentrations of 80 µM, 32 µM, 12.8 µM, 5.12 µM, 2.048 µM, 0.819 µM, 0.328 µM, 0.131 µM, 0.052 µM, 0.021 µM etc. The 4× inhibitor stocks were pre-warmed at 37° C. until use.

Fresh human blood buffy cells were separated from other cells in a Vacutainer CPT from Becton & Dickinson (containing 4 ml blood and enough DPBS without $Mg^{2+}/Ca^{2+}$ to fill the tube) by centrifugation at 1500×g for 15 min. Peripheral blood mononuclear cells (PBMCs), located on top of the gradient in the Vacutainer, were removed and washed twice with RPMI1640 medium/10% fetal bovine serum. PBMCs were collected by centrifugation at 500×g for 10 min. The total cell number was determined using a Neubauer Cell Chamber and the cells were adjusted to a concentration of $4.8 \times 10^6$ cells/ml in cell culture medium (RPMI1640 supplemented with 10% fetal bovine serum).

Alternatively, whole blood containing an anti-coagulant was used directly in the assay.

We placed 100 µl of cell suspension or whole blood in each well of a 96-well cell culture plate. Then we added 50 µl of the 4× inhibitor stock to the cells. Finally, we added 50 µl of a lipopolysaccharide (LPS) working stock solution (16 ng/ml in cell culture medium) to give a final concentration of 4 ng/ml LPS in the assay. The total assay volume of the vehicle control was also adjusted to 200 µl by adding 50 µl cell culture medium. The PBMC cells or whole blood were then incubated overnight (for 12-15 hours) at 37° C./5% $CO_2$ in a humidified atmosphere.

The next day the cells were mixed on a shaker for 3-5 minutes before centrifugation at 500×g for 5 minutes. Cell culture supernatants were harvested and analyzed by ELISA for levels of IL-1b (R & D Systems, Quantikine kits, #DBL50), TNF-∀ (BioSource, #KHC3012), IL-6 (Endogen, #EH2-IL6) and IL-8 (Endogen, #EH2-IL8) according to the instructions of the manufacturer. The ELISA data were used to generate dose-response curves from which IC50 values were derived.

Results for the kinase assay ("kinase"; subsection A, above), IL-1 and TNF in LPS-stimulated PBMCs ("cell") and IL-1, TNF and IL-6 in whole blood ("WB") for various p38 inhibitors of this invention are shown in Table 7 below:

| cmpd # | kinase IC50 | cell IL-1 IC50 | cell TNF IC50 | WB IL-1 IC50 | WB TNF IC50 | WB IL-6 IC50 |
| --- | --- | --- | --- | --- | --- | --- |
| 2 | + | N.D. | N.D. | N.D. | N.D. | N.D. |
| 3 | + | N.D. | N.D. | N.D. | N.D. | N.D. |
| 5 | + | N.D. | N.D. | N.D. | N.D. | N.D. |
| 6 | ++ | ++ | + | N.D. | N.D. | N.D. |
| 7 | + | + | + | N.D. | N.D. | N.D. |
| 8 | + | + | + | N.D. | N.D. | N.D. |
| 9 | + | + | + | N.D. | N.D. | N.D. |
| 10 | + | N.D. | N.D. | N.D. | N.D. | N.D. |
| 11 | + | + | + | N.D. | N.D. | N.D. |
| 12 | ++ | ++ | ++ | + | + | + |
| 13 | + | + | + | N.D. | N.D. | N.D. |
| 14 | + | ++ | + | N.D. | N.D. | N.D. |
| 15 | + | ++ | ++ | N.D. | N.D. | N.D. |
| 16 | ++ | + | ++ | N.D. | N.D. | N.D. |
| 17 | + | + | + | N.D. | N.D. | N.D. |
| 18 | + | + | + | N.D. | N.D. | N.D. |
| 19 | + | + | + | N.D. | N.D. | N.D. |
| 20 | ++ | + | + | N.D. | N.D. | N.D. |
| 21 | ++ | ++ | + | N.D. | N.D. | N.D. |
| 22 | + | + | + | N.D. | N.D. | N.D. |
| 23 | ++ | ++ | + | + | + | + |
| 24 | ++ | ++ | ++ | + | + | N.D. |
| 25 | ++ | ++ | + | N.D. | N.D. | N.D. |
| 26 | + | +++ | ++ | + | + | + |
| 27 | ++ | + | + | + | + | + |
| 28 | ++ | ++ | ++ | N.D. | N.D. | N.D. |
| 29 | ++ | ++ | ++ | N.D. | N.D. | N.D. |
| 30 | + | + | + | + | N.D. | N.D. |
| 31 | + | + | + | N.D. | N.D. | N.D. |
| 32 | ++ | + | ++ | + | + | + |
| 33 | ++ | ++ | ++ | + | + | + |
| 34 | + | + | + | N.D. | N.D. | N.D. |
| 35 | ++ | ++ | + | + | + | + |
| 36 | + | + | + | + | + | + |
| 37 | ++ | ++ | + | + | + | + |
| 38 | +++ | +++ | ++ | ++ | ++ | ++ |
| 39 | ++ | + | + | N.D. | N.D. | N.D. |
| 40 | ++ | ++ | + | N.D. | N.D. | N.D. |
| 41 | +++ | +++ | +++ | N.D. | N.D. | N.D. |
| 42 | + | N.D. | N.D. | N.D. | N.D. | N.D. |
| 43 | ++ | + | + | N.D. | N.D. | N.D. |
| 44 | ++ | + | + | N.D. | N.D. | N.D. |
| 45 | ++ | N.D. | N.D. | N.D. | N.D. | N.D. |
| 46 | ++ | + | + | N.D. | N.D. | N.D. |
| 47 | ++ | ++ | + | N.D. | N.D. | N.D. |
| 48 | ++ | ++ | + | N.D. | N.D. | N.D. |
| 49 | ++ | +++ | + | + | + | + |
| 50 | + | N.D. | N.D. | N.D. | N.D. | N.D. |
| 51 | ++ | N.D. | N.D. | N.D. | N.D. | N.D. |
| 52 | ++ | N.D. | N.D. | N.D. | N.D. | N.D. |
| 53 | +++ | +++ | +++ | +++ | +++ | +++ |
| 101 | ++ | +++ | +++ | + | + | ++ |
| 102 | +++ | +++ | +++ | + | ++ | ++ |
| 103 | +++ | +++ | +++ | + | ++ | ++ |
| 104 | ++ | ++ | ++ | + | + | + |
| 105 | ++ | + | + | N.D. | N.D. | N.D. |
| 106 | +++ | +++ | +++ | + | ++ | ++ |
| 107 | ++ | + | + | N.D. | N.D. | N.D. |
| 109 | +++ | +++ | +++ | + | + | ++ |
| 108 | +++ | ++ | +++ | ++ | +++ | +++ |
| 110 | ++ | + | + | N.D. | N.D. | N.D. |
| 111 | ++ | + | + | N.D. | N.D. | N.D. |
| 112 | ++ | ++ | + | + | + | + |
| 113 | +++ | +++ | ++ | + | + | + |
| 114 | +++ | +++ | +++ | ++ | ++ | +++ |
| 115 | +++ | +++ | +++ | + | + | + |
| 116 | +++ | +++ | ++ | + | + | + |

-continued

| cmpd # | kinase IC50 | cell IL-1 IC50 | cell TNF IC50 | WB IL-1 IC50 | WB TNF IC50 | WB IL-6 IC50 |
|---|---|---|---|---|---|---|
| 117 | +++ | +++ | +++ | ++ | ++ | +++ |
| 118 | ++ | ++ | ++ | + | + | + |
| 119 | ++ | N.D. | N.D. | N.D. | N.D. | N.D. |
| 120 | N.D. | ++ | + | + | + | + |
| 121 | +++ | +++ | ++ | + | + | + |
| 122 | ++ | ++ | + | + | + | + |
| 123 | ++ | ++ | ++ | + | + | + |
| 124 | + | + | + | N.D. | N.D. | N.D. |
| 125 | +++ | +++ | +++ | + | + | + |
| 126 | + | ++ | + | N.D. | N.D. | N.D. |
| 127 | +++ | +++ | +++ | ++ | ++ | +++ |
| 128 | + | + | + | N.D. | N.D. | N.D. |
| 129 | +++ | +++ | +++ | ++ | + | ++ |
| 130 | +++ | ++ | + | N.D. | N.D. | N.D. |
| 131 | +++ | +++ | +++ | N.D. | N.D. | N.D. |
| 132 | +++ | +++ | ++ | N.D. | N.D. | N.D. |
| 133 | +++ | +++ | +++ | N.D. | N.D. | N.D. |
| 134 | +++ | ++ | + | N.D. | N.D. | N.D. |
| 135 | +++ | ++ | + | + | + | + |
| 136 | +++ | +++ | +++ | + | + | ++ |
| 137 | +++ | +++ | ++ | + | + | ++ |
| 138 | ++ | +++ | ++ | + | + | +++ |
| 139 | +++ | +++ | + | + | + | + |
| 140 | +++ | +++ | +++ | ++ | + | ++ |
| 141 | +++ | +++ | +++ | + | + | + |
| 142 | +++ | +++ | +++ | +++ | +++ | +++ |
| 143 | +++ | +++ | ++ | + | + | + |
| 144 | +++ | +++ | ++ | + | + | ++ |
| 145 | +++ | +++ | +++ | +++ | +++ | +++ |
| 201 | ++ | + | + | + | +++ | + |
| 203 | + | N.D. | N.D. | N.D. | N.D. | N.D. |
| 204 | + | N.D. | N.D. | N.D. | N.D. | N.D. |
| 205 | + | N.D. | N.D. | N.D. | N.D. | N.D. |
| 206 | ++ | + | + | N.D. | N.D. | N.D. |
| 207 | + | N.D. | N.D. | N.D. | N.D. | N.D. |
| 208 | N.D. | ++ | N.D. | N.D. | N.D. | N.D. |
| 209 | N.D. | + | N.D. | N.D. | N.D. | N.D. |
| 202 | +++ | ++ | ++ | + | + | + |
| 301 | | | | | | |
| 302 | +++ | +++ | ++ | + | + | + |
| 303 | + | + | + | + | + | + |
| 304 | + | + | + | + | + | + |
| 305 | +++ | +++ | + | + | + | + |
| 306 | ++ | ++ | + | + | + | + |
| 307 | +++ | ++ | + | + | + | + |
| 308 | + | N.D. | N.D. | N.D. | N.D. | N.D. |
| 309 | ++ | ++ | ++ | + | + | + |
| 310 | ++ | + | + | N.D. | N.D. | N.D. |
| 311 | ++ | + | + | N.D. | N.D. | N.D. |
| 312 | +++ | ++ | + | + | + | + |
| 313 | ++ | + | N.D. | N.D. | N.D. | N.D. |
| 314 | + | N.D. | N.D. | N.D. | N.D. | N.D. |
| 315 | + | N.D. | N.D. | N.D. | N.D. | N.D. |
| 316 | + | N.D. | N.D. | N.D. | N.D. | N.D. |
| 317 | + | + | + | N.D. | N.D. | N.D. |
| 318 | ++ | + | + | N.D. | N.D. | N.D. |
| 319 | + | N.D. | N.D. | N.D. | N.D. | N.D. |
| 320 | +++ | ++ | ++ | N.D. | N.D. | N.D. |
| 321 | + | N.D. | N.D. | N.D. | N.D. | N.D. |
| 322 | ++ | + | + | N.D. | N.D. | N.D. |
| 323 | ++ | ++ | ++ | N.D. | N.D. | N.D. |
| 324 | ++ | ++ | + | N.D. | N.D. | N.D. |
| 325 | +++ | +++ | ++ | + | + | + |
| 326 | + | N.D. | N.D. | N.D. | N.D. | N.D. |
| 327 | ++ | N.D. | N.D. | N.D. | N.D. | N.D. |
| 328 | + | N.D. | N.D. | N.D. | N.D. | N.D. |
| 329 | ++ | ++ | + | + | + | + |
| 330 | + | N.D. | N.D. | N.D. | N.D. | N.D. |
| 331 | + | N.D. | N.D. | N.D. | N.D. | N.D. |
| 332 | ++ | ++ | + | + | + | + |
| 333 | ++ | + | N.D. | N.D. | N.D. | N.D. |
| 334 | + | N.D. | N.D. | N.D. | N.D. | N.D. |
| 335 | ++ | + | N.D. | N.D. | N.D. | N.D. |
| 336 | + | N.D. | N.D. | N.D. | N.D. | N.D. |
| 337 | + | N.D. | N.D. | N.D. | N.D. | N.D. |
| 338 | + | N.D. | N.D. | N.D. | N.D. | N.D. |
| 339 | + | N.D. | N.D. | N.D. | N.D. | N.D. |

-continued

| cmpd # | kinase IC50 | cell IL-1 IC50 | cell TNF IC50 | WB IL-1 IC50 | WB TNF IC50 | WB IL-6 IC50 |
|---|---|---|---|---|---|---|
| 340 | + | N.D. | N.D. | N.D. | N.D. | N.D. |
| 341 | ++ | ++ | ++ | N.D. | N.D. | N.D. |
| 342 | + | N.D. | N.D. | N.D. | N.D. | N.D. |
| 343 | + | N.D. | N.D. | N.D. | N.D. | N.D. |
| 344 | + | N.D. | N.D. | N.D. | N.D. | N.D. |
| 345 | + | N.D. | N.D. | N.D. | N.D. | N.D. |
| 346 | ++ | + | + | + | + | + |
| 347 | + | N.D. | N.D. | N.D. | N.D. | N.D. |
| 348 | + | N.D. | N.D. | N.D. | N.D. | N.D. |
| 349 | + | ++ | + | + | + | + |
| 350 | + | ++ | + | N.D. | N.D. | N.D. |
| 351 | + | + | + | N.D. | N.D. | N.D. |
| 352 | + | + | N.D. | N.D. | N.D. | N.D. |
| 353 | ++ | + | + | N.D. | N.D. | N.D. |
| 354 | + | N.D. | N.D. | N.D. | N.D. | N.D. |
| 355 | + | N.D. | N.D. | N.D. | N.D. | N.D. |
| 356 | + | N.D. | N.D. | N.D. | N.D. | N.D. |
| 357 | + | N.D. | N.D. | N.D. | N.D. | N.D. |
| 358 | ++ | + | + | N.D. | N.D. | N.D. |
| 359 | + | N.D. | N.D. | N.D. | N.D. | N.D. |
| 360 | + | N.D. | N.D. | N.D. | N.D. | N.D. |
| 361 | ++ | ++ | + | N.D. | N.D. | N.D. |
| 362 | +++ | ++ | ++ | + | + | + |
| 363 | +++ | +++ | ++ | + | + | + |
| 364 | +++ | +++ | ++ | + | + | + |
| 365 | N.D. | N.D. | N.D. | N.D. | N.D. | N.D. |
| 366 | + | N.D. | N.D. | N.D. | N.D. | N.D. |
| 367 | N.D. | N.D. | N.D. | N.D. | N.D. | N.D. |
| 368 | N.D. | N.D. | N.D. | N.D. | N.D. | N.D. |
| 369 | N.D. | N.D. | N.D. | N.D. | N.D. | N.D. |
| 370 | N.D. | N.D. | N.D. | N.D. | N.D. | N.D. |
| 371 | N.D. | N.D. | N.D. | N.D. | N.D. | N.D. |
| 372 | N.D. | N.D. | N.D. | N.D. | N.D. | N.D. |
| 373 | N.D. | N.D. | N.D. | N.D. | N.D. | N.D. |
| 374 | ++ | N.D. | N.D. | N.D. | N.D. | N.D. |
| 375 | +++ | N.D. | N.D. | N.D. | N.D. | N.D. |
| 376 | +++ | N.D. | N.D. | N.D. | N.D. | N.D. |
| 377 | +++ | N.D. | N.D. | N.D. | N.D. | N.D. |
| 378 | +++ | N.D. | N.D. | N.D. | N.D. | N.D. |
| 379 | +++ | N.D. | N.D. | N.D. | N.D. | N.D. |
| 380 | ++ | N.D. | N.D. | N.D. | N.D. | N.D. |
| 381 | ++ | N.D. | N.D. | N.D. | N.D. | N.D. |
| 382 | +++ | N.D. | N.D. | N.D. | N.D. | N.D. |
| 383 | +++ | N.D. | N.D. | N.D. | N.D. | N.D. |
| 384 | ++ | N.D. | N.D. | N.D. | N.D. | N.D. |
| 385 | ++ | N.D. | N.D. | N.D. | N.D. | N.D. |
| 386 | + | N.D. | N.D. | N.D. | N.D. | N.D. |
| 387 | + | N.D. | N.D. | N.D. | N.D. | N.D. |
| 388 | +++ | N.D. | N.D. | N.D. | N.D. | N.D. |
| 389 | ++ | N.D. | N.D. | N.D. | N.D. | N.D. |
| 390 | + | N.D. | N.D. | N.D. | N.D. | N.D. |
| 391 | ++ | N.D. | N.D. | N.D. | N.D. | N.D. |
| 392 | ++ | N.D. | N.D. | N.D. | N.D. | N.D. |
| 393 | ++ | N.D. | N.D. | N.D. | N.D. | N.D. |
| 394 | +++ | N.D. | N.D. | N.D. | N.D. | N.D. |
| 395 | +++ | N.D. | N.D. | N.D. | N.D. | N.D. |
| 396 | +++ | N.D. | N.D. | N.D. | N.D. | N.D. |
| 397 | + | N.D. | N.D. | N.D. | N.D. | N.D. |
| 398 | N.D. | N.D. | N.D. | N.D. | N.D. | N.D. |
| 399 | +++ | N.D. | N.D. | N.D. | N.D. | N.D. |
| 1301 | +++ | N.D. | N.D. | N.D. | N.D. | N.D. |
| 401 | +++ | ++ | ++ | + | + | + |
| 402 | +++ | +++ | +++ | + | + | + |
| 403 | +++ | +++ | +++ | + | + | ++ |
| 404 | +++ | +++ | +++ | + | + | + |
| 405 | +++ | +++ | ++ | N.D. | N.D. | N.D. |
| 406 | ++ | ++ | + | N.D. | N.D. | N.D. |
| 407 | ++ | ++ | + | N.D. | N.D. | N.D. |
| 408 | +++ | +++ | ++ | N.D. | N.D. | N.D. |
| 409 | +++ | +++ | +++ | + | + | ++ |

-continued

| cmpd # | kinase IC50 | cell IL-1 IC50 | cell TNF IC50 | WB IL-1 IC50 | WB TNF IC50 | WB IL-6 IC50 |
|---|---|---|---|---|---|---|
| 410 | +++ | +++ | +++ | ++ | ++ | ++ |
| 411 | +++ | +++ | +++ | + | + | + |
| 412 | N.D. | N.D. | N.D. | N.D. | N.D. | N.D. |

For kinase IC50 values, "+++" represents <0.1 µM, "++" represents between 0.1 and 1.0 µM, and "+" represents >1.0 µM.
For cellular IL-1 and TNF values, "+++" represents <0.1 µM, "++" represents between 0.1 and 0.5 µM, and "+" represents >0.5 µM.
For all whole blood ("WB") assay values, "+++" represents <0.25 µM, "++" represents between 0.25 and 0.5 µM, and "+" represents >0.5 µM.
In all assays indicated in the table above, "N.D." represents value not determined.

Other p38 inhibitors of this invention will also inhibit phosphorylation of EGF receptor peptide, and the production of IL-1, TNF and IL-6, as well as IL-8 in LPS-stimulated PBMCs or in whole blood.

D. Inhibition of IL-6 and IL-8
Production in IL-1-Stimulated PBMCs

This assay was carried out on PBMCs exactly the same as above except that 50 µl of an IL-1b working stock solution (2 ng/ml in cell culture medium) was added to the assay instead of the (LPS) working stock solution.

Cell culture supernatants were harvested as described above and analyzed by ELISA for levels of IL-6 (Endogen, #EH2-IL6) and IL-8 (Endogen, #EH2-IL8) according to the instructions of the manufacturer. The ELISA data were used to generate dose-response curves from which IC50 values were derived.

Results for p38 inhibitor compound 6 are shown in Table 8 below:

TABLE 8

| Cytokine assayed | IC$_{50}$ (µM) |
|---|---|
| IL-6 | 0.60 |
| IL-8 | 0.85 |

E. Inhibition of LPS-Induced
Prostaglandin Endoperoxide Synthase-2
(PGHS-2, or COX-2) Induction In PBMCs Human peripheral mononuclear cells (PBMCs) were isolated from fresh human blood buffy coats by centrifugation in a Vacutainer CPT (Becton & Dickinson). We seeded 15×10$^6$ cells in a 6-well tissue culture dish containing RPMI 1640 supplemented with 10% fetal bovine serum, 50 U/ml penicillin, 50 µg/ml streptomycin, and 2 mM L-glutamine. Compound 6 (above) was added at 0.2, 2.0 and 20 µM final concentrations in DMSO. Then we added LPS at a final concentration of 4 ng/ml to induce enzyme expression. The final culture volume was 10 ml/well.

After overnight incubation at 37° C., 5% CO$_2$, the cells were harvested by scraping and subsequent centrifugation, then the supernatant was removed, and the cells were washed twice in ice-cold DPBS (Dulbecco's phosphate buffered saline, BioWhittaker). The cells were lysed on ice for 10 min in 50 µl cold lysis buffer (20 mM Tris-HCl, pH 7.2, 150 mM NaCl, 1% Triton-X-100, 1% deoxycholic acid, 0.1% SDS, 1 mM EDTA, 2% aprotinin (Sigma), 10 µg/ml pepstatin, 10 µg/ml leupeptin, 2 mM PMSF, 1 mM benzamidine, 1 mM DTT) containing 1 µl Benzonase (DNAse from Merck). The protein concentration of each sample was determined using the BCA assay (Pierce) and bovine serum albumin as a standard. Then the protein concentration of each sample was adjusted to 1 mg/ml with cold lysis buffer. To 100 µl lysate an equal volume of 2×SDS PAGE loading buffer was added and the sample was boiled for 5 min. Proteins (30 µg/lane) were size-fractionated on 4-20% SDS PAGE gradient gels (Novex) and subsequently transferred onto nitrocellulose membrane by electrophoretic means for 2 hours at 100 mA in Towbin transfer buffer (25 mM Tris, 192 mM glycine) containing 20% methanol. The membrane was pretreated for 1 hour at room temperature with blocking buffer (5% non-fat dry milk in DPBS supplemented with 0.1% Tween-20) and washed 3 times in DPBS/0.1% Tween-20. The membrane was incubated overnight at 4° C. with a 1:250 dilution of monoclonal anti-COX-2 antibody (Transduction Laboratories) in blocking buffer. After 3 washes in DPBS/0.1% Tween-20, the membrane was incubated with a 1:1000 dilution of horseradish peroxidase-conjugated sheep antiserum to mouse Ig (Amersham) in blocking buffer for 1 h at room temperature. Then the membrane was washed again 3 times in DPBS/0.1% Tween-20 and an ECL detection system (SuperSignal™ CL-HRP Substrate System, Pierce) was used to determine the levels of expression of COX-2.

Results of the above mentioned assay indicate that compound 6 inhibits LPS induced PGHS-2 expression in PBMCs.

While we have hereinbefore presented a number of embodiments of this invention, it is apparent that our basic construction can be altered to provide other embodiments which utilize the methods of this invention.

The invention claimed is:
1. A compound of the formula:

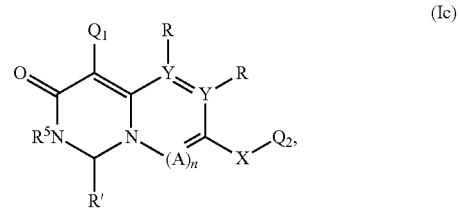

(Ic)

or a pharmaceutically acceptable salt thereof, wherein:
each of $Q_1$ and $Q_2$ are independently selected from 5-6 membered aromatic carbocyclic or heterocyclic ring systems, or 8-10 membered bicyclic ring systems consisting of aromatic carbocyclic rings, aromatic heterocyclic rings or a combination of an aromatic carbocyclic ring and an aromatic heterocyclic ring; wherein:
$Q_1$ is substituted with 1 to 4 substituents, independently selected from halo; $C_1$-$C_3$ alkyl optionally substituted with NR'$_2$, OR', CO$_2$R' or CONR'$_2$; O—($C_1$-$C_3$)-alkyl optionally substituted with NR'$_2$, OR', CO$_2$R' or CONR'$_2$; NR'$_2$; OCF$_3$; CF$_3$; NO$_2$; CO$_2$R'; CON(R')$_2$; SR'; S(O$_2$)N(R')$_2$; SCF$_3$; CN; N(R')C(O)R$^4$; N(R')C(O)OR$^4$; N(R')C(O)C(O)R$^4$; N(R')S(O$_2$)R$^4$; N(R')R$^4$; N(R$^4$)$_2$; OR$^4$; OC(O)R$^4$; OP(O)$_3$H$_2$; N=CH—N(R')$_2$; 3,4-methylenedioxy; —NH—C(O)—O—CH$_2$-4-pyridine; —NH—C(O)CH$_2$-morpholine; —NH—C(O)CH$_2$-piperazine; or —NH—C(O)CH$_2$-pyrrolidine; and
$Q_2$ is optionally substituted with up to 4 substituents, independently selected from halo; $C_1$-$C_3$ straight or branched alkyl optionally substituted with NR'$_2$, OR', CO$_2$R', S(O$_2$)N(R')$_2$, N=CH—N(R')$_2$, R$^3$, or CONR'$_2$; O—($C_1$-$C_3$)-alkyl optionally substituted with NR'$_2$, OR', CO$_2$R', S(O$_2$)N(R')$_2$, N=CH—N(R')$_2$, R$^3$, or CONR'$_2$; NR'$_2$; OCF$_3$; CF$_3$; NO$_2$; CO$_2$R'; CON(R')$_2$; R$^3$; OR$^3$; NHR$^3$; SR$^3$; C(O)R$^3$; C(O)N(R')R$^3$; C(O)OR$^3$; SR'; S(O$_2$)N(R')$_2$; SCF$_3$; N=CH—N(R')$_2$; CN; —NH—C(=NH)—NH$_2$; —CH$_2$—NH—C(=NH)—NH$_2$; or —CH$_2$—NH-imidazole;

wherein R' is selected from hydrogen, (C$_1$-C$_3$)-alkyl; (C$_2$-C$_3$)-alkenyl or alkynyl; phenyl or phenyl substituted with 1 to 3 substituents independently selected from halo, methoxy, cyano, nitro, amino, hydroxy, methyl or ethyl;

R$^3$ is selected from a 5-6 membered aromatic carbocyclic or heterocyclic ring system; and R$^4$ is (C$_1$-C$_4$)-alkyl optionally substituted with N(R')$_2$, OR', CO$_2$R', CON(R')$_2$, or SO$_2$N(R$^2$)$_2$; or a 5-6 membered carbocyclic or heterocyclic ring system optionally substituted with N(R')$_2$, OR', CO$_2$R', CON(R')$_2$, or SO$_2$N(R$^2$)$_2$;

X is selected from —S—, —O—, —S(O$_2$)—, —S(O)—, —S(O$_2$)—N(R$^2$)—, —N(R$^2$)—S(O$_2$)—, —N(R$^2$)—C(O)O—, —O—C(O)—N(R$^2$), —C(O)—, —C(O)O—, —O—C(O)—, —C(O)—N(R$^2$)—, —N(R$^2$)—C(O)—, —N(R$^2$)—, —C(R$^2$)$_2$—, or —C(OR$^2$)$_2$—;

each R is independently selected from hydrogen, —R$^2$, —N(R$^2$)$_2$, —OR$^2$, SR$^2$, —C(O)—N(R$^2$)$_2$, —S(O$_2$)—N(R$^2$)$_2$, or —C(O)—OR$^2$, wherein two adjacent R are optionally bound to one another and, together with each Y to which they are respectively bound, form a 4-8 membered carbocyclic or heterocyclic ring;

R$^2$ is selected from hydrogen, (C$_1$-C$_3$)-alkyl, or (C$_2$-C$_3$)-alkenyl; each optionally substituted with —N(R')$_2$, —OR', SR', —C(O)—N(R')$_2$, —S(O$_2$)—N(R')$_2$, —C(O)—OR', or R$^3$;

Y is C;

A, if present, is N;

n is 0 or 1; and

R$^5$ is selected from hydrogen, —CR'$_2$OH, —C(O)R$^4$, —C(O)OR$^4$, —CR'$_2$OPO$_3$H$_2$, and —PO$_3$H$_2$.

2. The compound according to claim 1, wherein Q$_1$ is selected from phenyl or pyridyl containing 1 to 3 substituents independently selected from chloro, fluoro, bromo, —CH$_3$, —OCH$_3$, —OH, —CF$_3$, —OCF$_3$, —O(CH$_2$)$_2$CH$_3$, NH$_2$, 3,4-methylenedioxy, —N(CH$_3$)$_2$, —NH—S(O)$_2$-phenyl, —NH—C(O)O—CH$_2$-4-pyridine, —NH—C(O)CH$_2$-morpholine, —NH—C(O)CH$_2$—N(CH$_3$)$_2$, —NH—C(O)CH$_2$-piperazine, —NH—C(O)CH$_2$-pyrrolidine, —NH—C(O)C(O)-morpholine, —NH—C(O)C(O)-piperazine, —NH—C(O)C(O)-pyrrolidine, —O—C(O)CH$_2$—N(CH$_3$)$_2$, or —O—(CH$_2$)$_2$—N(CH$_3$)$_2$ and wherein at least one of said substituents is in the ortho position.

3. The compound according to claim 2, wherein Q$_1$ contains at least two substituents, both of which are in the ortho position.

4. The compound according to claim 2, wherein Q$_1$ is selected from:

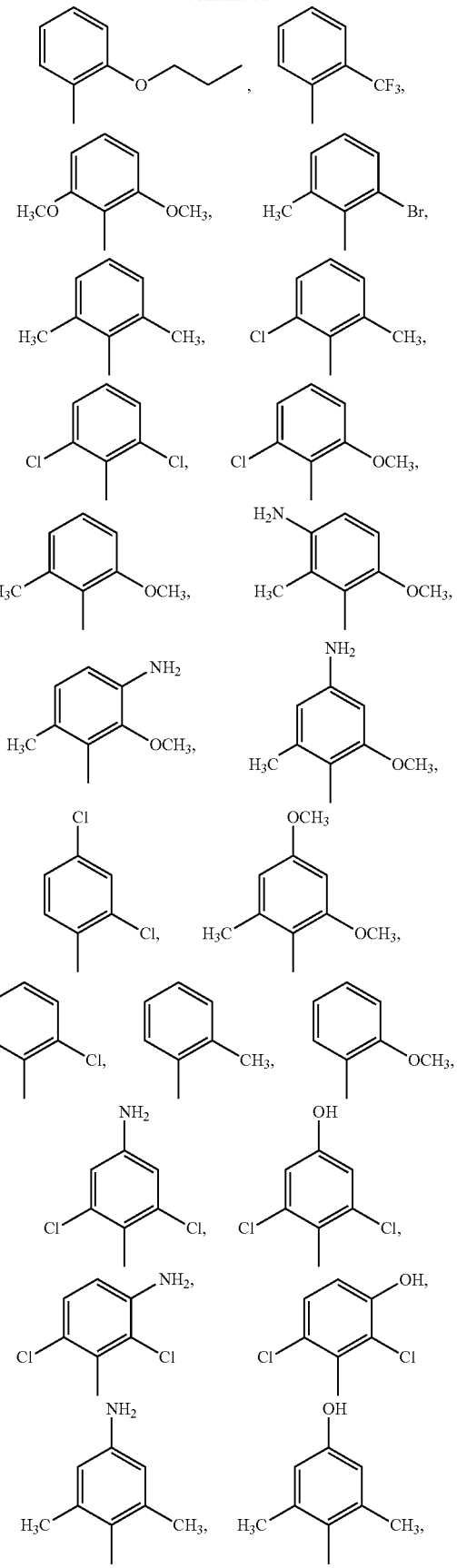

-continued
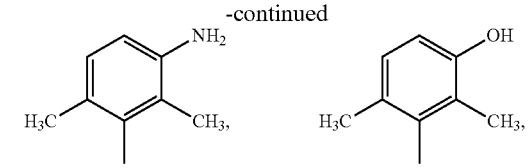
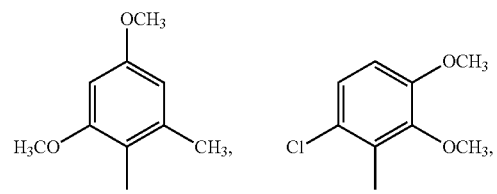
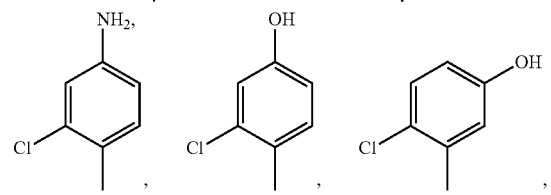
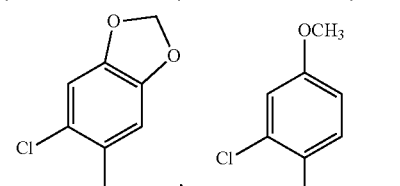
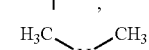
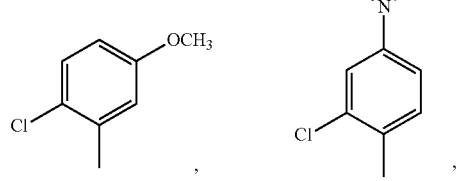
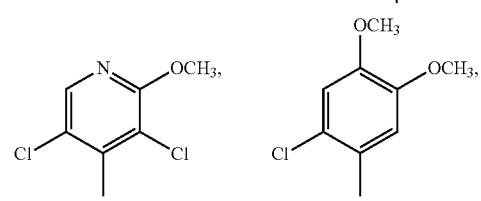
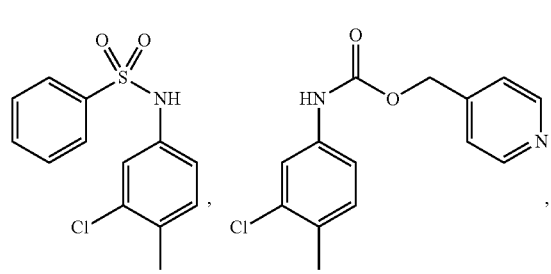
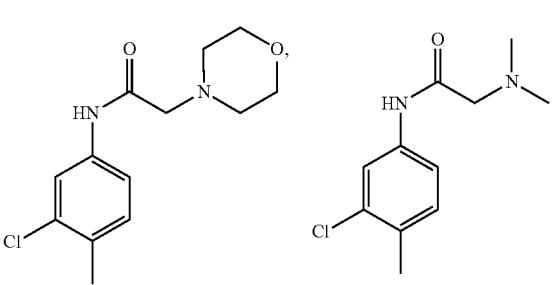
-continued
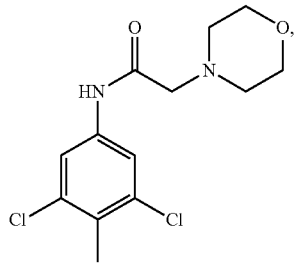
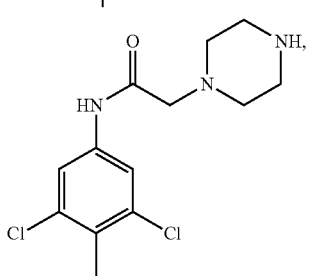
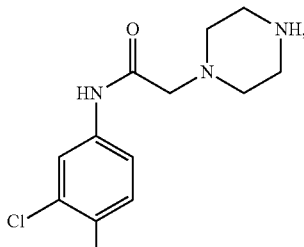
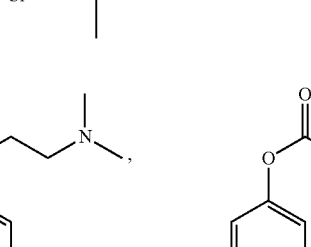
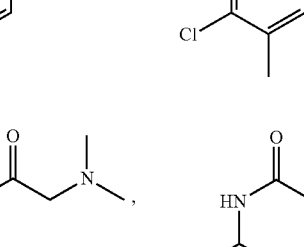
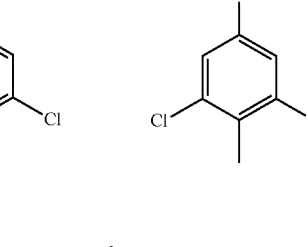
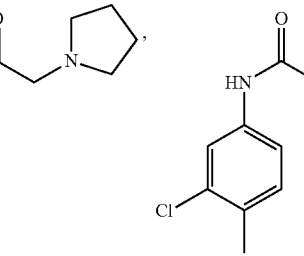
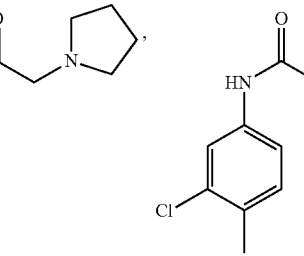

-continued

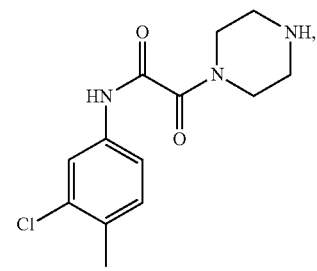

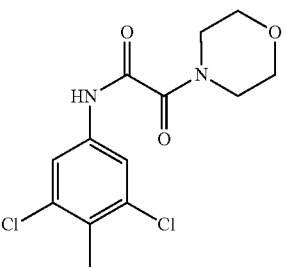

or

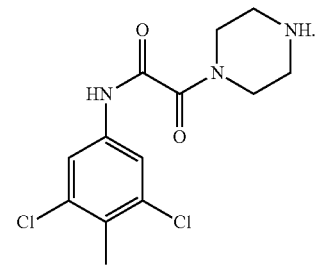

5. The compound according to claim 4, wherein $Q_1$ is selected from 2-fluoro-6-trifluoromethylphenyl, 2,6-difluorophenyl, 2,6-dichlorophenyl, 2-chloro-4-hydroxyphenyl, 2-chloro-4-aminophenyl, 2,6-dichloro-4-aminophenyl, 2,6-dichloro-3-aminophenyl, 2,6-dimethyl-4-hydroxyphenyl, 2-methoxy-3,5-dichloro-4-pyridyl, 2-chloro-4,5 methylenedioxy phenyl, or 2-chloro-4-(N-2-morpholino-acetamido) phenyl.

6. The compound according to claim 1, wherein $Q_2$ is selected from phenyl or pyridyl and wherein $Q_2$ optionally contains up to 3 substituents, each of which is independently selected from chloro, fluoro, bromo, methyl, ethyl, isopropyl, —$OCH_3$, —OH, —$NH_2$, —$CF_3$, —$OCF_3$, —$SCH_3$, —C(O)OH, —C(O)$OCH_3$, —$CH_2NH_2$, —N($CH_3$)$_2$, —$CH_2$-pyrrolidine, —$CH_2OH$, —$CH_2$—N($CH_3$)$_2$, —$CH_2$-piperazine, —NH—C(=NH)—$NH_2$, —$CH_2$—NH—C(=NH)—$NH_2$, and —$CH_2$—NH-imidazole.

7. The compound according to claim 6, wherein, $Q_2$ is selected from:

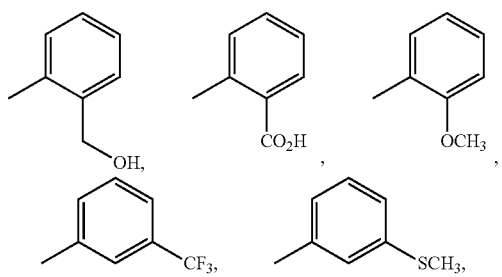

-continued

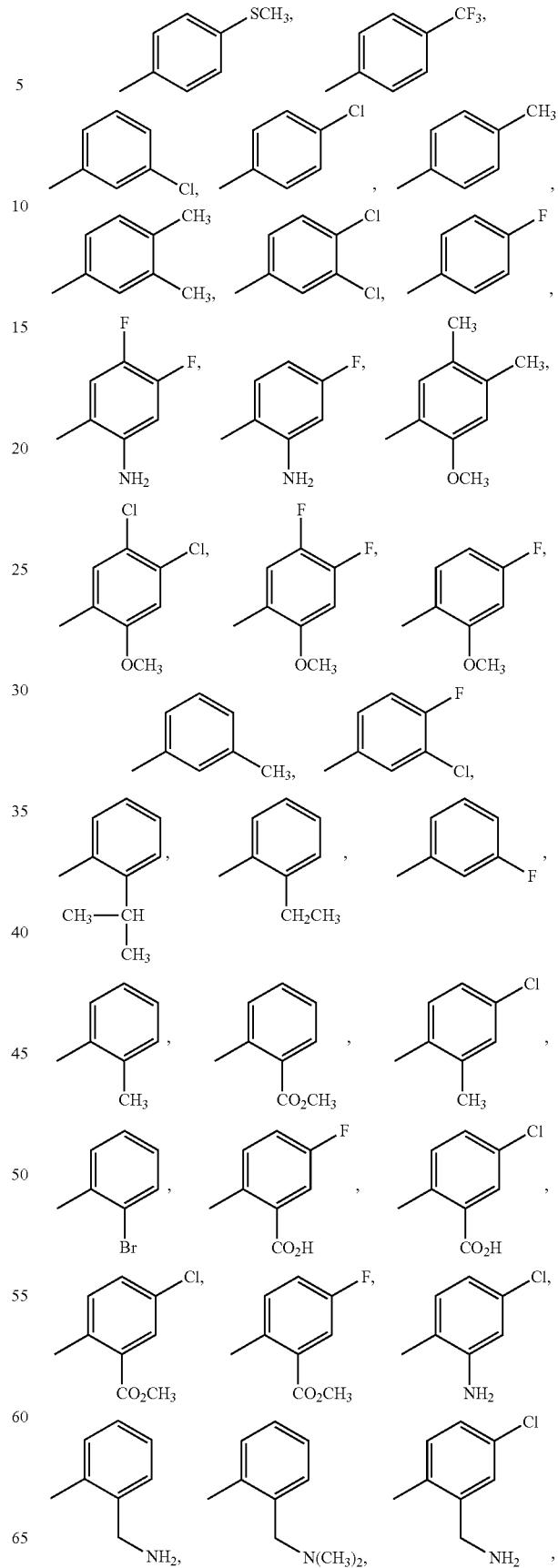

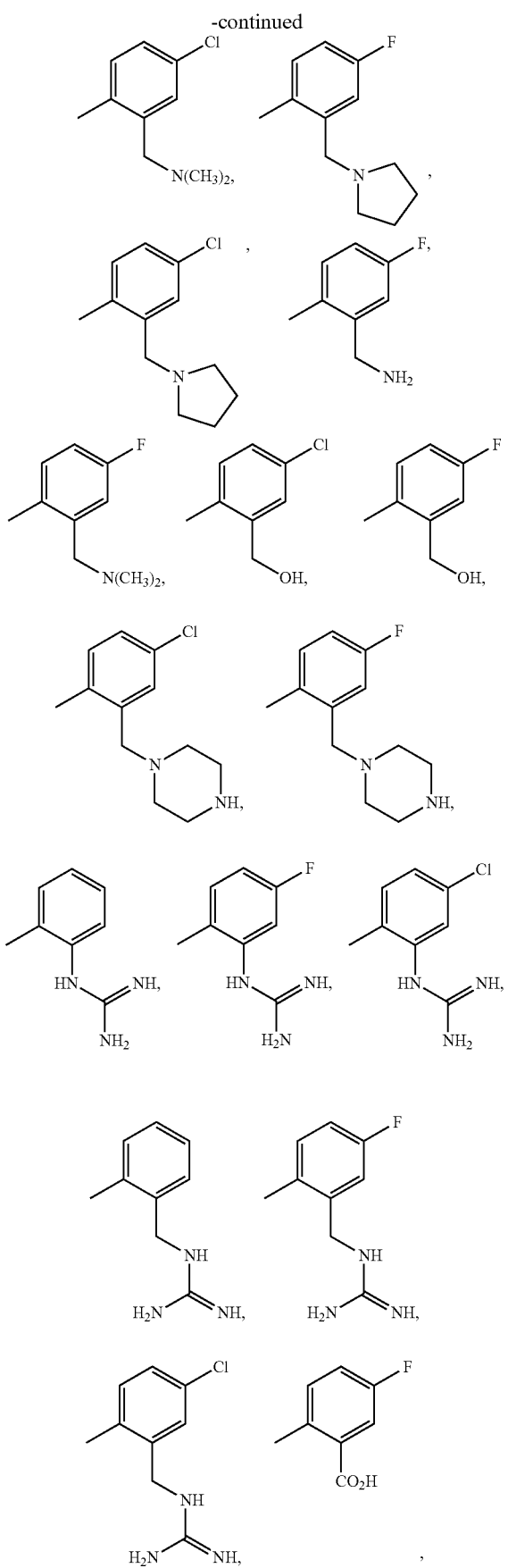

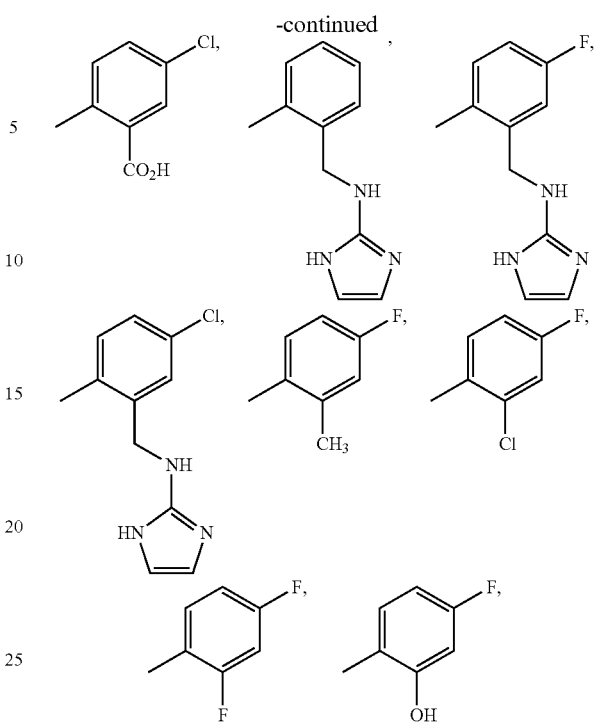

unsubstituted 2-pyridyl or unsubstituted phenyl.

8. The compound according to claim 7, wherein $Q_2$ is selected from phenyl, 2-isopropylphenyl, 3,4-dimethylphenyl, 2-ethylphenyl, 3-fluorophenyl, 2-methylphenyl, 3-chloro-4-fluorophenyl, 3-chlorophenyl, 2-carbomethoxylphenyl, 2-carboxyphenyl, 2-methyl-4-chlorophenyl, 2-bromophenyl, 2-pyridyl, 2-methylenehydroxyphenyl, 4-fluorophenyl, 2-methyl-4-fluorophenyl, 2-chloro-4-fluorophenyl, 2,4-difluorophenyl, 2-hydroxy-4-fluorophenyl or 2-methylenehydroxy-4-fluorophenyl.

9. The compound according to claim 1, wherein X is selected from —S—, —O—, —S(O$_2$)—, —S(O)—, —NR$^2$—, —C(R$^2$)$_2$— or —C(O)—.

10. The compound according to claim 8, wherein X is S.

11. The compound according to claim 1, wherein n is 1.

12. The compound according to claim 1, wherein each R attached to Y is independently selected from hydrogen or methyl.

13. The compound according to claim 1, wherein said compound is selected from any one of the following compounds:

| cpd # | structure |
|---|---|
| 101 | 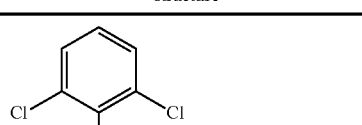 |

-continued
| cpd # | structure |
|---|---|
| 102 | 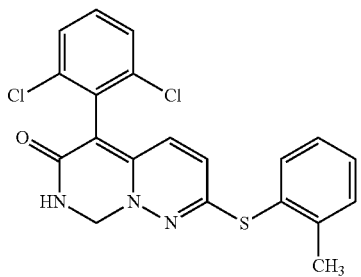 |
| 103 | 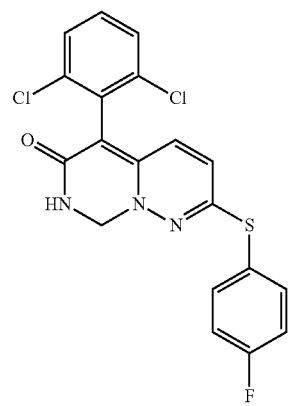 |
| 112 | 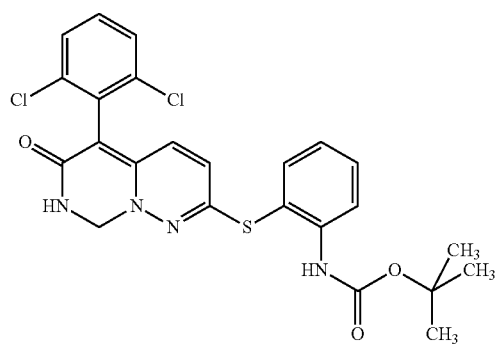 |
| 104 | 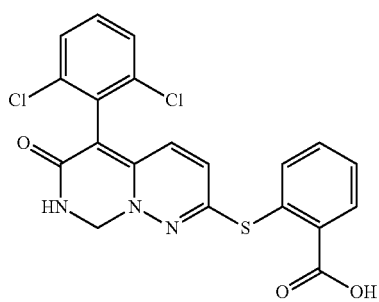 |
-continued
| cpd # | structure |
|---|---|
| 105 | 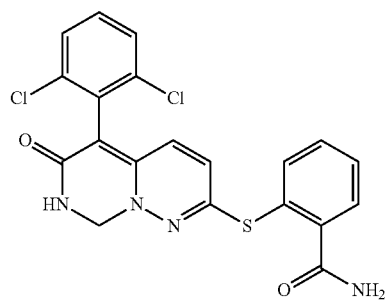 |
| 106 | 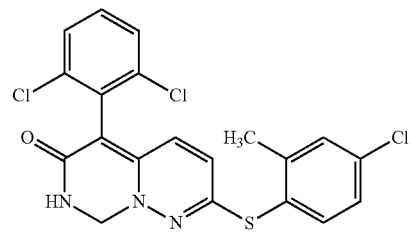 |
| 107 | 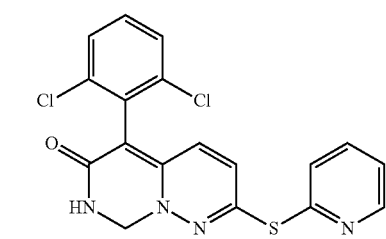 |
| 113 | 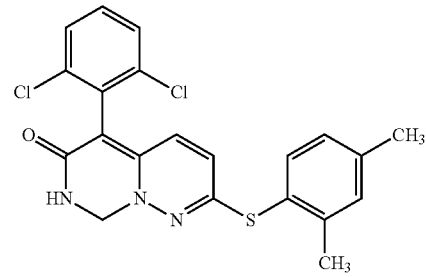 |
| 114 | 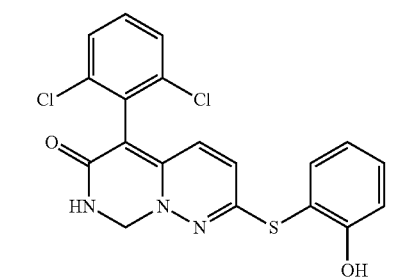 |

US 8,338,412 B2
113
-continued
| cpd # | structure |
|---|---|
| 115 | 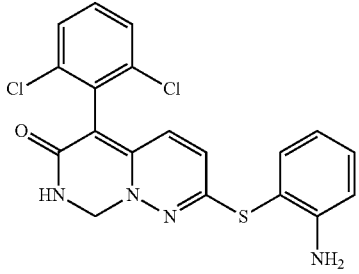 |
| 116 | 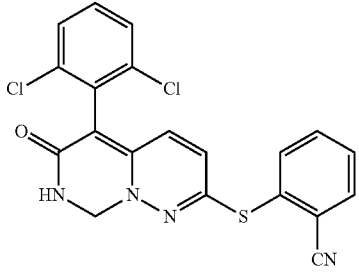 |
| 108 | 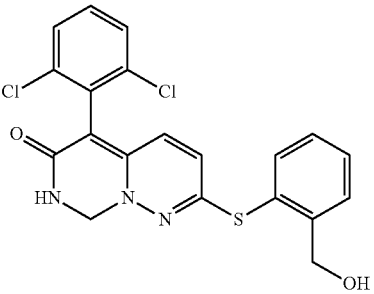 |
| 109 | 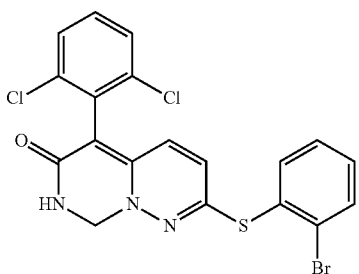 |
| 119 | 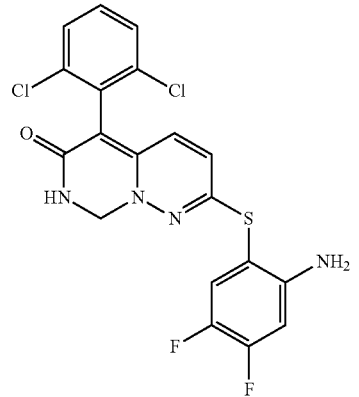 |
114
-continued
| cpd # | structure |
|---|---|
| 120 | 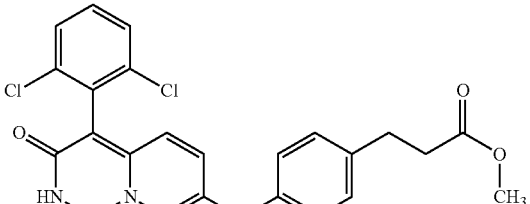 |
| 117 | 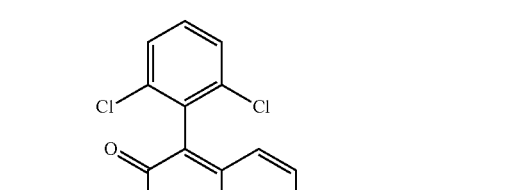 |
| 118 | 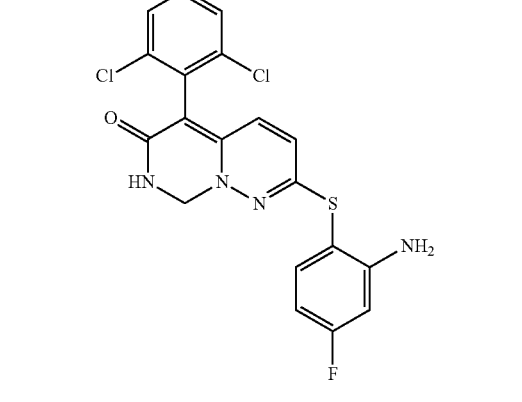 |
| 128 | 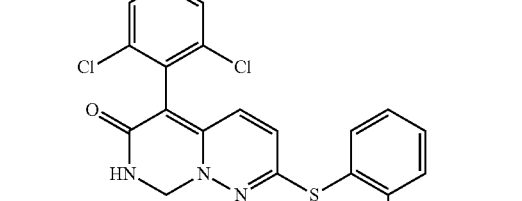 |
| 129 | 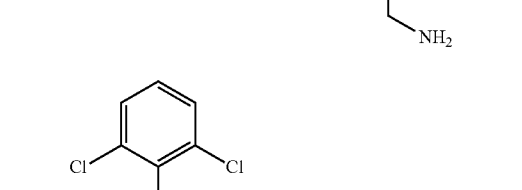 |

-continued
| cpd # | structure |
|---|---|
| 121 | 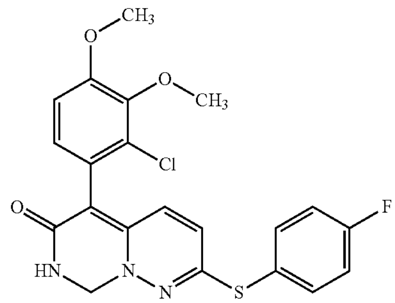 |
| 122 | 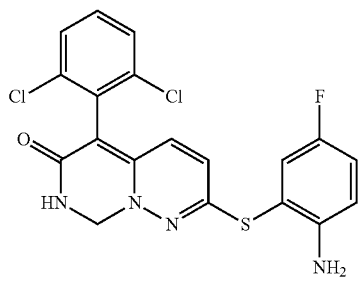 |
| 123 | 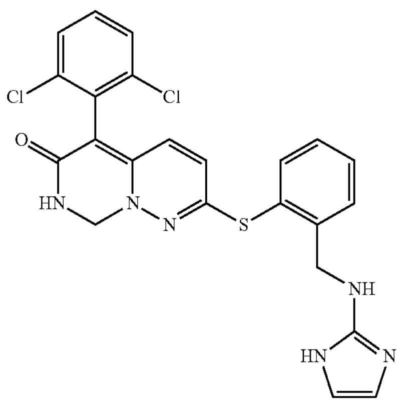 |
| 124 | 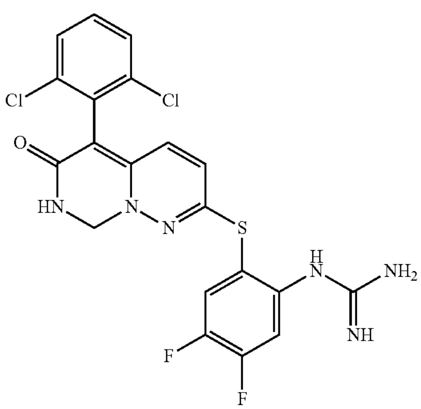 |
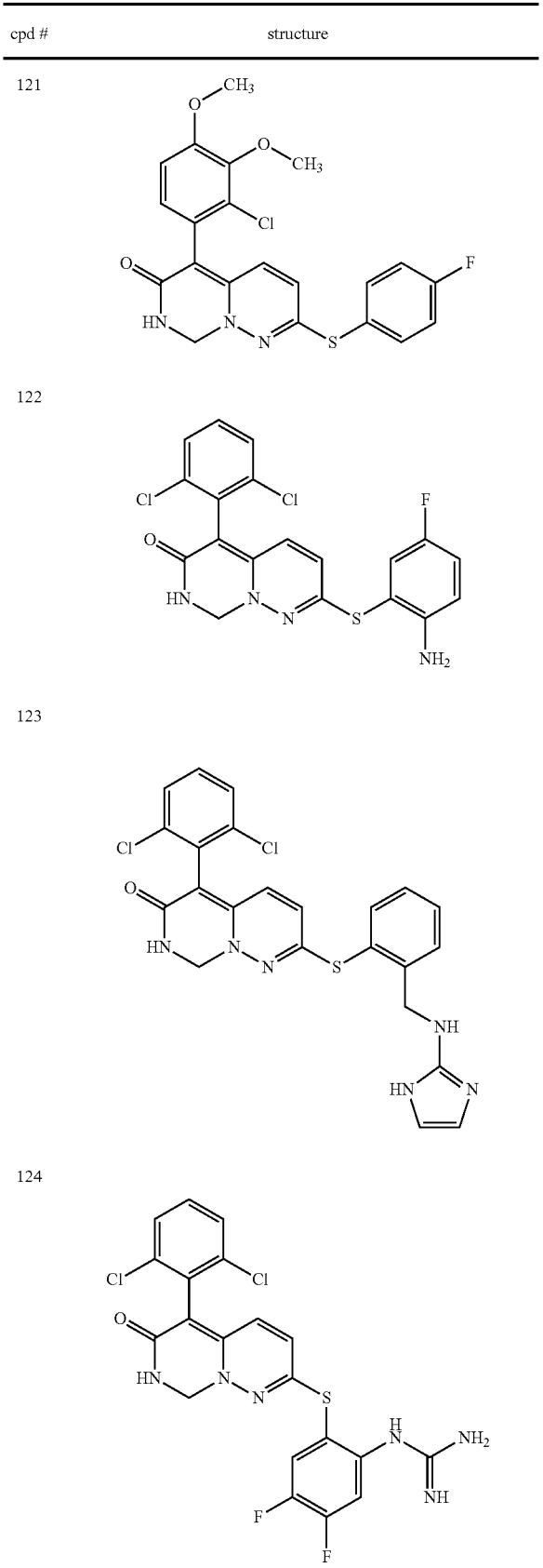
-continued
| cpd # | structure |
|---|---|
| 125 | 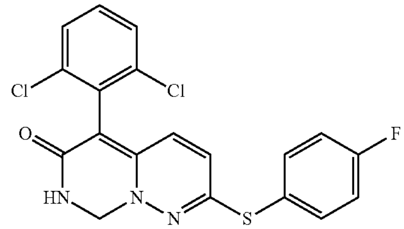 |
| 130 | 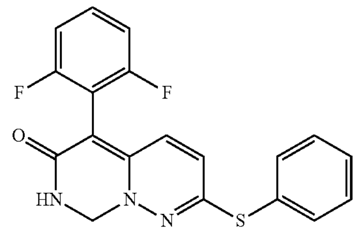 |
| 131 | 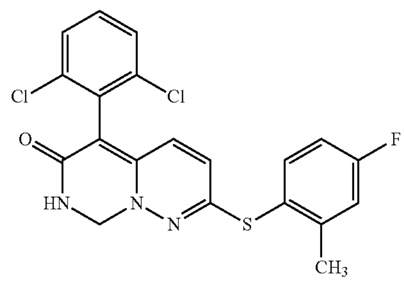 |
| 132 | 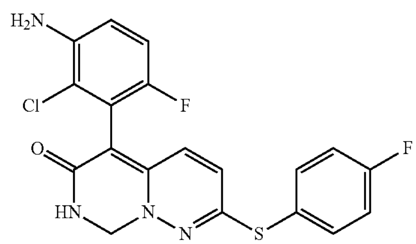 |
| 133 | 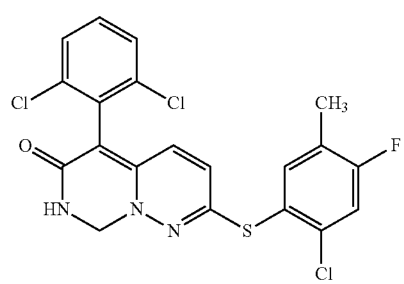 |
| 134 | 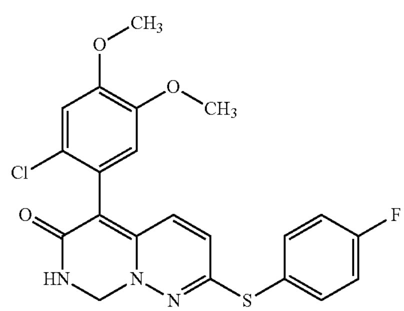 |
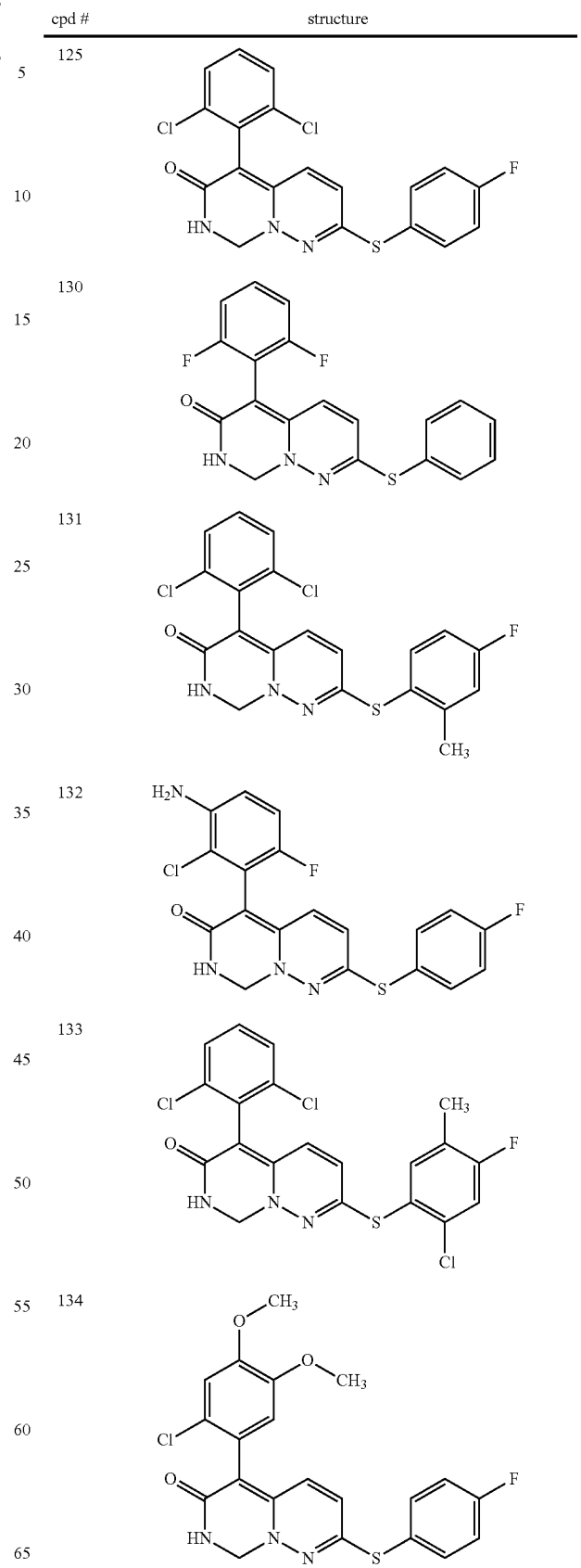

-continued
| cpd # | structure |
|---|---|
| 126 | 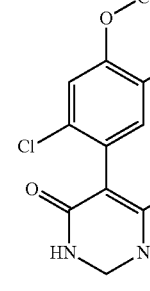 |
| 127 | 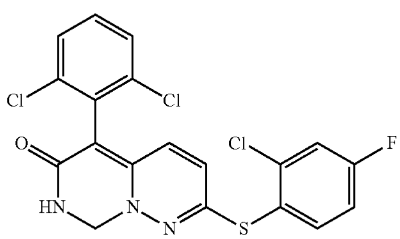 |
| 137 | 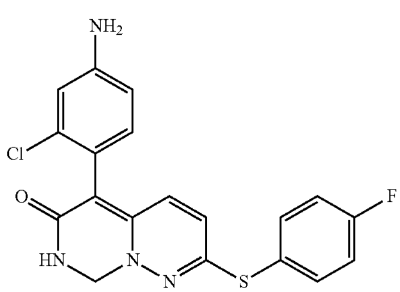 |
| 138 | 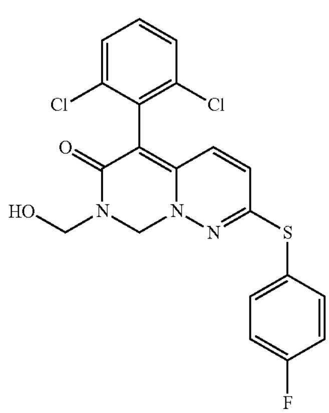 |
-continued
| cpd # | structure |
|---|---|
| 135 | 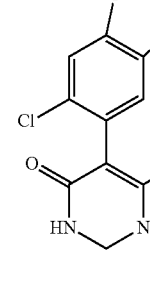 |
| 136 | 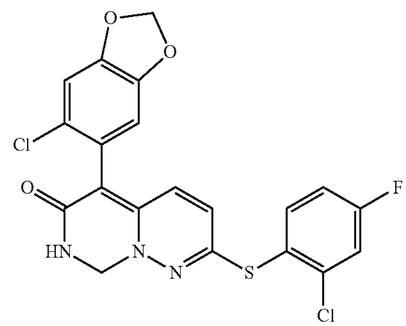 |
| 142 | 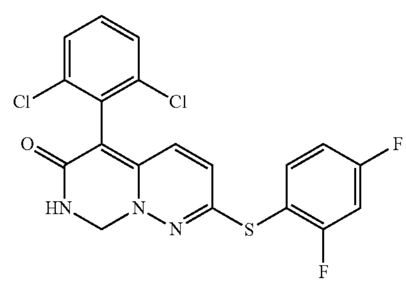 |
| 143 | 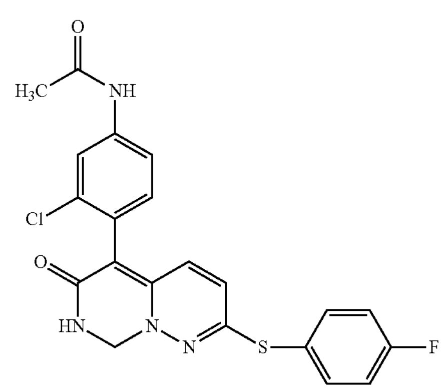 |
| 139 | 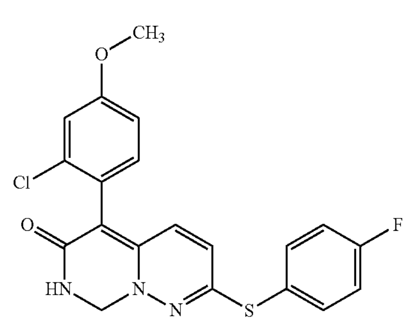 |

| cpd # | structure |
|---|---|
| 140 | 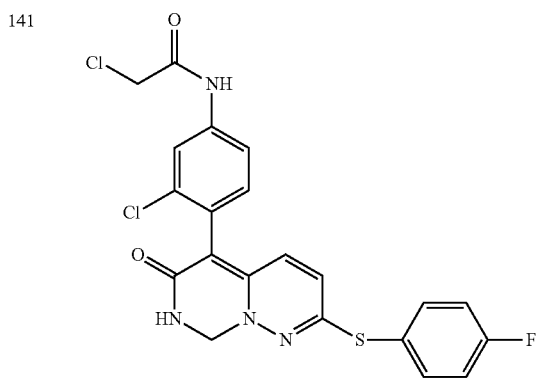 |
| 141 | 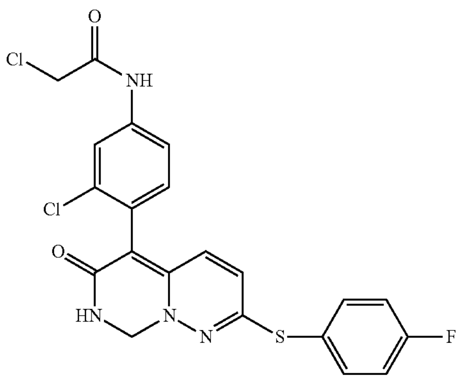 |
| 144 | 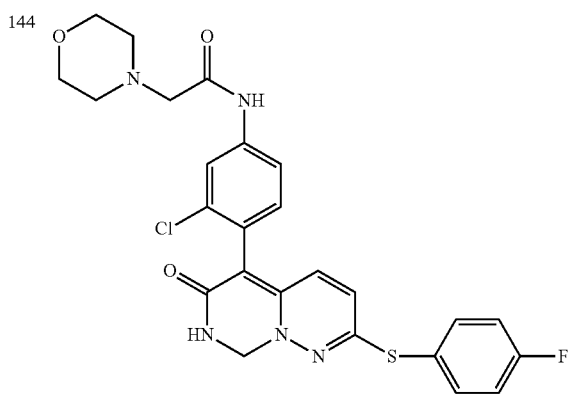 |

| cpd # | structure |
|---|---|
| 145 | 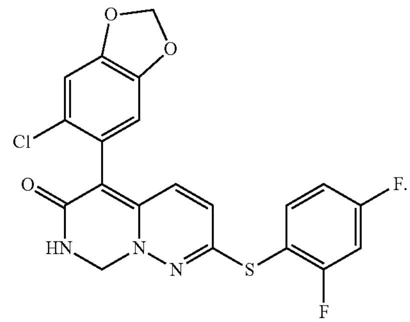 |

14. A pharmaceutical composition comprising an amount of a compound according to claim 1 effective to inhibit p38, and a pharmaceutically acceptable carrier.

15. A method of treating inflammatory diseases, destructive bone disorders, reperfusion/ischemia in stroke, myocardial ischemia, renal ischemia, cardiac hypertrophy, rheumatoid arthritis, inflammatory bowel disease, ulcerative colitis, or Crohn's disease in a patient, said method comprising administering to said patient a composition according to claim 14.

16. The method according to claim 15, wherein said method is used to treat an inflammatory disease selected from acute pancreatitis, chronic pancreatitis, asthma, allergies, or adult respiratory distress syndrome.

17. The method according to claim 15, wherein said method is used to treat rheumatoid arthritis, inflammatory bowel disease, ulcerative colitis, or Crohn's disease.

18. The method according to claim 15, wherein said method is used to treat a destructive bone disorder selected from osteoarthritis, osteoporosis or multiple myeloma-related bone disorder.

19. The method according to claim 15, wherein said method is used to treat ischemia/reperfusion in stroke, myocardial ischemia, or renal ischemia.

* * * * *